(12) United States Patent
Saravia et al.

(10) Patent No.: US 9,259,250 B2
(45) Date of Patent: *Feb. 16, 2016

(54) FRACTURE FIXATION DEVICE, TOOLS AND METHODS

(71) Applicant: Sonoma Orthopedic Products, Inc., Santa Rosa, CA (US)

(72) Inventors: Heber Saravia, Santa Rosa, CA (US); Brian A. Hauck, Windsor, CA (US); Trung Pham, Santa Rosa, CA (US); Charles L. Nelson, Santa Rosa, CA (US); Arthur E. Anderson, III, Sunnyvale, CA (US); William W. Bowen, Willits, CA (US); Stephen R. McDaniel, Bodega Bay, CA (US)

(73) Assignee: Sonoma Orthopedic Products, Inc., Santa Rosa, CA (US)

( * ) Notice: Subject to any disclaimer, the term of this patent is extended or adjusted under 35 U.S.C. 154(b) by 182 days.

This patent is subject to a terminal disclaimer.

(21) Appl. No.: 13/861,315

(22) Filed: Apr. 11, 2013

(65) Prior Publication Data

US 2013/0231665 A1 Sep. 5, 2013

Related U.S. Application Data

(63) Continuation of application No. 13/032,437, filed on Feb. 22, 2011, now Pat. No. 8,439,917, which is a continuation of application No. 11/944,366, filed on Nov. 21, 2007, now Pat. No. 7,909,825.

(Continued)

(51) Int. Cl.
*A61B 17/72* (2006.01)
*A61B 17/17* (2006.01)
*A61B 17/88* (2006.01)

(52) U.S. Cl.
CPC ......... *A61B 17/7266* (2013.01); *A61B 17/1725* (2013.01); *A61B 17/8872* (2013.01); *A61B 17/7241* (2013.01)

(58) Field of Classification Search
CPC ........... A61B 17/7266; A61B 17/7225; A61B 17/744; A61B 17/72; A61B 17/7258; A61B 17/746; A61B 17/1725; A61B 17/7233; A61B 17/725; A61B 17/7283; A61B 17/742; A61B 17/7208; A61B 17/7241; A61B 17/921; A61B 17/1717; A61B 17/7216; A61B 17/7275; A61B 17/1721; A61B 17/7291
USPC .................... 606/62–68, 282, 320, 105, 86 R
See application file for complete search history.

(56) References Cited

U.S. PATENT DOCUMENTS

| 958,127 A | 5/1910 | Hufrud |
| 1,169,635 A | 1/1916 | Grimes |

(Continued)

FOREIGN PATENT DOCUMENTS

| CA | 2561552 A1 | 11/2005 |
| EP | 1582163 A1 | 11/2003 |

(Continued)

OTHER PUBLICATIONS

US 6,030,385, Feb. 2000, Faccioli et al. (withdrawn).

(Continued)

*Primary Examiner* — Pedro Philogene
*Assistant Examiner* — Lynnsy Summitt
(74) *Attorney, Agent, or Firm* — Knobbe, Martens, Olson & Bear, LLP

(57) ABSTRACT

Bone fixation methods and devices with an elongate body having a longitudinal axis and having a flexible state and a rigid state, a plurality of grippers, a rigid hub connected to the elongated body, and an actuator operably connected to the grippers to deploy the grippers from a first shape to an expanded second shape. One method can include inserting a bone fixation device into an intramedullary space of the bone to place at least a portion of an elongate body of the fixation device in a flexible state on one side of the fracture and at least a portion of a rigid hub on another side of the fracture, and operating an actuator to deploy a plurality of grippers of the fixation device to engage an inner surface of the intramedullary space to anchor the fixation device to the bone.

16 Claims, 71 Drawing Sheets

Related U.S. Application Data

(60) Provisional application No. 60/867,011, filed on Nov. 22, 2006, provisional application No. 60/866,976, filed on Nov. 22, 2006, provisional application No. 60/949,071, filed on Jul. 11, 2007.

(56) References Cited

U.S. PATENT DOCUMENTS

| | | | |
|---|---|---|---|
| 1,790,841 A | 2/1931 | Rosen | |
| 2,502,267 A | 3/1950 | McPherson | |
| 2,685,877 A | 8/1954 | Dobelle | |
| 2,998,007 A | 8/1961 | Herzog | |
| 3,118,444 A | 1/1964 | Serrato, Jr. | |
| 3,441,017 A | 4/1969 | Kaessmann | |
| 3,626,935 A | 12/1971 | Pollock et al. | |
| 3,710,789 A | 1/1973 | Ersek | |
| 3,759,257 A | 9/1973 | Fischer et al. | |
| 3,760,802 A | 9/1973 | Fischer et al. | |
| 3,779,239 A * | 12/1973 | Fischer | A61B 17/7258 411/38 |
| 3,791,380 A | 2/1974 | Dawidowski | |
| 3,805,775 A * | 4/1974 | Fischer | A61B 17/74 606/68 |
| 3,846,846 A | 11/1974 | Fischer | |
| 3,955,565 A | 5/1976 | Johnson, Jr. | |
| 3,978,528 A | 9/1976 | Crep | |
| 3,986,504 A * | 10/1976 | Avila | A61B 17/7266 606/63 |
| 4,007,528 A | 2/1977 | Shea et al. | |
| 4,011,602 A | 3/1977 | Rybicki et al. | |
| 4,016,874 A | 4/1977 | Maffei et al. | |
| 4,050,646 A | 9/1977 | Burchette, Jr. | |
| 4,064,567 A | 12/1977 | Burstein et al. | |
| 4,065,816 A | 1/1978 | Sawyer | |
| 4,091,806 A | 5/1978 | Aginsky | |
| 4,146,022 A | 3/1979 | Johnson et al. | |
| 4,164,794 A | 8/1979 | Spector et al. | |
| 4,190,044 A | 2/1980 | Wood | |
| D255,048 S | 5/1980 | Miller | |
| 4,204,531 A | 5/1980 | Aginsky | |
| 4,227,518 A | 10/1980 | Aginsky | |
| 4,236,512 A | 12/1980 | Aginsky | |
| 4,237,875 A | 12/1980 | Tennanini | |
| 4,246,662 A | 1/1981 | Pastrick | |
| 4,262,665 A | 4/1981 | Roalstad et al. | |
| 4,275,717 A | 6/1981 | Bolesky | |
| 4,293,962 A | 10/1981 | Fuson | |
| 4,294,251 A | 10/1981 | Greenwald et al. | |
| 4,312,336 A | 1/1982 | Danieletto et al. | |
| 4,313,434 A | 2/1982 | Segal | |
| 4,338,926 A | 7/1982 | Kummer et al. | |
| 4,351,069 A | 9/1982 | Ballintyn et al. | |
| 4,352,212 A | 10/1982 | Greene et al. | |
| 4,353,358 A | 10/1982 | Emerson | |
| 4,379,451 A | 4/1983 | Getscher | |
| 4,409,974 A | 10/1983 | Freedland | |
| 4,453,539 A * | 6/1984 | Raftopoulos | A61B 17/7258 606/63 |
| 4,457,301 A | 7/1984 | Walker | |
| 4,459,708 A | 7/1984 | Buttazzoni | |
| 4,462,394 A | 7/1984 | Jacobs | |
| 4,467,794 A | 8/1984 | Maffei et al. | |
| RE31,809 E | 1/1985 | Danieletto et al. | |
| 4,492,226 A | 1/1985 | Belykh et al. | |
| 4,503,847 A | 3/1985 | Mouradian | |
| 4,519,100 A | 5/1985 | Wills et al. | |
| 4,520,511 A | 6/1985 | Gianezio et al. | |
| 4,522,200 A | 6/1985 | Stednitz | |
| 4,541,423 A | 9/1985 | Barber | |
| 4,552,136 A | 11/1985 | Kenna | |
| 4,589,883 A | 5/1986 | Kenna | |
| 4,590,930 A | 5/1986 | Kurth et al. | |
| 4,604,997 A | 8/1986 | De Bastiani et al. | |
| 4,621,627 A | 11/1986 | DeBastiani et al. | |
| 4,622,959 A | 11/1986 | Marcus | |
| 4,624,673 A | 11/1986 | Meyer | |
| 4,628,920 A | 12/1986 | Mathys, Jr. et al. | |
| 4,632,101 A | 12/1986 | Freedland | |
| 4,643,177 A | 2/1987 | Sheppard et al. | |
| 4,651,724 A | 3/1987 | Berentey et al. | |
| 4,653,487 A | 3/1987 | Maale | |
| 4,662,887 A | 5/1987 | Turner et al. | |
| 4,667,663 A | 5/1987 | Miyata | |
| D290,399 S | 6/1987 | Kitchens | |
| 4,681,590 A | 7/1987 | Tansey | |
| 4,697,585 A | 10/1987 | Williams | |
| 4,705,027 A | 11/1987 | Klaue | |
| 4,705,032 A | 11/1987 | Keller | |
| 4,721,103 A | 1/1988 | Freedland | |
| 4,735,625 A | 4/1988 | Davidson | |
| 4,753,657 A | 6/1988 | Lee et al. | |
| 4,776,330 A | 10/1988 | Chapman et al. | |
| 4,781,181 A | 11/1988 | Tanguy | |
| 4,805,595 A | 2/1989 | Kanbara | |
| 4,805,607 A | 2/1989 | Engelhardt et al. | |
| 4,813,963 A | 3/1989 | Hori et al. | |
| 4,817,591 A | 4/1989 | Klaue et al. | |
| 4,827,919 A | 5/1989 | Barbarito et al. | |
| 4,828,277 A | 5/1989 | De Bastiani et al. | |
| 4,854,312 A | 8/1989 | Raftopoulos et al. | |
| 4,858,602 A | 8/1989 | Seidel et al. | |
| 4,862,883 A | 9/1989 | Freeland | |
| 4,871,369 A | 10/1989 | Muller | |
| 4,875,474 A | 10/1989 | Border | |
| 4,875,475 A | 10/1989 | Comte et al. | |
| 4,896,662 A | 1/1990 | Noble | |
| 4,921,499 A | 5/1990 | Hoffman et al. | |
| 4,927,424 A | 5/1990 | McConnell et al. | |
| 4,932,969 A | 6/1990 | Frey et al. | |
| 4,943,291 A | 7/1990 | Tanguy | |
| 4,946,179 A | 8/1990 | De Bastiani et al. | |
| 4,959,066 A | 9/1990 | Dunn et al. | |
| 4,969,889 A | 11/1990 | Greig | |
| 4,976,258 A | 12/1990 | Richter et al. | |
| 4,978,349 A | 12/1990 | Frigg | |
| 4,978,358 A | 12/1990 | Bobyn | |
| 4,988,349 A | 1/1991 | Pennig | |
| 5,002,547 A | 3/1991 | Poggie et al. | |
| 5,002,580 A | 3/1991 | Noble et al. | |
| 5,006,120 A | 4/1991 | Carter et al. | |
| 5,013,314 A | 5/1991 | Firica et al. | |
| 5,019,077 A | 5/1991 | De Bastiani et al. | |
| 5,026,374 A | 6/1991 | Dezza et al. | |
| 5,027,799 A | 7/1991 | Laico et al. | |
| 5,030,222 A | 7/1991 | Calandruccio et al. | |
| 5,034,012 A | 7/1991 | Frigg | |
| 5,034,013 A | 7/1991 | Kyle et al. | |
| 5,035,697 A | 7/1991 | Frigg | |
| 5,037,423 A | 8/1991 | Kenna | |
| 5,041,114 A | 8/1991 | Chapman et al. | |
| 5,041,115 A | 8/1991 | Frigg et al. | |
| 5,053,035 A | 10/1991 | McLaren | |
| 5,057,103 A * | 10/1991 | Davis | A61B 17/7225 606/63 |
| 5,062,854 A | 11/1991 | Noble et al. | |
| 5,066,296 A | 11/1991 | Chapman et al. | |
| 5,084,050 A | 1/1992 | Draenert | |
| 5,092,892 A | 3/1992 | Ashby | |
| 5,098,433 A | 3/1992 | Freedland | |
| 5,100,404 A | 3/1992 | Hayes | |
| 5,102,413 A | 4/1992 | Poddar | |
| 5,108,404 A | 4/1992 | Scholten et al. | |
| 5,112,333 A | 5/1992 | Fixel | |
| 5,116,335 A | 5/1992 | Hannon et al. | |
| 5,116,380 A | 5/1992 | Hewka et al. | |
| 5,122,141 A | 6/1992 | Simpson et al. | |
| 5,122,146 A | 6/1992 | Chapman et al. | |
| 5,124,106 A | 6/1992 | Morr et al. | |
| 5,147,408 A | 9/1992 | Noble et al. | |
| 5,152,766 A | 10/1992 | Kirkley | |
| 5,163,963 A | 11/1992 | Hewka et al. | |
| 5,171,324 A | 12/1992 | Campana et al. | |
| 5,176,681 A | 1/1993 | Lawes et al. | |
| 5,178,621 A | 1/1993 | Cook et al. | |

(56) References Cited

U.S. PATENT DOCUMENTS

| | | |
|---|---|---|
| 5,190,544 A | 3/1993 | Chapman et al. |
| 5,190,546 A | 3/1993 | Jervis |
| 5,192,281 A | 3/1993 | de la Caffiniere |
| 5,197,966 A | 3/1993 | Sommerkamp |
| 5,197,990 A | 3/1993 | Lawes et al. |
| 5,201,735 A | 4/1993 | Chapman et al. |
| 5,201,767 A | 4/1993 | Caldarise et al. |
| 5,211,664 A | 5/1993 | Tepic et al. |
| 5,217,049 A | 6/1993 | Forsyth |
| 5,263,955 A | 11/1993 | Baumgart et al. |
| 5,268,000 A | 12/1993 | Ottieri et al. |
| 5,281,224 A | 1/1994 | Faccioli et al. |
| 5,281,225 A | 1/1994 | Vicenzi |
| 5,292,322 A | 3/1994 | Faccioli et al. |
| 5,295,991 A | 3/1994 | Frigg |
| 5,303,718 A | 4/1994 | Krajicek |
| 5,314,489 A | 5/1994 | Hoffman et al. |
| 5,320,622 A | 6/1994 | Faccioli et al. |
| 5,320,623 A | 6/1994 | Pennig |
| 5,326,376 A | 7/1994 | Warner et al. |
| 5,334,184 A | 8/1994 | Bimman |
| 5,342,360 A | 8/1994 | Faccioli et al. |
| 5,342,362 A | 8/1994 | Kenyon et al. |
| 5,346,496 A | 9/1994 | Pennig |
| 5,350,379 A | 9/1994 | Spievack |
| 5,352,227 A | 10/1994 | O'Hara |
| 5,358,534 A | 10/1994 | Dudasik et al. |
| 5,364,398 A | 11/1994 | Chapman et al. |
| 5,368,594 A | 11/1994 | Martin et al. |
| 5,376,090 A | 12/1994 | Pennig |
| 5,376,123 A | 12/1994 | Klaue et al. |
| 5,380,328 A | 1/1995 | Morgan |
| 5,383,932 A | 1/1995 | Wilson et al. |
| 5,387,243 A | 2/1995 | Devanathan |
| 5,397,328 A | 3/1995 | Behrens et al. |
| 5,403,321 A | 4/1995 | DiMarco |
| 5,411,503 A | 5/1995 | Hollstien et al. |
| 5,415,660 A | 5/1995 | Campbell et al. |
| 5,417,695 A | 5/1995 | Axelson, Jr. |
| RE34,985 E | 6/1995 | Pennig |
| 5,423,848 A | 6/1995 | Washizuka et al. |
| 5,423,850 A | 6/1995 | Berger |
| 5,433,718 A | 7/1995 | Brinker |
| 5,433,720 A | 7/1995 | Faccioli et al. |
| 5,441,500 A | 8/1995 | Seidel et al. |
| 5,443,477 A | 8/1995 | Marin et al. |
| 5,445,642 A | 8/1995 | McNulty et al. |
| 5,454,813 A | 10/1995 | Lawes |
| 5,454,816 A | 10/1995 | Ashby |
| 5,458,599 A * | 10/1995 | Adobbati ............ A61B 17/7225 606/54 |
| 5,458,651 A | 10/1995 | Lawes |
| 5,458,653 A | 10/1995 | Davidson |
| 5,468,242 A | 11/1995 | Reisberg |
| 5,472,444 A * | 12/1995 | Huebner ............ A61B 17/7283 606/62 |
| 5,478,341 A | 12/1995 | Cook et al. |
| 5,480,400 A | 1/1996 | Berger |
| 5,484,438 A | 1/1996 | Pennig |
| 5,484,446 A | 1/1996 | Burke et al. |
| 5,488,761 A | 2/1996 | Leone |
| 5,490,852 A | 2/1996 | Azer et al. |
| 5,505,734 A | 4/1996 | Caniggia et al. |
| 5,514,137 A | 5/1996 | Coutts |
| 5,516,335 A | 5/1996 | Kummer et al. |
| 5,520,695 A | 5/1996 | Luckman |
| 5,527,316 A | 6/1996 | Stone et al. |
| 5,531,748 A | 7/1996 | de la Caffiniere |
| 5,534,004 A | 7/1996 | Santangelo |
| 5,545,162 A | 8/1996 | Huebner |
| 5,549,610 A | 8/1996 | Russell et al. |
| 5,549,706 A | 8/1996 | McCarthy |
| 5,554,192 A | 9/1996 | Crowninshield |
| 5,556,433 A | 9/1996 | Gabriel et al. |
| 5,562,667 A | 10/1996 | Shuler et al. |
| 5,562,673 A | 10/1996 | Koblish et al. |
| 5,562,674 A | 10/1996 | Stalcup et al. |
| 5,562,675 A | 10/1996 | McNulty et al. |
| 5,569,249 A | 10/1996 | James et al. |
| 5,571,189 A | 11/1996 | Kuslich |
| 5,571,204 A | 11/1996 | Nies |
| 5,573,536 A | 11/1996 | Grosse et al. |
| 5,578,035 A | 11/1996 | Lin |
| 5,586,985 A | 12/1996 | Putnam et al. |
| 5,591,169 A | 1/1997 | Benoist |
| 5,591,196 A | 1/1997 | Marin et al. |
| 5,593,451 A | 1/1997 | Averill et al. |
| 5,593,452 A | 1/1997 | Higham et al. |
| 5,605,713 A | 2/1997 | Boltong |
| 5,607,431 A | 3/1997 | Dudasik et al. |
| 5,613,970 A | 3/1997 | Houston et al. |
| 5,618,286 A | 4/1997 | Brinker |
| 5,618,300 A | 4/1997 | Marin et al. |
| 5,620,449 A | 4/1997 | Faccioli et al. |
| 5,624,440 A | 4/1997 | Huebner et al. |
| 5,624,447 A | 4/1997 | Myers |
| 5,626,580 A | 5/1997 | Brosnahan |
| 5,643,258 A | 7/1997 | Robioneck et al. |
| 5,645,545 A | 7/1997 | Bryant |
| 5,645,599 A | 7/1997 | Samani |
| 5,658,283 A | 8/1997 | Huebner |
| 5,658,287 A | 8/1997 | Hofmann et al. |
| 5,658,292 A | 8/1997 | Axelson, Jr. |
| 5,658,293 A | 8/1997 | Vanlaningham |
| 5,658,351 A | 8/1997 | Dudasik et al. |
| 5,662,648 A | 9/1997 | Faccioli et al. |
| 5,662,649 A | 9/1997 | Huebner |
| 5,662,712 A | 9/1997 | Pathak et al. |
| 5,665,090 A | 9/1997 | Rockwood et al. |
| 5,665,091 A | 9/1997 | Noble et al. |
| 5,681,289 A | 10/1997 | Wilcox et al. |
| 5,681,316 A | 10/1997 | DeOrio et al. |
| 5,681,318 A | 10/1997 | Pennig et al. |
| 5,683,389 A | 11/1997 | Orsak |
| 5,683,460 A | 11/1997 | Persoons |
| 5,688,271 A | 11/1997 | Faccioli et al. |
| 5,688,279 A | 11/1997 | McNulty et al. |
| 5,690,634 A | 11/1997 | Muller et al. |
| 5,693,047 A | 12/1997 | Meyers et al. |
| 5,693,048 A | 12/1997 | Stalcup et al. |
| 5,695,729 A | 12/1997 | Chow et al. |
| 5,697,930 A | 12/1997 | Itoman et al. |
| 5,702,215 A | 12/1997 | Li |
| 5,702,481 A | 12/1997 | Lin |
| 5,702,487 A | 12/1997 | Averill et al. |
| 5,707,370 A | 1/1998 | Berki et al. |
| 5,718,704 A | 2/1998 | Medoff |
| 5,725,595 A | 3/1998 | Gustilo |
| 5,728,096 A | 3/1998 | Faccioli et al. |
| 5,741,256 A | 4/1998 | Bresina |
| 5,741,266 A | 4/1998 | Moran et al. |
| 5,749,872 A | 5/1998 | Kyle et al. |
| 5,749,880 A | 5/1998 | Banas et al. |
| 5,759,184 A | 6/1998 | Santangelo |
| 5,766,174 A | 6/1998 | Perry |
| 5,766,176 A | 6/1998 | Duncan |
| 5,766,178 A | 6/1998 | Michielli et al. |
| 5,766,179 A | 6/1998 | Faccioli et al. |
| 5,766,180 A | 6/1998 | Winquist |
| 5,772,662 A | 6/1998 | Chapman et al. |
| 5,772,663 A | 6/1998 | Whiteside et al. |
| 5,776,194 A | 7/1998 | Mikol et al. |
| 5,776,204 A | 7/1998 | Noble et al. |
| 5,779,703 A | 7/1998 | Benoist |
| 5,779,705 A | 7/1998 | Matthews |
| 5,782,921 A | 7/1998 | Colleran et al. |
| 5,785,057 A | 7/1998 | Fischer |
| 5,788,703 A | 8/1998 | Mittelmeier et al. |
| 5,807,241 A | 9/1998 | Heimberger |
| 5,810,750 A | 9/1998 | Buser |
| 5,810,820 A * | 9/1998 | Santori ............ A61B 17/744 606/63 |
| 5,810,826 A | 9/1998 | Akerfeldt et al. |
| 5,810,830 A | 9/1998 | Noble et al. |

(56) References Cited

U.S. PATENT DOCUMENTS

| | | |
|---|---|---|
| 5,814,047 A | 9/1998 | Emilio et al. |
| 5,814,681 A | 9/1998 | Hino et al. |
| 5,816,812 A | 10/1998 | Kownacki et al. |
| 5,827,282 A | 10/1998 | Pennig |
| 5,827,289 A | 10/1998 | Reiley et al. |
| 5,829,081 A | 11/1998 | Pearce |
| 5,836,949 A | 11/1998 | Campbell, Jr. et al. |
| 5,837,909 A | 11/1998 | Bill et al. |
| 5,849,004 A | 12/1998 | Bramlet |
| 5,849,014 A | 12/1998 | Mastrorio et al. |
| 5,849,035 A | 12/1998 | Pathak et al. |
| 5,855,581 A | 1/1999 | Koblish et al. |
| 5,858,020 A | 1/1999 | Johnson et al. |
| 5,863,295 A | 1/1999 | Averill et al. |
| 5,876,459 A | 3/1999 | Powell |
| 5,879,352 A * | 3/1999 | Filoso ............... A61B 17/7013 606/60 |
| 5,881,878 A | 3/1999 | Faccioli et al. |
| 5,882,351 A | 3/1999 | Fox |
| 5,893,850 A | 4/1999 | Cachia |
| 5,895,390 A | 4/1999 | Moran et al. |
| 5,897,560 A | 4/1999 | Johnson |
| 5,902,302 A | 5/1999 | Berki et al. |
| 5,906,210 A | 5/1999 | Herbert |
| 5,908,422 A | 6/1999 | Bresina |
| 5,908,423 A | 6/1999 | Kashuba et al. |
| 5,912,410 A | 6/1999 | Cordell |
| 5,913,867 A | 6/1999 | Dion |
| 5,919,194 A | 7/1999 | Anderson |
| 5,925,048 A | 7/1999 | Ahmad et al. |
| 5,928,235 A | 7/1999 | Friedl |
| 5,928,240 A | 7/1999 | Johnson |
| 5,928,259 A | 7/1999 | Tovey |
| 5,931,830 A | 8/1999 | Jacobsen et al. |
| 5,931,839 A | 8/1999 | Medoff |
| 5,948,000 A | 9/1999 | Larsen et al. |
| 5,948,001 A | 9/1999 | Larsen |
| 5,951,556 A | 9/1999 | Faccioli et al. |
| 5,951,557 A | 9/1999 | Luter |
| 5,951,561 A | 9/1999 | Pepper et al. |
| 5,954,722 A | 9/1999 | Bono |
| 5,954,728 A | 9/1999 | Heller et al. |
| 5,961,553 A | 10/1999 | Coty et al. |
| 5,964,770 A | 10/1999 | Flomenblit et al. |
| 5,968,047 A | 10/1999 | Reed |
| 5,971,986 A | 10/1999 | Santori et al. |
| 5,976,134 A | 11/1999 | Huebner |
| 5,976,139 A * | 11/1999 | Bramlet ............. A61B 17/1659 606/282 |
| 5,976,147 A | 11/1999 | LaSalle et al. |
| 5,976,188 A | 11/1999 | Dextradeur et al. |
| 5,989,260 A | 11/1999 | Yao |
| 5,989,261 A | 11/1999 | Walker et al. |
| 5,993,459 A | 11/1999 | Larsen et al. |
| 6,004,348 A | 12/1999 | Banas et al. |
| 6,010,505 A | 1/2000 | Asche et al. |
| 6,010,506 A | 1/2000 | Gosney et al. |
| 6,013,081 A | 1/2000 | Burkinshaw et al. |
| 6,015,413 A | 1/2000 | Faccioli et al. |
| 6,017,350 A | 1/2000 | Long |
| 6,018,094 A | 1/2000 | Fox |
| 6,019,761 A | 2/2000 | Gustilo |
| 6,019,762 A | 2/2000 | Cole |
| 6,020,396 A | 2/2000 | Jacobs |
| 6,024,745 A | 2/2000 | Faccioli et al. |
| 6,027,506 A | 2/2000 | Faccioli et al. |
| 6,027,534 A | 2/2000 | Wack et al. |
| 6,033,407 A | 3/2000 | Behrens |
| 6,039,742 A | 3/2000 | Krettek et al. |
| 6,045,556 A | 4/2000 | Cohen |
| 6,053,922 A | 4/2000 | Krause et al. |
| 6,056,756 A | 5/2000 | Eng et al. |
| 6,074,392 A | 6/2000 | Durham |
| 6,077,264 A * | 6/2000 | Chemello ........... A61B 17/7225 606/62 |
| 6,080,159 A | 6/2000 | Vichard |
| 6,083,522 A | 7/2000 | Chu et al. |
| 6,093,209 A | 7/2000 | Sanders |
| 6,096,040 A | 8/2000 | Esser |
| 6,102,911 A | 8/2000 | Faccioli et al. |
| 6,106,528 A | 8/2000 | Durham et al. |
| 6,120,504 A | 9/2000 | Brumback et al. |
| 6,120,509 A | 9/2000 | Wheeler |
| 6,126,661 A | 10/2000 | Faccioli et al. |
| 6,126,691 A | 10/2000 | Kasra et al. |
| 6,127,597 A | 10/2000 | Beyar et al. |
| 6,129,756 A | 10/2000 | Kugler et al. |
| 6,129,762 A | 10/2000 | Li |
| 6,139,583 A | 10/2000 | Johnson |
| 6,143,012 A | 11/2000 | Gausepohl |
| 6,143,033 A | 11/2000 | Paul et al. |
| 6,162,223 A | 12/2000 | Orsak et al. |
| 6,162,226 A | 12/2000 | DeCarlo et al. |
| 6,168,595 B1 | 1/2001 | Durham et al. |
| 6,168,632 B1 | 1/2001 | Moser et al. |
| 6,171,309 B1 | 1/2001 | Huebner |
| 6,176,871 B1 | 1/2001 | Pathak et al. |
| 6,179,839 B1 | 1/2001 | Weiss et al. |
| 6,179,842 B1 | 1/2001 | Spotomo et al. |
| 6,183,470 B1 | 2/2001 | Booth, Jr. et al. |
| 6,197,029 B1 | 3/2001 | Fujimori et al. |
| 6,197,031 B1 | 3/2001 | Barrette et al. |
| 6,200,321 B1 | 3/2001 | Orbay et al. |
| 6,206,880 B1 | 3/2001 | Karladani |
| 6,221,036 B1 | 4/2001 | Lucas |
| 6,221,074 B1 | 4/2001 | Cole et al. |
| 6,224,600 B1 | 5/2001 | Protogirou |
| 6,224,609 B1 | 5/2001 | Ressemann et al. |
| 6,228,123 B1 | 5/2001 | Dezzani |
| 6,231,576 B1 | 5/2001 | Frigg et al. |
| 6,235,029 B1 | 5/2001 | Faccioli et al. |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,261,289 B1 | 7/2001 | Levy |
| 6,270,499 B1 | 8/2001 | Leu et al. |
| 6,273,876 B1 | 8/2001 | Klima et al. |
| 6,273,892 B1 | 8/2001 | Orbay et al. |
| 6,280,456 B1 | 8/2001 | Scribner et al. |
| 6,280,474 B1 | 8/2001 | Cassidy et al. |
| 6,283,969 B1 | 9/2001 | Grusin et al. |
| 6,287,310 B1 | 9/2001 | Fox |
| 6,290,725 B1 | 9/2001 | Weiss et al. |
| 6,296,603 B1 | 10/2001 | Turnlund et al. |
| 6,296,645 B1 | 10/2001 | Hover et al. |
| 6,299,642 B1 | 10/2001 | Chan |
| 6,309,396 B1 | 10/2001 | Ritland |
| 6,319,253 B1 | 11/2001 | Ackeret et al. |
| 6,325,830 B1 | 12/2001 | Mastrorio et al. |
| 6,332,886 B1 | 12/2001 | Green et al. |
| 6,336,929 B1 | 1/2002 | Justin |
| 6,348,053 B1 | 2/2002 | Cachia |
| 6,355,042 B2 | 3/2002 | Winquist et al. |
| 6,355,044 B1 | 3/2002 | Hair |
| 6,355,069 B1 | 3/2002 | DeCarlo et al. |
| 6,358,250 B1 | 3/2002 | Orbay |
| 6,358,283 B1 | 3/2002 | Hogfors et al. |
| 6,364,824 B1 | 4/2002 | Fitzsimmons |
| 6,364,882 B1 | 4/2002 | Orbay |
| 6,364,909 B1 | 4/2002 | McGee |
| 6,379,359 B1 | 4/2002 | Dahners |
| 6,379,360 B1 | 4/2002 | Ackeret et al. |
| 6,383,188 B2 | 5/2002 | Kuslich et al. |
| 6,395,004 B1 | 5/2002 | Dye et al. |
| 6,402,753 B1 | 6/2002 | Cole et al. |
| 6,406,477 B1 | 6/2002 | Fujiwara |
| 6,416,516 B1 | 7/2002 | Stauch et al. |
| 6,423,083 B2 | 7/2002 | Reiley et al. |
| 6,423,096 B1 | 7/2002 | Musset et al. |
| 6,425,923 B1 | 7/2002 | Stalcup et al. |
| 6,436,148 B1 | 8/2002 | DeCarlo, Jr. et al. |
| 6,440,135 B2 | 8/2002 | Orbay et al. |
| 6,443,954 B1 | 9/2002 | Bramlet et al. |
| 6,443,992 B2 | 9/2002 | Lubinus |

(56) References Cited

U.S. PATENT DOCUMENTS

| | | |
|---|---|---|
| 6,447,513 B1 | 9/2002 | Griggs |
| 6,447,514 B1 | 9/2002 | Stalcup et al. |
| 6,447,515 B1 | 9/2002 | Meldrum |
| 6,447,518 B1 | 9/2002 | Krause et al. |
| 6,461,358 B1 | 10/2002 | Faccioli et al. |
| 6,461,360 B1 | 10/2002 | Adam |
| 6,468,278 B1 | 10/2002 | Muckter |
| 6,488,684 B2 | 12/2002 | Sterghos et al. |
| 6,491,694 B1 | 12/2002 | Orsak |
| 6,500,209 B1 | 12/2002 | Kolb |
| 6,508,819 B1 | 1/2003 | Orbay |
| 6,508,820 B2 | 1/2003 | Bales |
| 6,511,481 B1 | 1/2003 | von Hoffmann et al. |
| 6,520,994 B2 | 2/2003 | Nogarin |
| 6,524,313 B1 | 2/2003 | Fassier et al. |
| 6,527,775 B1 | 3/2003 | Warburton |
| 6,530,925 B2 | 3/2003 | Boudard et al. |
| 6,533,788 B1 | 3/2003 | Orbay |
| 6,537,275 B2 | 3/2003 | Venturini et al. |
| 6,540,752 B1 | 4/2003 | Hicken et al. |
| 6,544,265 B2 | 4/2003 | Lieberman |
| 6,551,319 B2 | 4/2003 | Lieberman |
| 6,551,321 B1 | 4/2003 | Burkinshaw et al. |
| 6,554,833 B2 | 4/2003 | Levy et al. |
| 6,554,862 B2 | 4/2003 | Hays et al. |
| 6,558,388 B1 * | 5/2003 | Bartsch ............. A61B 17/7266 606/62 |
| 6,562,042 B2 | 5/2003 | Nelson |
| 6,565,573 B1 | 5/2003 | Ferrante et al. |
| 6,572,620 B1 | 6/2003 | Schon et al. |
| 6,575,973 B1 | 6/2003 | Shekalim |
| 6,575,986 B2 | 6/2003 | Overaker |
| 6,575,994 B1 | 6/2003 | Marin et al. |
| 6,582,453 B1 | 6/2003 | Tran et al. |
| 6,592,578 B2 | 7/2003 | Henniges et al. |
| 6,607,531 B2 | 8/2003 | Frigg |
| 6,613,052 B1 | 9/2003 | Kinnett |
| 6,616,667 B1 | 9/2003 | Steiger et al. |
| 6,616,742 B2 | 9/2003 | Lin et al. |
| 6,620,197 B2 | 9/2003 | Maroney |
| 6,623,487 B1 | 9/2003 | Goshert |
| 6,629,976 B1 | 10/2003 | Gnos et al. |
| 6,632,224 B2 | 10/2003 | Cachia et al. |
| 6,632,235 B2 | 10/2003 | Weikel et al. |
| 6,641,596 B1 | 11/2003 | Uzardi |
| 6,648,889 B2 | 11/2003 | Bramlet et al. |
| 6,648,890 B2 | 11/2003 | Culbert et al. |
| 6,648,893 B2 | 11/2003 | Dudasik |
| 6,652,529 B2 | 11/2003 | Swanson |
| 6,652,591 B2 | 11/2003 | Serbousek et al. |
| 6,656,189 B1 | 12/2003 | Wilson et al. |
| 6,663,647 B2 | 12/2003 | Reiley et al. |
| 6,679,890 B2 | 1/2004 | Margulies et al. |
| 6,682,568 B2 | 1/2004 | Despres, III et al. |
| 6,685,679 B2 | 2/2004 | Merdan |
| 6,685,706 B2 | 2/2004 | Padget et al. |
| 6,688,822 B2 | 2/2004 | Ritter et al. |
| 6,692,530 B2 | 2/2004 | Doubler et al. |
| 6,694,667 B2 | 2/2004 | Davis |
| 6,695,844 B2 | 2/2004 | Bramlet et al. |
| 6,699,251 B1 | 3/2004 | Venturini |
| 6,699,253 B2 | 3/2004 | McDowell et al. |
| 6,706,046 B2 | 3/2004 | Orbay et al. |
| 6,706,072 B2 | 3/2004 | Dwyer et al. |
| 6,709,436 B1 | 3/2004 | Hover et al. |
| 6,712,820 B2 | 3/2004 | Orbay |
| 6,719,793 B2 | 4/2004 | McGee |
| 6,722,368 B1 | 4/2004 | Shaikh |
| 6,723,129 B2 | 4/2004 | Dwyer et al. |
| 6,730,087 B1 | 5/2004 | Butsch |
| 6,730,090 B2 | 5/2004 | Orbay et al. |
| 6,736,818 B2 | 5/2004 | Perren et al. |
| 6,749,611 B2 | 6/2004 | Venturini et al. |
| 6,749,614 B2 | 6/2004 | Teitelbaum et al. |
| 6,755,831 B2 | 6/2004 | Putnam et al. |
| 6,755,862 B2 | 6/2004 | Keynan |
| 6,755,866 B2 | 6/2004 | Southworth |
| 6,767,350 B1 | 7/2004 | Lob |
| 6,767,351 B2 | 7/2004 | Orbay et al. |
| 6,780,185 B2 | 8/2004 | Frei et al. |
| 6,783,529 B2 | 8/2004 | Hover et al. |
| 6,783,530 B1 | 8/2004 | Levy |
| 6,783,533 B2 | 8/2004 | Green et al. |
| 6,786,908 B2 | 9/2004 | Hover et al. |
| 6,790,210 B1 | 9/2004 | Cragg et al. |
| 6,793,655 B2 | 9/2004 | Orsak |
| 6,793,659 B2 | 9/2004 | Putnam |
| 6,808,527 B2 | 10/2004 | Lower et al. |
| 6,821,277 B2 | 11/2004 | Teitelbaum |
| 6,821,299 B2 | 11/2004 | Kirking et al. |
| 6,827,739 B2 | 12/2004 | Griner et al. |
| 6,827,741 B2 | 12/2004 | Reeder |
| 6,840,939 B2 | 1/2005 | Venturini et al. |
| 6,855,146 B2 | 2/2005 | Frigg et al. |
| 6,855,167 B2 | 2/2005 | Shimp et al. |
| 6,863,692 B2 | 3/2005 | Meulink |
| 6,866,455 B2 | 3/2005 | Hasler |
| 6,866,665 B2 | 3/2005 | Orbay |
| 6,875,212 B2 | 4/2005 | Shaolian et al. |
| 6,887,243 B2 | 5/2005 | Culbert |
| 6,887,271 B2 | 5/2005 | Justin et al. |
| 6,887,276 B2 | 5/2005 | Gerbec et al. |
| 6,890,333 B2 | 5/2005 | von Hoffmann et al. |
| 6,893,444 B2 | 5/2005 | Orbay |
| 6,899,713 B2 | 5/2005 | Shaolian et al. |
| 6,899,719 B2 | 5/2005 | Reiley et al. |
| 6,902,583 B2 | 6/2005 | Gerbec et al. |
| 6,908,465 B2 | 6/2005 | von Hoffmann et al. |
| 6,916,323 B2 | 7/2005 | Kitchens |
| 6,921,397 B2 | 7/2005 | Corcoran et al. |
| 6,926,720 B2 | 8/2005 | Castaneda |
| 6,926,741 B2 | 8/2005 | Kolb |
| 6,929,692 B2 | 8/2005 | Tas |
| 6,942,666 B2 | 9/2005 | Overaker et al. |
| 6,942,668 B2 | 9/2005 | Padget et al. |
| 6,949,100 B1 | 9/2005 | Venturini |
| 6,949,124 B2 | 9/2005 | Serbousek et al. |
| 6,951,561 B2 | 10/2005 | Warren et al. |
| 6,974,482 B2 | 12/2005 | Zhu |
| 6,981,981 B2 | 1/2006 | Reiley et al. |
| 6,986,771 B2 | 1/2006 | Paul et al. |
| 6,999,819 B2 | 2/2006 | Swoyer et al. |
| 7,001,386 B2 | 2/2006 | Sohngen et al. |
| 7,001,388 B2 | 2/2006 | Orbay et al. |
| D518,174 S | 3/2006 | Venturini et al. |
| 7,008,425 B2 | 3/2006 | Phillips |
| 7,008,428 B2 | 3/2006 | Cachia et al. |
| 7,008,451 B2 | 3/2006 | Justin et al. |
| 7,011,664 B2 | 3/2006 | Haney et al. |
| 7,012,106 B2 | 3/2006 | Yuan et al. |
| 7,029,476 B2 | 4/2006 | Hansson |
| 7,029,478 B2 | 4/2006 | Hollstien et al. |
| 7,033,363 B2 | 4/2006 | Powell |
| 7,033,365 B2 | 4/2006 | Powell et al. |
| 7,041,104 B1 | 5/2006 | Cole et al. |
| 7,044,978 B2 | 5/2006 | Howie et al. |
| 7,052,498 B2 | 5/2006 | Levy et al. |
| 7,056,322 B2 | 6/2006 | Davison et al. |
| 7,060,075 B2 | 6/2006 | Govari et al. |
| 7,070,601 B2 | 7/2006 | Culbert et al. |
| 7,070,616 B2 | 7/2006 | Majercak et al. |
| 7,074,224 B2 | 7/2006 | Daniels et al. |
| 7,081,119 B2 | 7/2006 | Stihl |
| 7,083,624 B2 | 8/2006 | Irving |
| 7,090,676 B2 | 8/2006 | Huebner et al. |
| 7,097,648 B1 | 8/2006 | Globerman et al. |
| 7,097,664 B2 | 8/2006 | Despres, III et al. |
| RE39,301 E | 9/2006 | Bertin |
| 7,101,376 B2 | 9/2006 | Semet |
| 7,118,574 B2 | 10/2006 | Patel et al. |
| 7,122,056 B2 | 10/2006 | Dwyer et al. |
| 7,137,987 B2 | 11/2006 | Patterson et al. |
| 7,141,052 B2 | 11/2006 | Manderson |
| 7,141,067 B2 | 11/2006 | Jones et al. |

(56) References Cited

U.S. PATENT DOCUMENTS

| | | |
|---|---|---|
| 7,144,399 B2 | 12/2006 | Hayes et al. |
| 7,147,639 B2 | 12/2006 | Berki et al. |
| 7,147,640 B2 | 12/2006 | Huebner et al. |
| 7,153,309 B2 | 12/2006 | Huebner et al. |
| 7,156,852 B2 | 1/2007 | Dye et al. |
| 7,160,302 B2 | 1/2007 | Warburton |
| 7,160,333 B2 | 1/2007 | Plouhar et al. |
| 7,163,563 B2 | 1/2007 | Schwartz et al. |
| 7,175,625 B2 | 2/2007 | Culbert |
| 7,175,631 B2 | 2/2007 | Wilson et al. |
| 7,179,260 B2 | 2/2007 | Gerlach et al. |
| 7,188,687 B2 | 3/2007 | Rudd et al. |
| 7,189,237 B2 | 3/2007 | Huebner |
| 7,632,277 B2 | 12/2009 | Woll et al. |
| 7,846,162 B2 | 12/2010 | Nelson et al. |
| 7,909,825 B2 | 3/2011 | Saravia et al. |
| 7,914,533 B2 | 3/2011 | Nelson et al. |
| 7,942,875 B2 | 5/2011 | Nelson et al. |
| 2001/0011174 A1 | 8/2001 | Reiley et al. |
| 2001/0034526 A1 | 10/2001 | Kuslich et al. |
| 2001/0049531 A1 | 12/2001 | Reiley et al. |
| 2002/0004685 A1 | 1/2002 | White |
| 2002/0029041 A1 | 3/2002 | Hover et al. |
| 2002/0032444 A1 | 3/2002 | Mische |
| 2002/0041896 A1 | 4/2002 | Straub et al. |
| 2002/0068939 A1 | 6/2002 | Levy et al. |
| 2002/0068981 A1 | 6/2002 | Hajianpour |
| 2002/0095214 A1 | 7/2002 | Hyde, Jr. |
| 2002/0099385 A1 | 7/2002 | Ralph et al. |
| 2002/0103488 A1 | 8/2002 | Lower et al. |
| 2002/0143344 A1 | 10/2002 | Taylor |
| 2002/0161369 A1* | 10/2002 | Bramlet ............. A61B 17/7266 606/67 |
| 2002/0165544 A1 | 11/2002 | Perren et al. |
| 2002/0173792 A1 | 11/2002 | Severns et al. |
| 2002/0177866 A1 | 11/2002 | Weikel et al. |
| 2002/0188297 A1 | 12/2002 | Dakin et al. |
| 2002/0198526 A1 | 12/2002 | Shaolian et al. |
| 2003/0032960 A1 | 2/2003 | Dudasik |
| 2003/0040752 A1 | 2/2003 | Kitchens |
| 2003/0045919 A1 | 3/2003 | Swoyer et al. |
| 2003/0073999 A1 | 4/2003 | Putnam |
| 2003/0074075 A1 | 4/2003 | Thomas, Jr. et al. |
| 2003/0078581 A1* | 4/2003 | Frei ..................... A61B 17/746 606/68 |
| 2003/0078669 A1 | 4/2003 | Martin et al. |
| 2003/0097136 A1 | 5/2003 | Hajianpour |
| 2003/0109932 A1 | 6/2003 | Keynan |
| 2003/0130660 A1 | 7/2003 | Levy et al. |
| 2003/0130664 A1 | 7/2003 | Boucher et al. |
| 2003/0139802 A1 | 7/2003 | Wulfman et al. |
| 2003/0181918 A1 | 9/2003 | Smothers et al. |
| 2003/0216738 A1 | 11/2003 | Azar |
| 2003/0236529 A1 | 12/2003 | Shluzas et al. |
| 2004/0006341 A1 | 1/2004 | Shaolian et al. |
| 2004/0010263 A1 | 1/2004 | Boucher et al. |
| 2004/0098017 A1 | 5/2004 | Saab et al. |
| 2004/0098134 A1 | 5/2004 | Meulink |
| 2004/0133204 A1 | 7/2004 | Davies |
| 2004/0133280 A1 | 7/2004 | Trieu |
| 2004/0153114 A1 | 8/2004 | Reiley et al. |
| 2004/0153115 A1 | 8/2004 | Reiley et al. |
| 2004/0167561 A1 | 8/2004 | Boucher et al. |
| 2004/0193255 A1 | 9/2004 | Shanley et al. |
| 2004/0193267 A1 | 9/2004 | Jones et al. |
| 2004/0213825 A1 | 10/2004 | Levy |
| 2004/0214311 A1 | 10/2004 | Levy |
| 2004/0215193 A1 | 10/2004 | Shaolian et al. |
| 2004/0230193 A1 | 11/2004 | Cheung et al. |
| 2004/0236327 A1 | 11/2004 | Paul et al. |
| 2004/0260398 A1 | 12/2004 | Kelman |
| 2004/0267269 A1 | 12/2004 | Middleton et al. |
| 2004/0267271 A9 | 12/2004 | Scribner et al. |
| 2005/0015154 A1 | 1/2005 | Lindsey et al. |
| 2005/0027294 A1 | 2/2005 | Woll et al. |
| 2005/0027301 A1 | 2/2005 | Stihl |
| 2005/0043737 A1 | 2/2005 | Reiley et al. |
| 2005/0043757 A1 | 2/2005 | Arad et al. |
| 2005/0047892 A1 | 3/2005 | Bremner |
| 2005/0055023 A1 | 3/2005 | Sohngen et al. |
| 2005/0055024 A1 | 3/2005 | James et al. |
| 2005/0080425 A1 | 4/2005 | Bhatnagar et al. |
| 2005/0090852 A1 | 4/2005 | Layne et al. |
| 2005/0107883 A1 | 5/2005 | Goodfried et al. |
| 2005/0119662 A1 | 6/2005 | Reiley et al. |
| 2005/0131386 A1 | 6/2005 | Freeman et al. |
| 2005/0143827 A1 | 6/2005 | Globerman et al. |
| 2005/0149022 A1 | 7/2005 | Shaolian et al. |
| 2005/0149024 A1 | 7/2005 | Ferrante et al. |
| 2005/0149025 A1 | 7/2005 | Ferrante et al. |
| 2005/0159749 A1* | 7/2005 | Levy ..................... A61B 17/68 606/62 |
| 2005/0165395 A1 | 7/2005 | Orbay et al. |
| 2005/0171552 A1 | 8/2005 | Johnson et al. |
| 2005/0171563 A1 | 8/2005 | Heinrich et al. |
| 2005/0177158 A1 | 8/2005 | Doubler et al. |
| 2005/0203510 A1 | 9/2005 | Sohngen et al. |
| 2005/0209595 A1 | 9/2005 | Karmon |
| 2005/0216007 A1 | 9/2005 | Woll et al. |
| 2005/0228391 A1 | 10/2005 | Levy et al. |
| 2005/0234453 A1 | 10/2005 | Shaolian et al. |
| 2005/0234559 A1 | 10/2005 | Fernandez et al. |
| 2005/0251140 A1 | 11/2005 | Shaolian et al. |
| 2005/0261781 A1 | 11/2005 | Sennett et al. |
| 2005/0267481 A1 | 12/2005 | Carl et al. |
| 2005/0267483 A1 | 12/2005 | Middleton |
| 2005/0267586 A1 | 12/2005 | Sidebotham |
| 2005/0283250 A1 | 12/2005 | Coon et al. |
| 2005/0288678 A1 | 12/2005 | Reilley et al. |
| 2006/0004465 A1 | 1/2006 | Bergin et al. |
| 2006/0015101 A1 | 1/2006 | Warburton et al. |
| 2006/0015123 A1 | 1/2006 | Fencl et al. |
| 2006/0030945 A1 | 2/2006 | Wright |
| 2006/0036248 A1 | 2/2006 | Ferrante |
| 2006/0052788 A1 | 3/2006 | Thelen et al. |
| 2006/0064094 A1 | 3/2006 | Levy et al. |
| 2006/0084997 A1 | 4/2006 | Dejardin |
| 2006/0084998 A1 | 4/2006 | Levy et al. |
| 2006/0122601 A1 | 6/2006 | Tandon |
| 2006/0200143 A1 | 9/2006 | Warburton |
| 2006/0200144 A1 | 9/2006 | Warburton |
| 2006/0229617 A1 | 10/2006 | Meller et al. |
| 2006/0247638 A1 | 11/2006 | Trieu et al. |
| 2006/0264950 A1* | 11/2006 | Nelson ............... A61B 17/7208 606/916 |
| 2006/0264951 A1 | 11/2006 | Nelson et al. |
| 2007/0123878 A1 | 5/2007 | Shaver et al. |
| 2007/0142916 A1 | 6/2007 | Olson et al. |
| 2007/0260257 A1 | 11/2007 | Phan |
| 2008/0077154 A1 | 3/2008 | Edwards et al. |
| 2008/0132896 A1 | 6/2008 | Bowen et al. |
| 2008/0140078 A1 | 6/2008 | Nelson et al. |
| 2008/0149115 A1 | 6/2008 | Hauck et al. |
| 2008/0221620 A1 | 9/2008 | Krause et al. |
| 2008/0234678 A1 | 9/2008 | Gutierrez et al. |
| 2008/0243132 A1 | 10/2008 | Tipirneni et al. |
| 2008/0255560 A1 | 10/2008 | Myers et al. |
| 2008/0262495 A1* | 10/2008 | Coati ................ A61B 17/7266 606/62 |
| 2008/0269745 A1 | 10/2008 | Justin |
| 2008/0269751 A1 | 10/2008 | Matityahu |
| 2008/0287951 A1 | 11/2008 | Stoneburner et al. |
| 2009/0018542 A1 | 1/2009 | Saravia et al. |
| 2009/0182336 A1 | 7/2009 | Brenzel et al. |
| 2009/0187116 A1 | 7/2009 | Noishiki et al. |
| 2009/0228007 A1 | 9/2009 | Justin et al. |
| 2009/0228008 A1 | 9/2009 | Justin et al. |
| 2010/0023010 A1 | 1/2010 | Nelson et al. |
| 2010/0094347 A1 | 4/2010 | Nelson et al. |
| 2011/0087227 A1 | 4/2011 | Mazur et al. |
| 2011/0144645 A1 | 6/2011 | Saravia et al. |
| 2011/0178520 A1 | 7/2011 | Taylor et al. |
| 2011/0190832 A1 | 8/2011 | Taylor et al. |

(56) References Cited

U.S. PATENT DOCUMENTS

| | | |
|---|---|---|
| 2011/0218585 A1 | 9/2011 | Krinke et al. |
| 2011/0218626 A1 | 9/2011 | Krinke et al. |
| 2011/0282346 A1 | 11/2011 | Pham et al. |

FOREIGN PATENT DOCUMENTS

| | | |
|---|---|---|
| EP | 1815813 A2 | 8/2007 |
| WO | WO 97/18769 | 5/1997 |
| WO | WO 98/27876 | 7/1998 |
| WO | WO 98/56301 | 12/1998 |
| WO | WO 99/20195 | 4/1999 |
| WO | WO 00/28906 | 5/2000 |
| WO | WO 01/28443 | 4/2001 |
| WO | WO 02/00270 | 1/2002 |
| WO | WO 02/00275 | 1/2002 |
| WO | WO 02/02158 | 1/2002 |
| WO | WO 2005/112804 | 12/2005 |
| WO | WO 2006/053210 | 5/2006 |
| WO | WO 2006/124764 | 11/2006 |
| WO | WO 2007/009123 | 1/2007 |

OTHER PUBLICATIONS

Andermahr et al., "Anatomy of the clavicle and the intramedullary nailing of midclavicular fractures," Clinical Anatomy, vol. 20; pp. 48-56; 2007.

The Titanium Flexible Humeral Nail System (Technique Guide), Synthes, 1999.

* cited by examiner

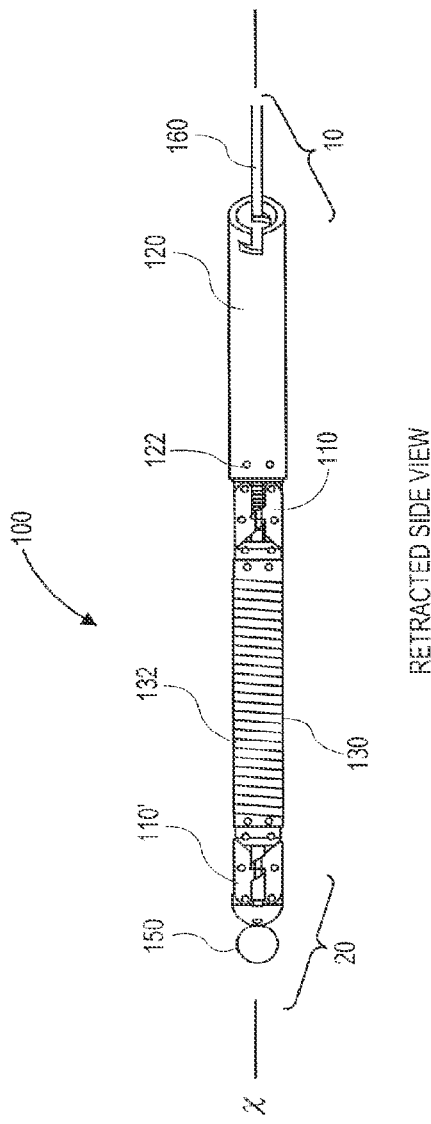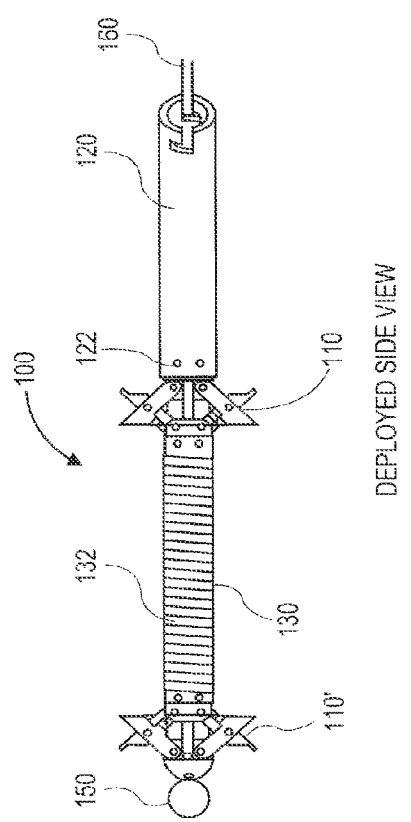

DEPLOYED ISO

EXPLODED ASSEMBLY

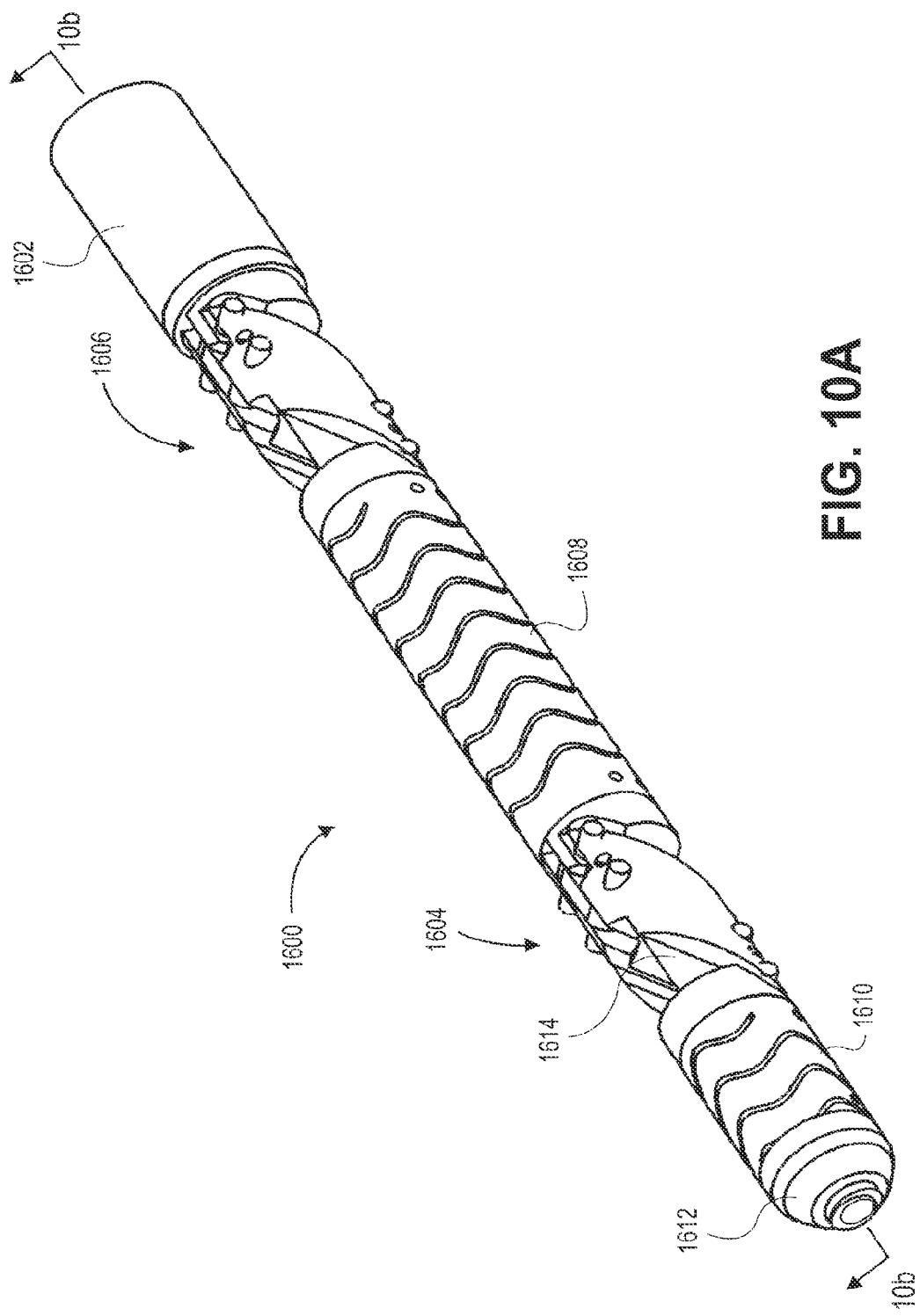

Helical-Wavy cut.

90° TYP CUT ANGLE

Helical cut

Side view of outrigger device

FRACTURE FIXATION DEVICE, TOOLS AND METHODS

CROSS-REFERENCE TO RELATED APPLICATIONS

This application is a continuation of U.S. application Ser. No. 13/032,437 filed on Feb. 22, 2011, which is a continuation of U.S. application Ser. No 11/944,366 filed Nov. 21, 2007, now U.S. Pat. No. 7,909,825 issued on Mar. 22, 2011, which claims the benefit under 35 U.S.C. §119 of the following U.S. Provisional Applications, the disclosures of which are incorporated herein by reference: U.S. Application No. 60/867,011 filed Nov. 22, 2006; U.S. Ser. No. 60/866,976 filed Nov. 22, 2006; and U.S. Application No. 60/949,071 filed Jul. 11, 2007. Any and all priority claims identified in the Application Data Sheet, or any correction thereto, are hereby incorporated by reference under 37 CFR 1.57.

All publications and patent applications mentioned in this specification are herein incorporated by reference to the same extent as if each individual publication or patent application was specifically and individually indicated to be incorporated by reference.

BACKGROUND

Embodiments of the present invention relate to methods and systems for providing reinforcement of bones. More specifically, the present invention relates to methods and systems for providing reconstructive surgical procedures and devices for reconstruction and reinforcement bones, including diseased, osteoporotic and fractured bones.

1. Field of the Invention

Bone fractures are a common medical condition both in the young and old segments of the population. However, with an increasingly aging population, osteoporosis has become more of a significant medical concern in part due to the risk of osteoporotic fractures. Osteoporosis and osteoarthritis are among the most common conditions to affect the musculoskeletal system, as well as frequent causes of locomotor pain and disability. Osteoporosis can occur in both human and animal subjects (e.g. horses). Osteoporosis (OP) and osteoarthritis (OA) occur in a substantial portion of the human population over the age of fifty. The National Osteoporosis Foundation estimates that as many as 44 million Americans are affected by osteoporosis and low bone mass, leading to fractures in more than 300,000 people over the age of 65. In 1997 the estimated cost for osteoporosis related fractures was $13 billion. That figure increased to $17 billion in 2002 and is projected to increase to $210-240 billion by 2040. Currently it is expected that one in two women, and one in four men, over the age of 50 will suffer an osteoporosis-related fracture. Osteoporosis is the most important underlying cause of fracture in the elderly. Also, sports and work-related accidents account for a significant number of bone fractures seen in emergency rooms among all age groups.

2. Description of the Related Art

One current treatment of bone fractures includes surgically resetting the fractured bone. After the surgical procedure, the fractured area of the body (i.e., where the fractured bone is located) is often placed in an external cast for an extended period of time to ensure that the fractured bone heals properly. This can take several months for the bone to heal and for the patient to remove the cast before resuming normal activities.

In some instances, an intramedullary (IM) rod or nail is used to align and stabilize the fracture. In that instance, a metal rod is placed inside a canal of a bone and fixed in place, typically at both ends. See, for example, Fixion™ IM (Nail), www.disc-o-tech.com. This approach requires incision, access to the canal, and placement of the IM nail. The nail can be subsequently removed or left in place. A conventional IM nail procedure requires a similar, but possibly larger, opening to the space, a long metallic nail being placed across the fracture, and either subsequent removal, and or when the nail is not removed, a long term implant of the IM nail. The outer diameter of the IM nail must be selected for the minimum inside diameter of the space. Therefore, portions of the IM nail may not be in contact with the canal. Further, micromotion between the bone and the IM nail may cause pain or necrosis of the bone. In still other cases, infection can occur. The IM nail may be removed after the fracture has healed. This requires a subsequent surgery with all of the complications and risks of a later intrusive procedure.

External fixation is another technique employed to repair fractures. In this approach, a rod may traverse the fracture site outside of the epidermis. The rod is attached to the bone with trans-dermal screws. If external fixation is used, the patient will have multiple incisions, screws, and trans-dermal infection paths. Furthermore, the external fixation is cosmetically intrusive, bulky, and prone to painful inadvertent manipulation by environmental conditions such as, for example, bumping into objects and laying on the device.

Other concepts relating to bone repair are disclosed in, for example, U.S. Pat. No. 5,108,404 to Scholten for Surgical Protocol for Fixation of Bone Using Inflatable Device; U.S. Pat. No. 4,453,539 to Raftopoulos et al. for Expandable Intramedullary Nail for the Fixation of Bone Fractures; U.S. Pat. No. 4,854,312 to Raftopolous for Expanding Nail; U.S. Pat. No. 4,932,969 to Frey et al. for Joint Endoprosthesis; U.S. Pat. No. 5,571,189 to Kuslich for Expandable Fabric Implant for Stabilizing the Spinal Motion Segment; U.S. Pat. No. 4,522,200 to Stednitz for Adjustable Rod; U.S. Pat. No. 4,204,531 to Aginsky for Nail with Expanding Mechanism; U.S. Pat. No. 5,480,400 to Berger for Method and Device for Internal Fixation of Bone Fractures; U.S. Pat. No. 5,102,413 to Poddar for Inflatable Bone Fixation Device; U.S. Pat. No. 5,303,718 to Krajicek for Method and Device for the Osteosynthesis of Bones; U.S. Pat. No. 6,358,283 to Hogfors et al. for Implantable Device for Lengthening and Correcting Malpositions of Skeletal Bones; U.S. Pat. No. 6,127,597 to Beyar et al. for Systems for Percutaneous Bone and Spinal Stabilization, Fixation and Repair; U.S. Pat. No. 6,527,775 to Warburton for Interlocking Fixation Device for the Distal Radius; U.S. Patent Publication US2006/0084998 A1 to Levy et al. for Expandable Orthopedic Device; and PCT Publication WO 2005/112804 A1 to Myers Surgical Solutions, LLC for Fracture Fixation and Site Stabilization System. Other fracture fixation devices, and tools for deploying fracture fixation devices, have been described in: US Patent Appl. Publ. No. 2006/0254950; U.S. Ser. No. 60/867,011 (filed Nov. 22, 2006); U.S. Ser. No. 60/866,976 (filed Nov. 22, 2006); and U.S. Ser. No. 60/866,920 (filed Nov. 22, 2006).

In view of the foregoing, it would be desirable to have a device, system and method for providing effective and minimally invasive bone reinforcement and fracture fixation to treat fractured or diseased bones.

SUMMARY OF THE INVENTION

Aspects of the invention relate to embodiments of a bone fixation device and to methods for using such a device for repairing a bone fracture. The bone fixation device may include an elongate body with a longitudinal axis and having a flexible state and a rigid state. The device further may include a plurality of grippers disposed at longitudinally-spaced locations along the elongated body, a curved rigid hub connected to the elongated body, and an actuator that is operably-connected to the grippers to deploy the grippers from a first shape to an expanded second shape.

With regard to the actuator, in some embodiments of the bone fixation device, the actuator is operably connected to the elongate body in order to change the elongate body from its flexible state (such as for insertion into the bone through a curved access port) to its rigid state (such as to rigidly hold to the substantially straight bone shaft). In some embodiments, the actuator is operably connected to a first gripper that is disposed at the proximal end of the elongate body and to a second gripper that is disposed at the distal end of the elongate body so as to be able to expand the first and second grippers simultaneously.

With further regard to the actuator of the device, the actuator may include a ratchet that permits movement of the actuator only in a deployment direction, and in some of these embodiments, the device may include a ratchet release. With still further regard to the actuator, in some embodiments the actuator may be threaded, and in some embodiments, the actuator may be rotatable with respect to the grippers.

With regard to the shape of the grippers of the device, in some embodiments, the second shape of at least one gripper is shorter along the longitudinal axis in its expanded second shape than it is in its first shape.

With regard to one of the plurality of grippers of the device, in some embodiments a first gripper includes an element that pivots away from longitudinal axis of the elongated body when the first gripper is deployed from the first shape to the second shape. In various of these pivoting element-including embodiments, the first gripper may include two sets or three sets of oppositely disposed pivoting elements at the same axial location of the elongate body, the pivoting elements being adapted to pivot away from longitudinal axis of the elongated body when the first gripper is deployed from the first shape to the second shape.

In some of the embodiments with a gripper that includes a pivoting element, a first gripper may include a pair of pivoting elements disposed on opposite sides of the elongate body at the same axial position of the elongate body. In various of embodiments that include a gripper with a pair of pivoting elements, the pair of pivoting elements may be connected to the elongate body so as to rotate either in the same direction or in opposite directions when the first gripper is deployed from the first shape to the second shape. In some embodiments with a gripper that includes a pivoting element, the element may include either one or two bone-engaging surfaces that pivot radially outward from the elongate body.

With regard to the curved hub of the device, in some embodiments, the curved hub includes screw holes that may be pre-drilled and pre-tapped, and some embodiments the hub may include a drill alignment tool interface to drill the screw holes during surgery.

With regard to a method for using embodiments of the bone fixation device, as summarized above, to repair a fractured bone, the method includes inserting a bone fixation device into an intramedullary space of the bone, placing at least a portion of an elongate body of the fixation device in a flexible state on one side of the fracture and at least a portion of a curved rigid hub on another side of the fracture, and operating an actuator to deploy a plurality of grippers of the fixation device to engage an inner surface of the intramedullary space to anchor the fixation device to the bone.

In some method embodiments, the method further includes rigidizing the elongate body after the inserting step, and in some of these embodiments, the rigidizing step includes operating the actuator.

With regard to the operating step of the method, some embodiments include shortening one of the grippers.

With further regard to the operating step of the method, some embodiments include pivoting a pivotable gripper element away from the longitudinal axis of the elongate body. In some embodiments, at least two pivotable gripper elements are pivoted away from a longitudinal axis of the elongate body, the pivotable gripper elements being disposed at different axial locations on the elongate body. In some embodiments, the pivoting step includes moving two bone engaging surfaces of the pivotable gripper element into engagement with the bone. In some embodiments of the method, the pivoting step includes moving either two or three sets of pivotable gripper elements away from the longitudinal axis of the elongate body, the two sets being disposed on opposite sides of the elongate body at the same axial position. In some embodiments of the method, the pivoting step includes pivoting a pair of pivoting elements disposed on opposite sides of the elongate body at the same axial position so that two surfaces of each pivoting element engage the inner surface of the intramedullary space. In some embodiments of the method, the pivoting step includes rotating the pivoting elements in the same or in respectively opposite directions.

With still further regard to the operating step of the method and the actuator, some embodiments include moving the actuator longitudinally with respect to the fixation device. In some of these embodiments, the method further includes engaging a ratchet with the actuator to permit movement of the actuator only in a deployment direction, and in some of these embodiments, the method may further include disengaging the ratchet such as for removal of the device. With still further regard to the method's operating step and the actuator, some embodiments may include rotating the actuator with respect to the fixation device.

Some embodiments of the method further includes inserting a screw through the bone and the hub. These particular embodiments may further include forming a hole through the bone and the hub prior to inserting the screw. In some embodiments that include the step of inserting a screw through the bone and the hub, the step may include inserting a fixation device having a curved hub with a preformed hole, the step of inserting a screw by way of this embodiment thereby including inserting a screw through the bone and the preformed hole. In some of these latter embodiments, the curved hub has a plurality of preformed holes, the method then including inserting a first screw dorsal to volar through two portions of the bone and a first and second of the preformed holes and inserting a second screw volar to dorsal through two other portions of the bone and a third and fourth of the preformed holes. In some of these latter embodiments, the method may further include inserting a third screw proximal to distal through two more portions of the bone and a fifth and sixth of the preformed holes of the hub. In still further embodiments of the method that include the step of inserting a screw through the bone and the hub, the method may further include attaching a drill alignment guide to the hub and aligning a drill bit with the hub using the drill alignment guide.

One embodiment of the present invention provides a low weight to volume mechanical support for fixation, reinforcement and reconstruction of bone or other regions of the musculo-skeletal system in both humans and animals. The method of delivery of the device is another aspect of the invention. The method of delivery of the device in accordance with the various embodiments of the invention reduces the trauma created during surgery, decreasing the risks associated with infection and thereby decreasing the recuperation time of the patient. The framework may in one embodiment include an expandable and contractible structure to permit re-placement and removal of the reinforcement structure or framework.

In accordance with the various embodiments of the present invention, the mechanical supporting framework or device may be made from a variety of materials such as metal, composite, plastic or amorphous materials, which include, but are not limited to, steel, stainless steel, cobalt chromium plated steel, titanium, nickel titanium alloy (nitinol), super-elastic alloy, and polymethylmethacrylate (PMMA). The supporting framework or device may also include other polymeric materials that are biocompatible and provide mechanical strength, that include polymeric material with ability to carry and delivery therapeutic agents, that include bioabsorbable properties, as well as composite materials and composite materials of titanium and polyetheretherketone (PEEK™) composite materials of polymers and minerals, composite materials of polymers and glass fibers, composite materials of metal, polymer, and minerals.

Within the scope of the present invention, each of the aforementioned types of device may further be coated with proteins from synthetic or animal source, or include collagen coated structures, and radioactive or brachytherapy materials. Furthermore, the construction of the supporting framework or device may include radio-opaque markers or components that assist in their location during and after placement in the bone or other region of the musculo-skeletal systems.

Further, the reinforcement device may, in one embodiment, be osteo incorporating, such that the reinforcement device may be integrated into the bone.

In a further embodiment, there is provided a low weight to volume mechanical supporting framework or device deployed in conjunction with other suitable materials to form a composite structure in-situ. Examples of such suitable materials may include, but are not limited to, bone cement, high density polyethylene, Kapton®, polyetheretherketone (PEEK™), and other engineering polymers.

Once deployed, the supporting framework or device may be electrically, thermally, or mechanically passive or active at the deployed site within the body. Thus, for example, where the supporting framework or device includes nitinol, the shape of the device may be dynamically modified using thermal, electrical or mechanical manipulation. For example, the nitinol device or supporting framework may be expanded or contracted once deployed, to move the bone or other region of the musculo-skeletal system or area of the anatomy by using one or more of thermal, electrical or mechanical approaches.

An embodiment of the invention includes a lockable bone fixation device comprising: a rigidizable flexible body adapted to be positioned in a space formed in a bone; a guide wire adapted to guide movement of the body; and an actuable lock adapted to secure the body within the space of the bone from an end of the device. The body can be configured to be flexible, have apertures, be expandable and/or be bioabsorbable. Further, the body can be removable from the space within the bone, if desired. The device is adapted and configured to access the space within the bone through an access aperture formed in a bony protuberance of the bone. In a further embodiment, a second body can be provided that is adapted to fit within the first body. The anchors, e.g., teeth or interdigitation process, are adapted to engage bone. In still another embodiment of the invention, a cantilever adapted to retain the lockable bone fixation device within the space. In still another embodiment, the device is adapted to be delivered by a catheter. In yet another embodiment, the distal end of the device is adapted to provide an obsturator surface. In still another embodiment of the device, the distal end of the device is configured to provide a guiding tip. In yet another embodiment of the device, the device is adapted to receive external stimulation to provide therapy to the bone. In still another embodiment of the device, the device is adapted to receive composite material when the device is disposed within a lumen or opening within the body or bone.

In still another embodiment of the invention, a method of repairing a bone fracture is disclosed that comprises: accessing a fracture along a length of a bone through a bony protuberance at an access point at an end of a bone; advancing a bone fixation device into a space through the access point at the end of the bone; bending a portion of the bone fixation device along its length to traverse the fracture; and locking the bone fixation device into place within the space of the bone. The method can also include the step of advancing an obsturator through the bony protuberance and across the fracture prior to advancing the bone fixation device into the space. In yet another embodiment of the method, the step of anchoring the bone fixation device within the space can be included. In still another embodiment of the method, a first sleeve and a second sleeve of the bone fixation device can be engaged to expand an anchor into the bone.

An aspect of the invention discloses a removable bone fixation device that uses a single port of insertion and has a single-end of remote actuation wherein a bone fixation device stabilizes bone. The bone fixation device is adapted to provide a single end in one area or location where the device initiates interaction with bone. The device can be deployed such that the device interacts with bone. Single portal insertion and single-end remote actuation enables the surgeon to insert and deploy the device, deactivate and remove the device, reduce bone fractures, displace bone, and lock the device in place. In addition, the single-end actuation enables the device to grip bone, compresses the rigidizable flexible body, permits axial, torsional and angular adjustments to its position during surgery, and releases the device from the bone during its removal procedure. A removable extractor can be provided in some embodiments of the device to enable the device to be placed and extracted by deployment and remote actuation from a single end. The device of the invention can be adapted and configured to provide at least one rigidizable flexible body or sleeve. Further the body can be configured to be flexible in all angles and directions. The flexibility provided is in selective planes and angles in the Cartesian, polar, or cylindrical coordinate systems. Further, in some embodiments, the body is configured to have a remote actuation at a single end. Additionally, the body can be configured to have apertures, windings, etc. Another aspect of the invention includes a bone fixation device in that has mechanical geometry that interacts with bone by a change in the size of at least one dimension of a Cartesian, polar, or spherical coordinate system. Further, in some embodiments, bioabsorbable materials can be used in conjunction with the devices, for example by providing specific subcomponents of the device configured from bioabsorbable materials. A sleeve can be provided in some embodiments where the sleeve is removable, has deployment, remote actuation, and a single end. Where a sleeve is employed, the sleeve can be adapted to provide a deployable interdigitation process or to provide an aperture along its length through which the deployable interdigitation process is adapted to engage bone. In some embodiments, the deployable interdigitation process is further adapted to engage bone when actuated by the sleeve. In some embodiments, the bone fixation device further comprises a cantilever adapted to retain the deployable bone fixation device within the space. The sleeve can further be adapted to be expanded and collapsed within the space by a user. One end of the device can be configured to provide a blunt obsturator surface adapted to advance into the bone. A guiding tip may also be provided that facilitates guiding the device through the bone. Further, the deployable bone fixation device can be adapted to receive external stimulation to provide therapy to the bone. The device can further be adapted to provide an integral stimulator which provides therapy to the bone. In still other embodiments, the device can be adapted to receive deliver therapeutic stimulation to the bone.

The invention also includes a method for repairing a bone fracture comprising: accessing a fracture along a length of bone through a bony protuberance at an entry portal; introducing the bone fixation device into the medullary canal through the entry portal; bending the bone fixation device along its length to advance into the medullary space in the bone; bending the bone fixation device along its length to traverse the fracture site; placing a flexible elbow in the medullary canal at the fracture site; stiffening the bone fixation device; locking the bone fixation device to the bone; reducing the fracture with the bone fixation device in place in the medullary canal; locking the flexible elbow to achieve intramedullary reduction of the fracture. The method can further include the step of introducing a guide wire into the medullary space through a bony protuberance at an entry portal. Additionally, the guide wire can be reamed through the bony protuberance at an entry portal. The location of the reamed bony canal can be determined by the fracture anatomy and bone anatomy. In some embodiments of the method, a sleeve can be advanced along the bone fixation device. In such embodiments, the sleeve can function to unlock the spikes from the fixation device. Once the spikes are unlocked from the fixation device, the spikes then fix the device to the bone. Locking rings can also be employed to lock the device to the bone. The rings can be locked to the fixation device in some embodiments. Additionally, the rings can be threaded over the device. In other embodiments, a guide jig guides screws through the rings. Further self tapping screws lock the rings to the bone and bone fixation device. A set screw can also be used to lock the device at the fracture site. The device can also be stiffened. In performing the method of the invention, fracture fragments can be reduced.

The devices disclosed herein may be employed in various regions of the body, including: cranial, thoracic, lower extremities and upper extremities. Additionally, the devices are suitable for a variety of breaks including, metaphyseal and diaphyseal.

The fracture fixation devices of various embodiments of the invention are adapted to be inserted through an opening of a fractured bone, such as the radius (e.g., through a bony protuberance on a distal or proximal end or through the midshaft) into the intramedullary canal of the bone. In some embodiments, the fixation device has two main components, one configured component for being disposed on the side of the fracture closest to the opening and one component configured for being disposed on the other side of the fracture from the opening so that the fixation device traverses the fracture.

The device components cooperate to align, fix and/or reduce the fracture so as to promote healing. The device may be removed from the bone after insertion (e.g., after the fracture has healed or for other reasons), or it may be left in the bone for an extended period of time or permanently.

In some embodiments, the fracture fixation device has one or more actuatable anchors or grippers on its proximal and/or distal ends. These anchors may be used to hold the fixation device to the bone while the bone heals.

In some embodiments, to aid in insertion into the intramedullary canal, at least one component of the fracture fixation device has a substantially flexible state and a substantially rigid state. Once in place, deployment of the device also causes the components to change from the flexible state to a rigid state to aid in proper fixation of the fracture. At least one of the components may be substantially rigid or semi-flexible. At least one component may provide a bone screw attachment site for the fixation device.

Embodiments of the invention also provide deployment tools with a tool guide for precise alignment of one or more bone screws with the fracture fixation device. These embodiments also provide bone screw orientation flexibility so that the clinician can select an orientation for the bone screw(s) that will engage the fixation device as well as any desired bone fragments or other bone or tissue locations.

The deployment tools also have features that help make it easier to use. For example, deployment tool components can be oriented so as to be used by either the right hand or the left hand of the user. Also, certain deployment tool components may be rotated out of the user's field of vision during use without compromising the component's function.

These and other features and advantages of the present invention will be understood upon consideration of the following detailed description of the invention and the accompanying drawings.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 1A-E are views of an embodiment of a bone repair device according to the invention.

FIG. 10A is a perspective view showing another embodiment of a bone repair device in a retracted state.

FIG. 10B is a cross-sectional view taken along line 10b-10b in FIG. 10a.

FIG. 11B is a cross-sectional view taken along line 11b-11b in FIG. 11a.

DETAILED DESCRIPTION

Figure 1C:
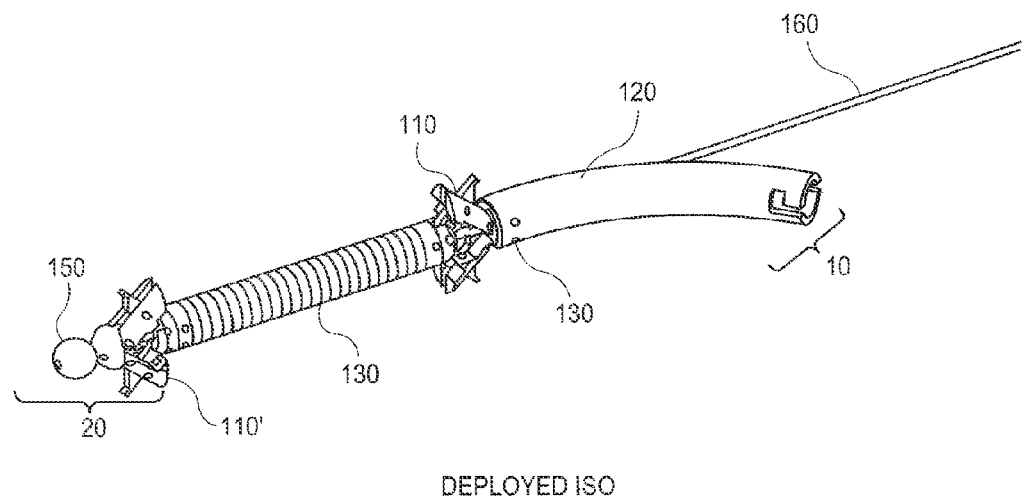
Figure 1D:
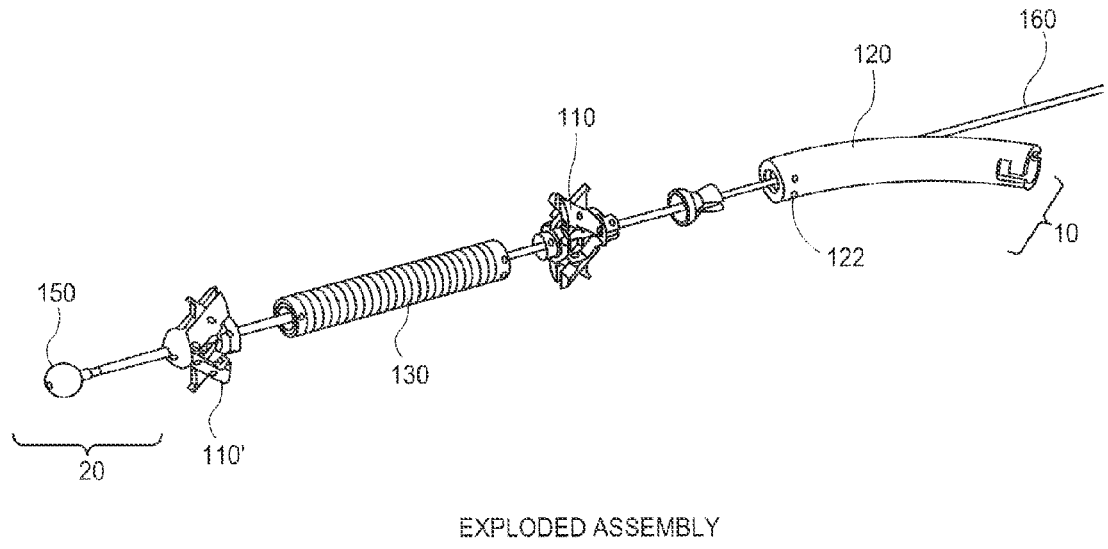
Figure 1E:
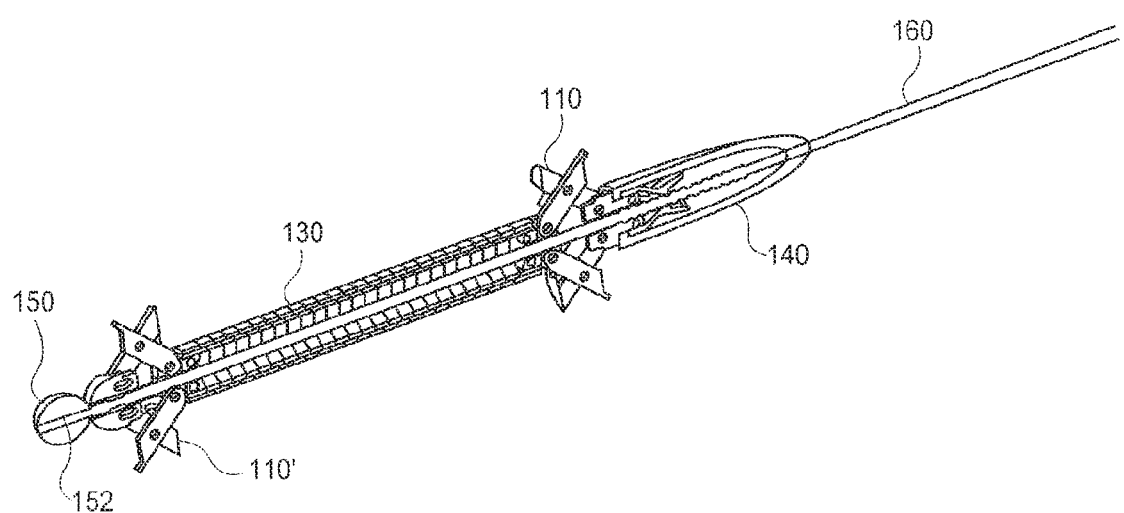
Figure 2A:
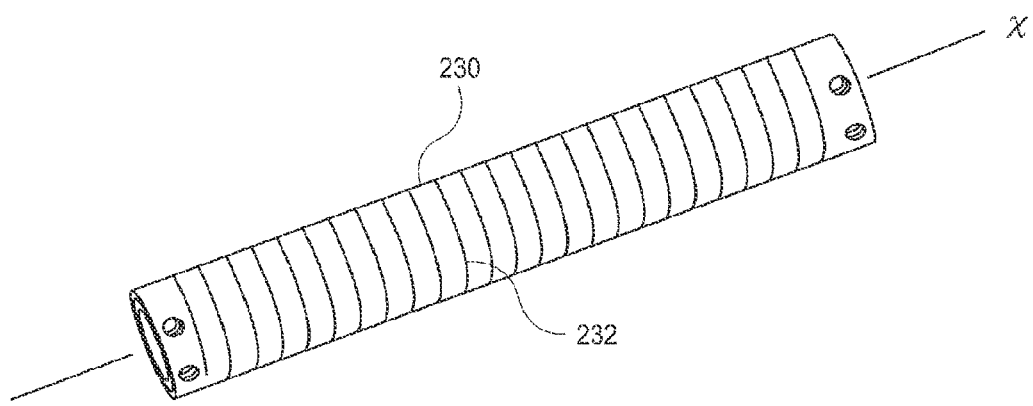
FIGS. 2A-D are views of flexible-to-rigid bodies.
Figure 2B:
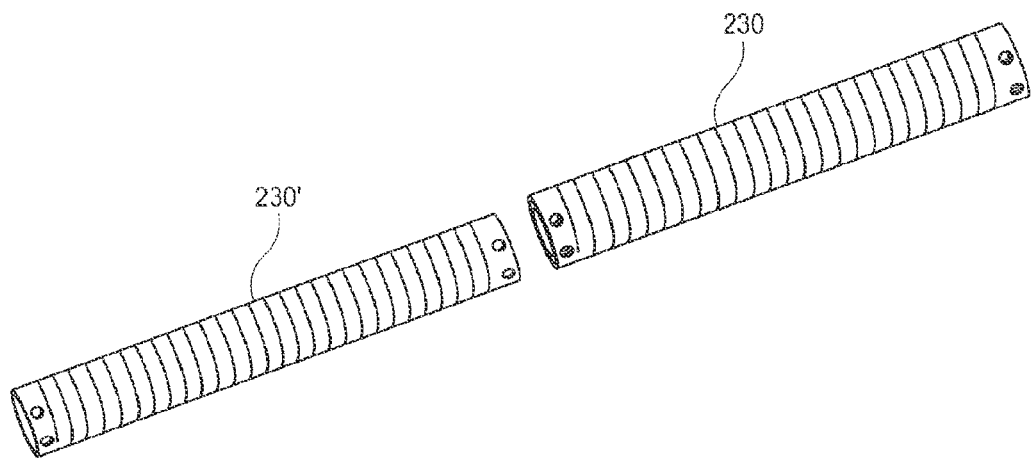
Figure 2C:
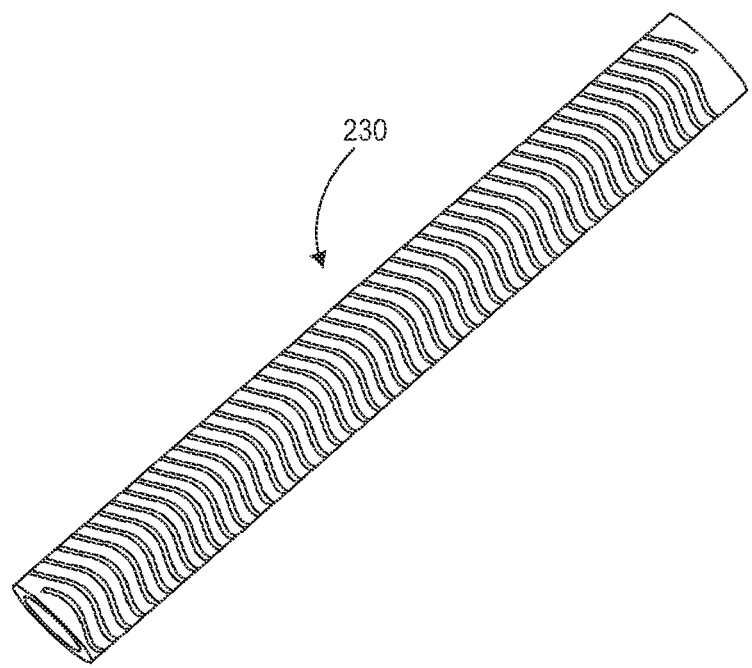
Figure 2D:
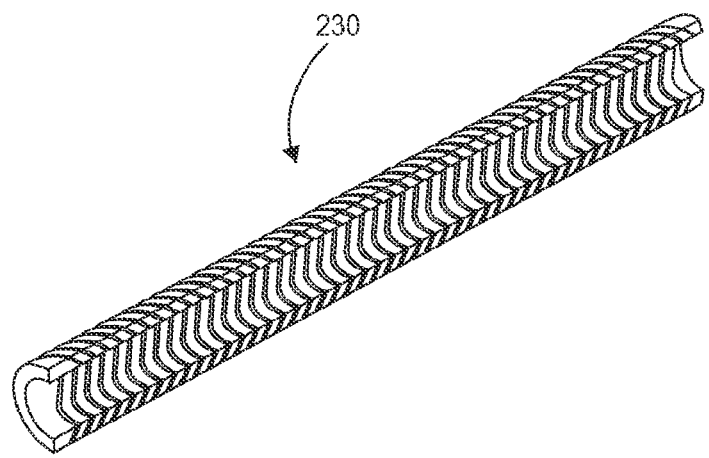

By way of background and to provide context for the invention, it may be useful to understand that bone is often described as a specialized connective tissue that serves three major functions anatomically. First, bone provides a mechanical function by providing structure and muscular attachment for movement. Second, bone provides a metabolic function by providing a reserve for calcium and phosphate. Finally, bone provides a protective function by enclosing bone marrow and vital organs. Bones can be categorized as long bones (e.g. radius, femur, tibia and humerus) and flat bones (e.g. skull, scapula and mandible). Each bone type has a different embryological template. Further each bone type contains cortical and trabecular bone in varying proportions. The devices of this invention can be adapted for use in any of the bones of the body as will be appreciated by those skilled in the art.

Cortical bone (compact) forms the shaft, or diaphysis, of long bones and the outer shell of flat bones. The cortical bone provides the main mechanical and protective function. The trabecular bone (cancellous) is found at the end of the long bones, or the epiphysis, and inside the cortex of flat bones. The trabecular bone consists of a network of interconnecting trabecular plates and rods and is the major site of bone remodeling and resorption for mineral homeostasis. During development, the zone of growth between the epiphysis and diaphysis is the metaphysis. Finally, woven bone, which lacks the organized structure of cortical or cancellous bone, is the first bone laid down during fracture repair. Once a bone is fractured, the bone segments are positioned in proximity to each other in a manner that enables woven bone to be laid down on the surface of the fracture. This description of anatomy and physiology is provided in order to facilitate an understanding of the invention. Persons of skill in the art will also appreciate that the scope and nature of the invention is not limited by the anatomy discussion provided. Further, it will be appreciated there can be variations in anatomical characteristics of an individual patient, as a result of a variety of factors, which are not described herein. Further, it will be appreciated there can be variations in anatomical characteristics between bones which are not described herein.

FIGS. 1a-e are views of an embodiment of a bone repair device 100 having a proximal end 10 (nearest the surgeon) and a distal end 20 (further from surgeon) and positioned within the bone space of a patient) according to the invention. In the retracted side view shown in FIG. 1a. the device sits along a longitudinal axis x. The devices 100 can contain a plate, nail/plate combination, or a blade/plate combination and can be made from alloys, such as cobalt-chromium molybdenum, stainless steel and titanium, or plastics such as UHMWPE, PEEK or PEKK. The proximal end and distal end, as used in this context, refers to the position of an end of the device relative to the remainder of the device or the opposing end as it appears in the drawing. The proximal end can be used to refer to the end manipulated by the user or physician. The proximal end may be configured such that a portion thereof remains outside the bone. Alternatively, the proximal end is configured such that it does not remain outside the bone. The distal end, thus, can be used to refer to the end of the device that is inserted and advanced within the bone and is furthest away from the physician. As will be appreciated by those skilled in the art, the use of proximal and distal could change in another context, e.g. the anatomical context in which proximal and distal use the patient as reference.

When implanted within a patient, the device can be held in place with suitable fasteners such as wire, screws, nails, bolts, nuts and washers. The device 100 is used for fixation of fractures of the proximal or distal end of long bones such as intracapsular, intertrochanteric, intercervical, supracondular, or condular fractures of the femur; for fusion of a joint; or for surgical procedures that involve cutting a bone. The devices 100 may be implanted or attached through the skin so that a pulling force (traction may be applied to the skeletal system).

Turning now to FIG. 1b. the design of this radius metaphyseal repair device depicted is adapted to provide a scissor-like engaging mechanism adapted to engage target bone of a patient from the inside of the bone. As configured for this anatomical application, the device is designed to facilitate bone healing when placed in the intramedullary space within a post fractured bone. This device 100 had two sets of scissor grippers—one positioned proximally near the hub 110 (shown scissored-out in FIG. 1b and shown undeployed in FIG. 1a) and one near the tip 110'. On entry into a cavity, both grippers 110, 110' are flat and retracted (FIG. 1a). Upon deployment, both grippers 110, 110' scissor-out and grip the diaphyseal bone from the inside of the bone. Screws (not shown) placed through apertures through the hub 120 lock the device 100 to the metaphyseal bone. Hence, the metaphysis and the diaphysis are joined. A flexible-to-rigid body 130 is also provided positioned between the two grippers 110, 110'. The embodiment of the flexible-to-rigid body 130 is configured to form dual helical springs whose inner and outer tubular components coil in opposite directions. It is provided with spiral cuts 132 for that purpose.

Figure 4:
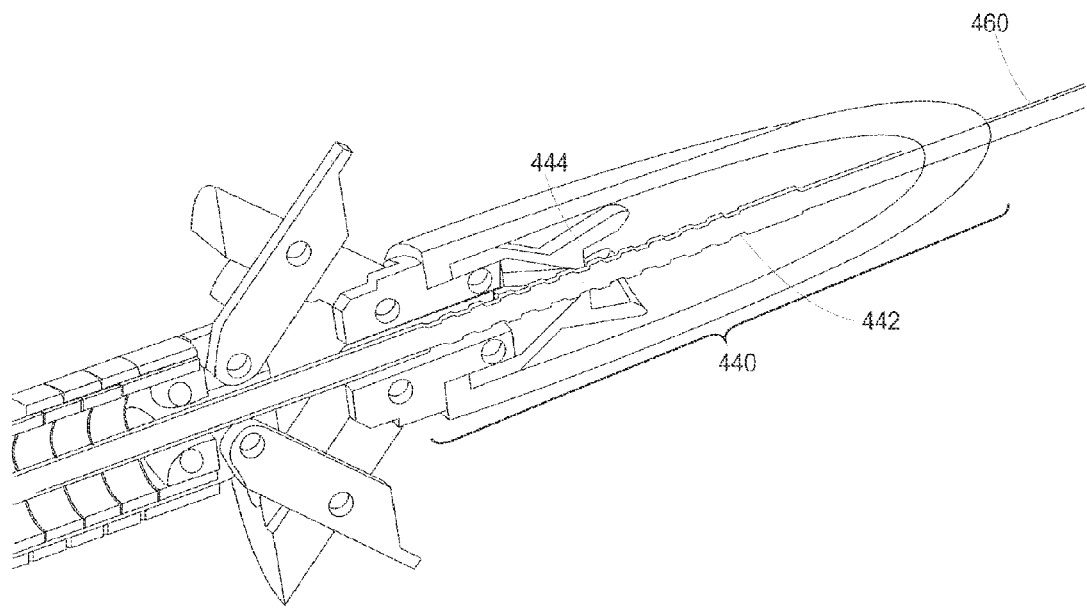
FIG. 4 is a cross-section of a ratchet, hub, gripper and flexible-to-rigid body components of the bone repair device of FIG. 1.

The bone fixation device 100 has an actuator 160 at a proximal end 10. The actuator 160 enables a user to control the movement, insertion, deployment, removal, and operation of the device. The actuator 160 has a ratchet feature 444 as shown in FIG. 4. The anchoring segments 110 have radially extending teeth or grippers that scissor out away from a central axis x of the device and that are deployed upon actuation of the device 100. The grippers interlock the device with the bone.

A bearing segment 150 suitable for use in an actuable bone fixation device is provided at the distal end of the device. The bearing segment can be adapted to act as blunt obsturator adapted to facilitate penetration of bone and to keep the tip of actuator 160 from digging into bone during insertion. The bearing segment, as depicted, has a substantially spherical dimension, with a lumen 152 positioned therethrough. The lumen depicted in this embodiment has a constant, or substantially constant, diameter along its length suitable for receiving the an actuator wire or guide wire 160 of a device 100. Actuator 160 is rigidly attached to bearing segment 150 and can be used separately from device 100 to serve as a guide wire for reaming before device 100 is inserted into the bone. During insertion, device 100 is inserted into the bone over the actuator 160 that also serves as a guide wire. Alternatively, Actuator 160 attached to bearing segment 150 can be assembled into device 100 and inserted as a unit into bone.

FIGS. 2a-d are views of flexible-to-rigid bodies 230, 230'. The flexible to rigid central body extends between the scissor grippers shown in FIG. 1. This feature is flexible upon entry into bone and rigid upon application of compressive axial force provided by tensioning actuator 160. Various embodiments exist only a few of which are depicted in FIG. 2. These include a dual helical spring 230 provided with spiral cuts 232 (FIG. 2a), a chain of ball bearings with flats or roughened surfaces, a chain of cylinders with flats, features, cones, spherical or pointed interdigitating surfaces, wavy-helical cut tubes (FIGS. 2c-d), two helical cut tubes in opposite directions (FIG. 2b), springs, linear wires with interdigitating coils, and bellows-like structures.

The design of the flexible-to-rigid tubular body 230 allows a single-piece design to maximize the transformation of the same body from a very flexible member that minimizes strength in bending to a rigid body that maximizes strength in bending and torque when compressive forces are applied in the axial direction at each end. The body 230 is made, for example, by a near-helical cut on a tubular member at an angle of incidence to the axis somewhere between 0+ and 180" from the longitudinal axis x of the tubular body 230. The near-helical cut or wavy-helical cut is formed by the superposition of a helical curve added to a cyclic curb that produces waves of frequencies equal or greater than zero per turn around the circumference and with cyclic amplitude greater than zero. The waves of on segment nest with those above and below it, thus increasing the torque and bending strength and stiffness of the tubular body when subjective to compressive forces. The tapered surfaces formed by the incident angle allow each turn to overlap with the segment above and below it, thus increasing the bending strength when the body is in compression. Additionally, the cuts can be altered in depth and distance between the cuts on the longitudinal x-axis along the length of the body 230 to variably alter the flexible-to-rigid characteristics of the tubular body along its length.

The cuts 232 in the body 230 allow an otherwise rigid member to increase its flexibility to a large degree during deployment. The Tubular member can have constant or varying internal and external diameters. This design reduces the number of parts of the flexible-rigid body of the device and allows insertion and extraction of the device through a curved entry port in the bone while maximizing its rigidity once inserted. Application and removal of compressive forces provided by a parallel member such as wire(s), tension ribbons or a sheath will transform the body from flexible to rigid and vice versa.

Figure 3A:
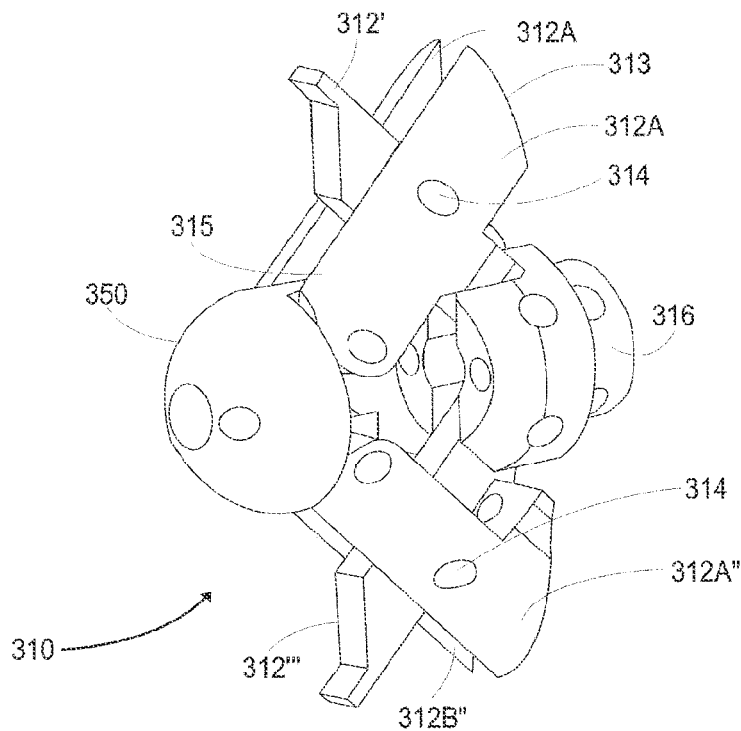
FIGS. 3A-C are views of a scissor gripper component of the bone repair device of FIG. 1.
Figure 3B:
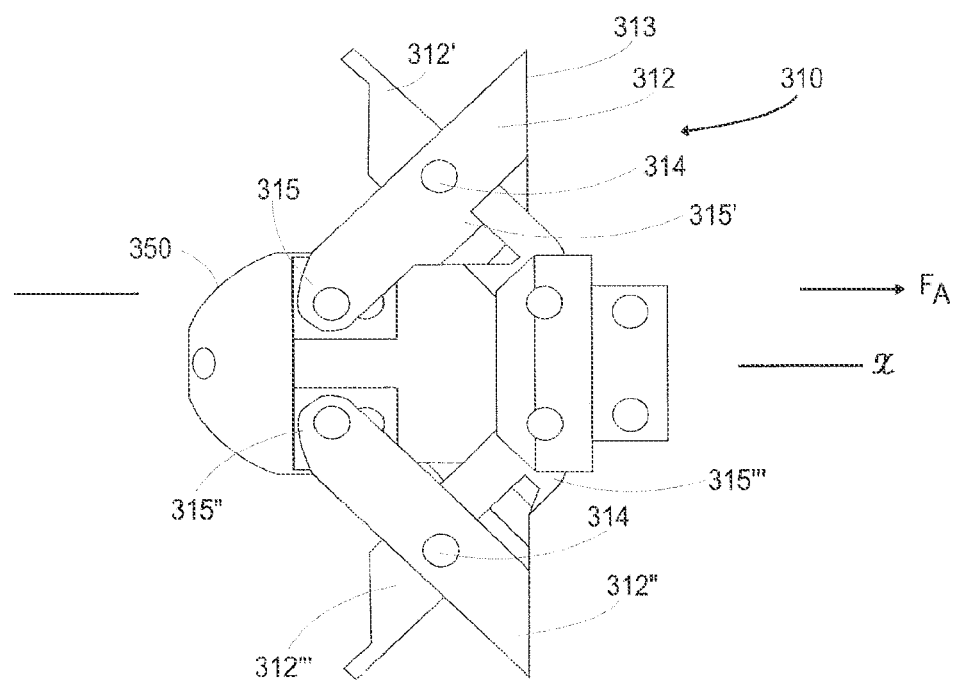
Figure 3C:
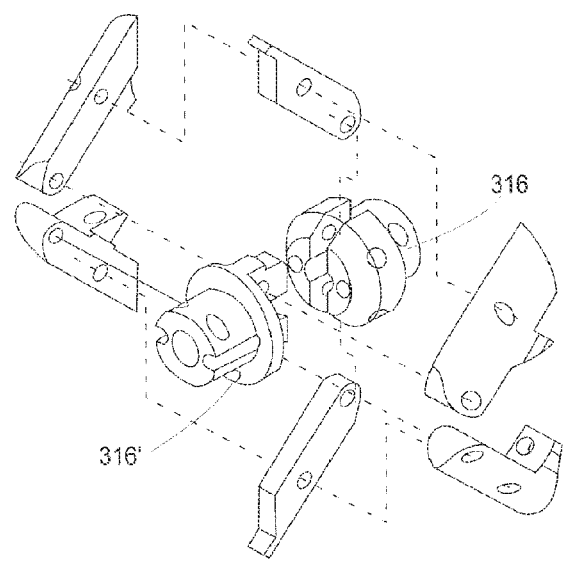

FIGS. 3a-c are views of the scissor gripper 310 component of the bone repair device 100 of FIG. 1. For purposes of illustration the distal gripper (110' from FIG. 1 is depicted) with the obsturator 350. The grippers or clamp 310 are comprised of a four bar linkage 312a, 312b, 312', 312a", 312b", 312''' analogous to an automotive scissor jack. In this embodiment the four bar linkage has free ends 313 beyond central pivots 314, 314' that translate radially, away from the longitudinal axis x. These free ends interdigitate into bone and grip in both directions of axial force, elbow to wrist and wrist to elbow. The tension force required by the grippers to attach to the bone decreases as they expand away from the central axis x. The axial force (elbow to wrist, wrist to elbow) to move the grippers increase as the grippers expand away from the central axis. Any number of scissor gripper assemblies can be part of the overall device. The space between the gripper assemblies is occupied by the flexible to rigid central body as shown above. The scissor grippers are actuated by applying an axial force $F_a$ opposite the direction of entry of the device into bone. For the embodiment depicted in FIG. 3, a distal set of interior pivoting ends 315, 315" are adapted to pivotally engage the obsturator 350 directly, or a connector 316' adapted to engage the obsturator which forms the distal end of the scissor gripper 310. A proximal set of interior pivoting ends 315', 315''' are adapted to engage a connector 316. The connector 316 can be adapted to engage, for example, a flexible-to-rigid body. For a gripper adapted to be positioned proximally, e.g., near the ratchet, the distal set of interior pivoting ends 315, 315" would be adapted to pivotally engage a connector 316 which is adapted to engage a flexible-to-rigid body. The proximal set of interior pivoting ends 315', 315''' would then be adapted to engage the ratchet. Other configurations of the scissor gripper can be employed and adapted according to the placement of the scissor gripper along the length of the device.

FIG. 4 is a cross-section of a ratchet component of the bone repair device of FIG. 1. A central ratcheting segment 440 of guide wire 460. This feature extends from the farthest surface of the device from the point of entry. It then extends back toward and completely through the resilient member 444 and metaphyseal hub 120. The central ratcheting guide wire has several functions. These include: guide wire for location within bone; guide wire for telescoping reaming of the intramedullary space; guide wire for location of the scissor concept implant; fixative datum for stopping intramedullary translation away from the point of entry into bone; rigid actuation surface to provide compressive force to collapse scissor grippers and make the flexible-to-rigid central body rigid; grooves 442, indentations, facets, changed surface features that interact with the resilient ratchet member 444 inside the metaphyseal hub. These features allow single directional translation of the central ratcheting guide wire opposite to the direction of entry into bone, but prevent translation of the central ratcheting guide wire back into the bone; collapses the scissor grippers thereby causing interdigitation into bone, this causes an expansion away from the central axis; allows the surgeon to cut off the central ratcheting guide wire so that it is below the outer surface of the metaphyseal hub and below the bone surface at the point of entry. For removal, once the resilient ratchet member is deflected away from the grooves, indentations, facets, changed surface features, the central ratcheting guide wire can be pushed away from the point of entry into bone, thereby collapsing the scissor grippers towards the central axis of the scissor concept implant; through out all of the functions of the central ratcheting guide wire, it is flexible and allows the scissor concept implant to bend around a radius of curvature less than 1.6 inches. The ratchet controls the locking and unlocking of the axial motion of the device.

Figure 5:
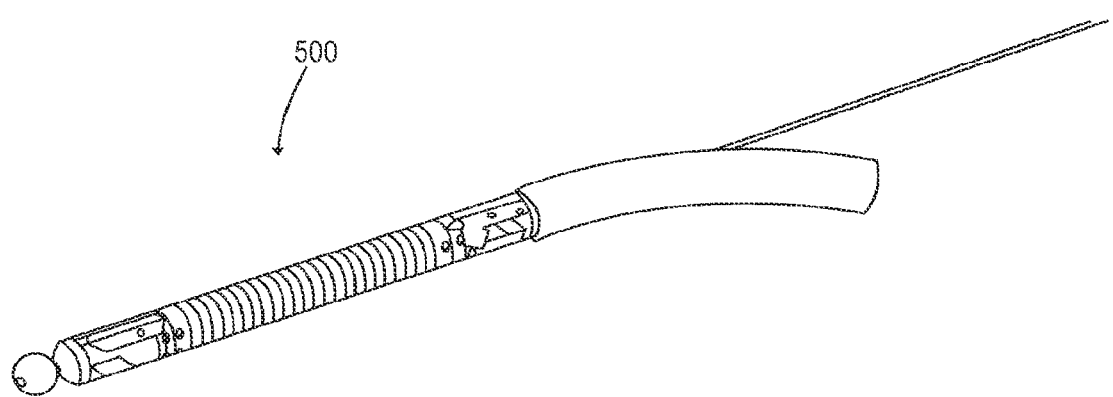
FIG. 5 is a retracted isometric view of the bone repair device of FIG. 1.

FIG. 5 is a refracted isometric view of the bone repair device 500 of FIG. 1.

FIGS. 6*a-g* are views of an alternative embodiment of a bone repair device according to the invention. Similar to the device depicted in FIG. 1, the device 600 can also be constructed from component parts. A feature of the device 600 is that its design it enables transmission of fixation forces to healthy unbroken bone. Another feature of the device 600 enables the device 600 to achieve asymmetric flexibility by using parts that increase a moment of inertia in a single axis. The moment of inertia of a point mass with respect to an axis is the product of the mass times the distance from the axis squared. The moment of inertia of any extended object, which applies in this instance, is a variant from that basic definition. The moment of inertia is important in an embodiment of a bone fixation, repair, or reinforcement device since flexibility in one plane and rigidity in a plane coincident and normal to said plane is required. This is achieved through the selective used of materials and specific geometric definition.

The design of the radius metaphyseal repair assembly device 600 depicted herein facilitates bone healing when placed in the intramedullary space within a post-fractured bone. This device 600 had two sets of diaphyseal-facing grippers 610 and two sets of metaphyseal-facing grippers 610'. All grippers 610, 610' are retracted during insertion. Upon deployment, all 4 prongs 612 on each of the 4 gripper sets push into the diaphyseal bone—preventing motion in either direction. Screws (not shown) can be placed through the hub 620 (on the right side) to lock the device position with respect to the metaphyseal bone. Hence, the metaphysis and the diaphysis are joined.

This device 600 had two sets of distal grippers—one positioned proximally near the distal tip 610 (shown scissored-out in FIGS. 6*a-b*); additionally a set of proximal grippers 611 can be provided. As depicted, the proximal grippers 611 deploy at a perpendicular angle to the deployment angle of the distal grippers. On entry into a cavity, the grippers 610 are flat and unfolded. Upon deployment, the grippers 610 extent away from the central axis X and grip the diaphyseal bone. Screws (now shown) placed through apertures (not shown) in the hub 620 lock the device 600 to the metaphyseal bone. Hence, the metaphysis and the diaphysis are joined. A central body 630 is also provided positioned between the grippers 610. The central body 630 as depicted is configured to surround at least a portion of the guide wire 660.

Figure 9:
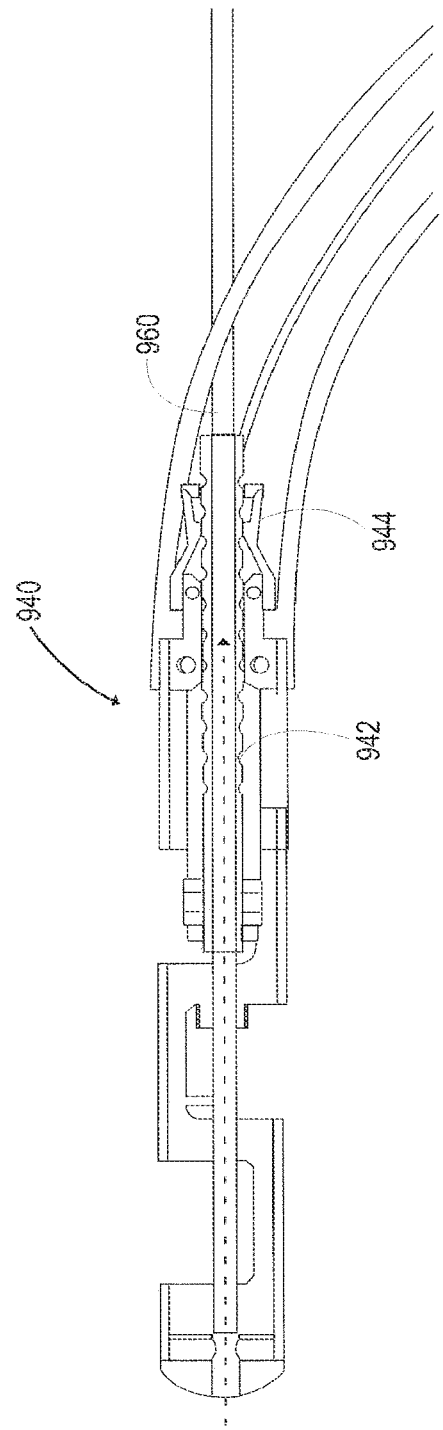
FIG. 9 is a view of a ratchet component of the bone repair device of FIG. 6.

The bone fixation device 600 has an actuator 660 at a proximal end 10. The actuator 660 enables a user to control the movement, insertion, deployment, removal, and operation of the device. The actuator 660 traverses ratchet feature 640 as shown in FIG. 9. The anchoring segments 610 have radially extending teeth or grippers that extend away from a central axis X of the device 600 and that are deployed upon actuation of the device 600. The grippers 610 interlock the device 600 with the bone. Ratchet feature 640 allows the actuator 660 to translate axially in the direction of deployment and keeps actuator 660 under tension.

A bearing segment 650 suitable for use in an actuable bone fixation device is provided at the distal end of the device. The bearing segment can be adapted to act as blunt obsturator adapted to facilitate penetration of bone. The bearing segment, as depicted, has a substantially spherical dimension, with a lumen 652 positioned therethrough. The lumen depicted in this embodiment has a constant, or substantially constant, diameter along its length suitable for receiving the drive shaft or guide wire 660 of a device 600. Guide wire 660 also serves as actuator 660.

Figure 6A:
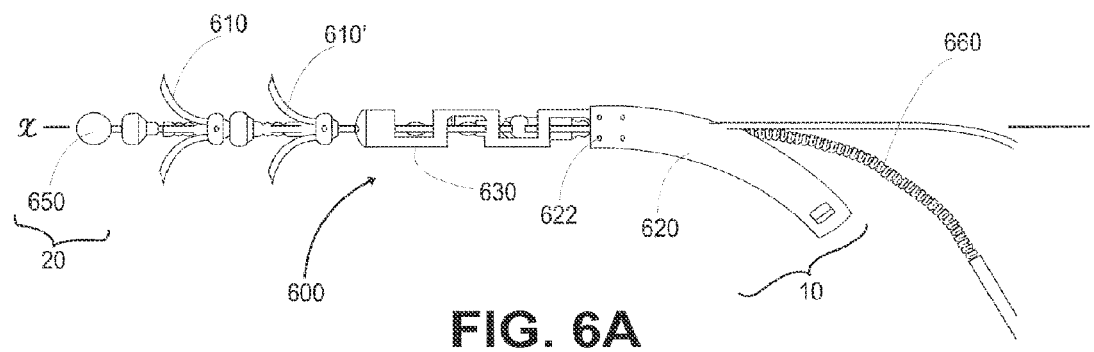
FIGS. 6A-G are views of an alternative embodiment of a bone repair device according to the invention.
Figure 6B:
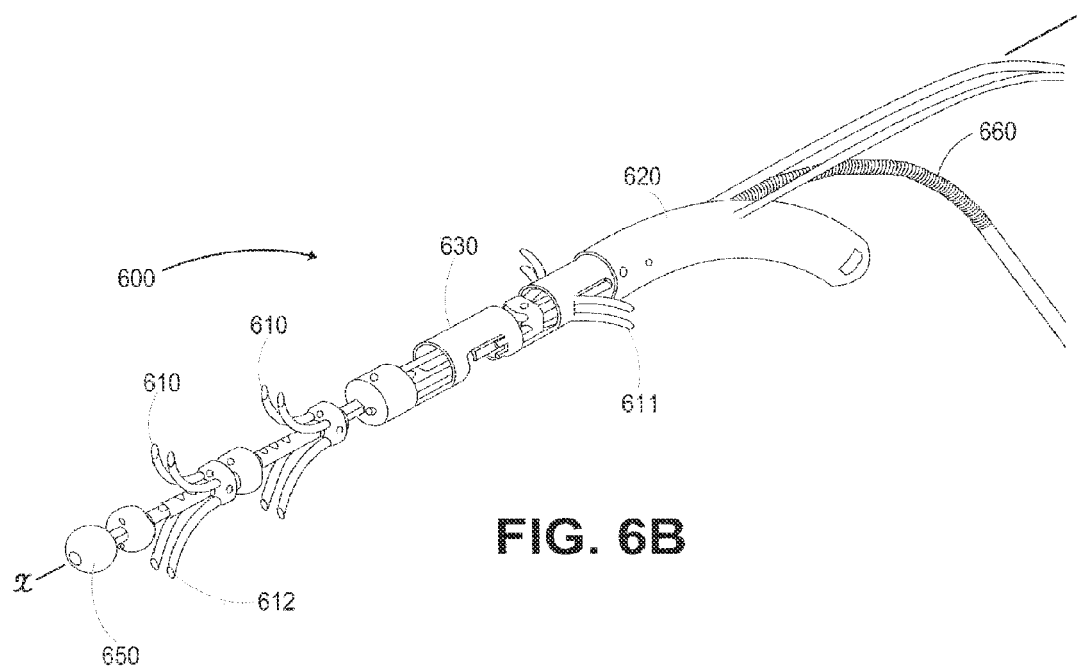
Figure 6C:
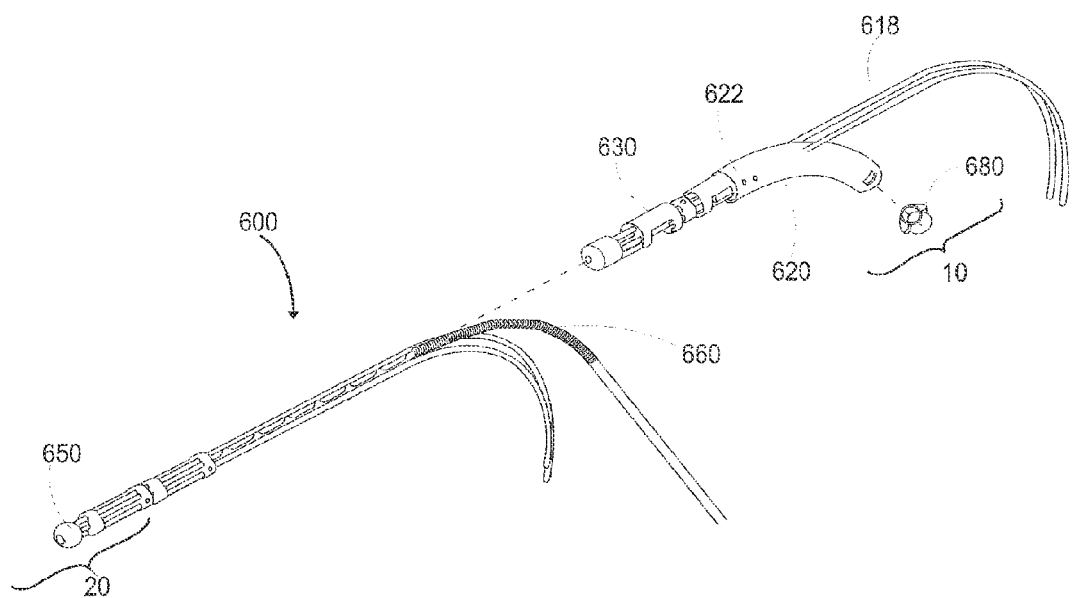
Figure 6D:
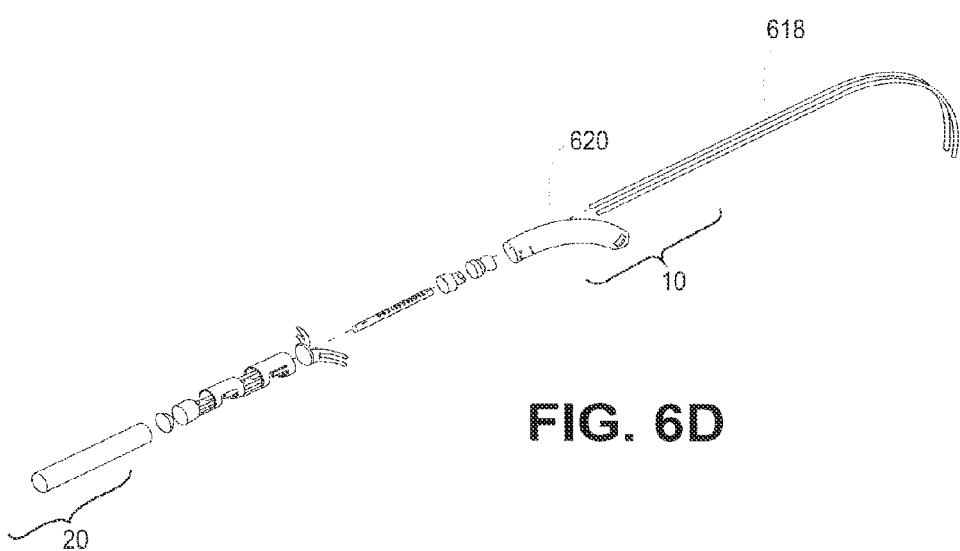
Figure 6E:
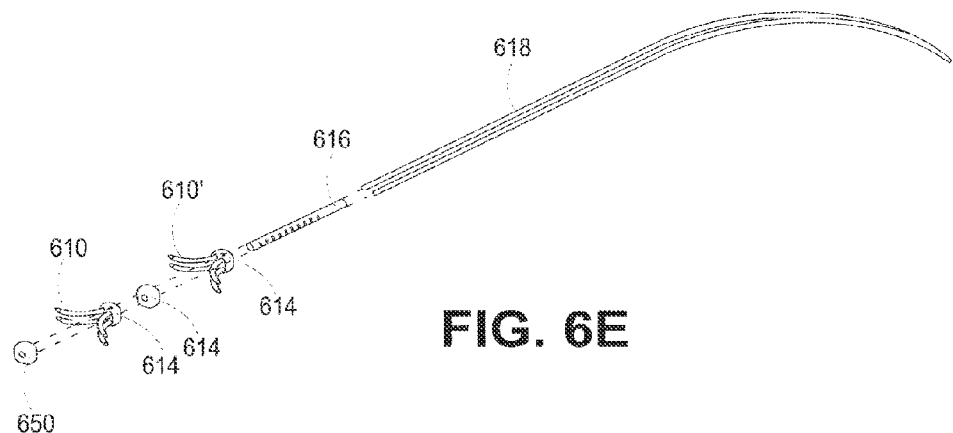
Figure 6F:
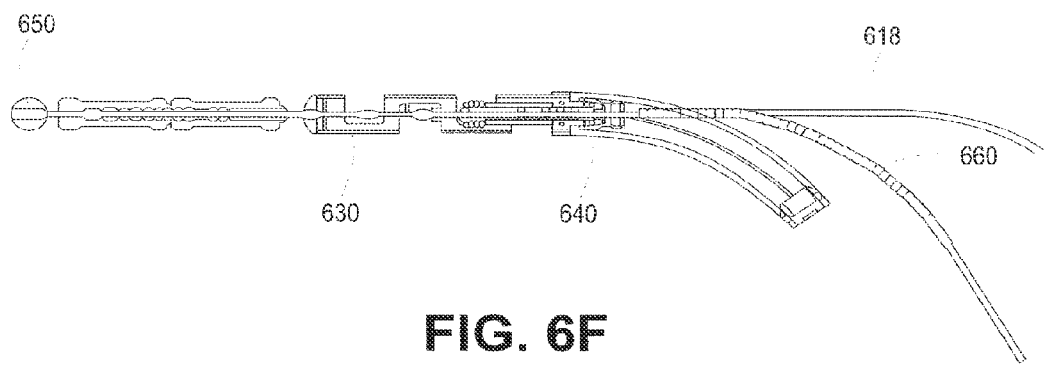
Figure 6G:
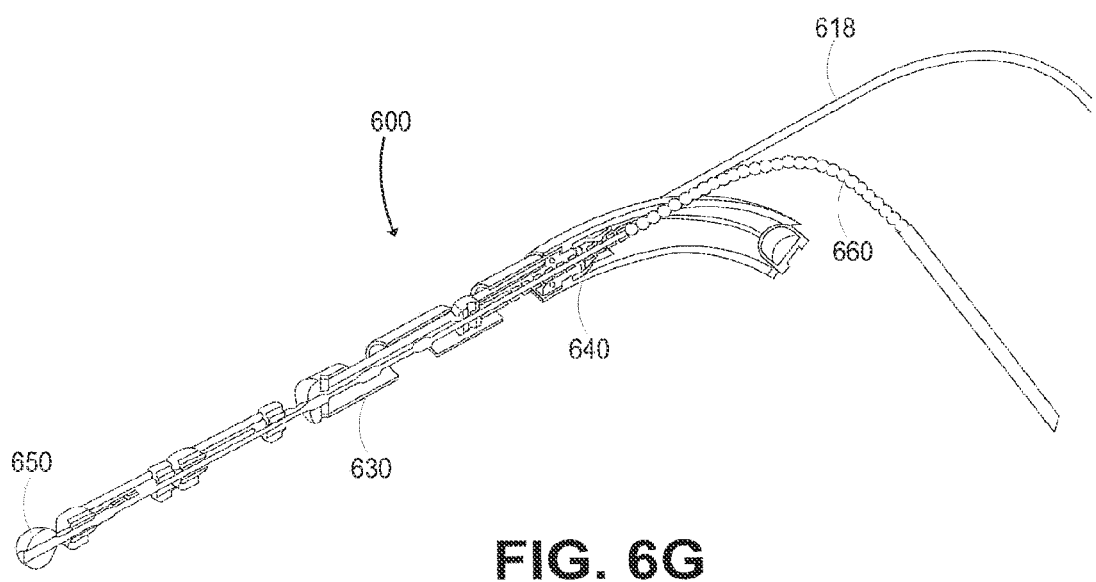

As shown in FIG. 6*e*, the grippers 610, 610' are configured to engage a bead 614 with apertures 615 through which the lateral lengths of the grippers fit. A low profile tube 616 is also provided which is adapted to fit within a central aperture of the beads 614. Tendons 618 are also provided. The tendons serve a variety of functions as would be appreciated by those skilled in the art. In one instance, the tendons provide for greater effective moment of inertia in the Z-direction, which is the plane normal to the dorsal plane or the volar surfaces of the wrist. The tendons 618 also actuate the grippers in and out of the sheath. Pulling the tendons 618 makes the grippers of the device extend out of the device sleeve, thus penetrating bone. Once the grippers penetrate bone, the device is anchored.

Figure 7A:
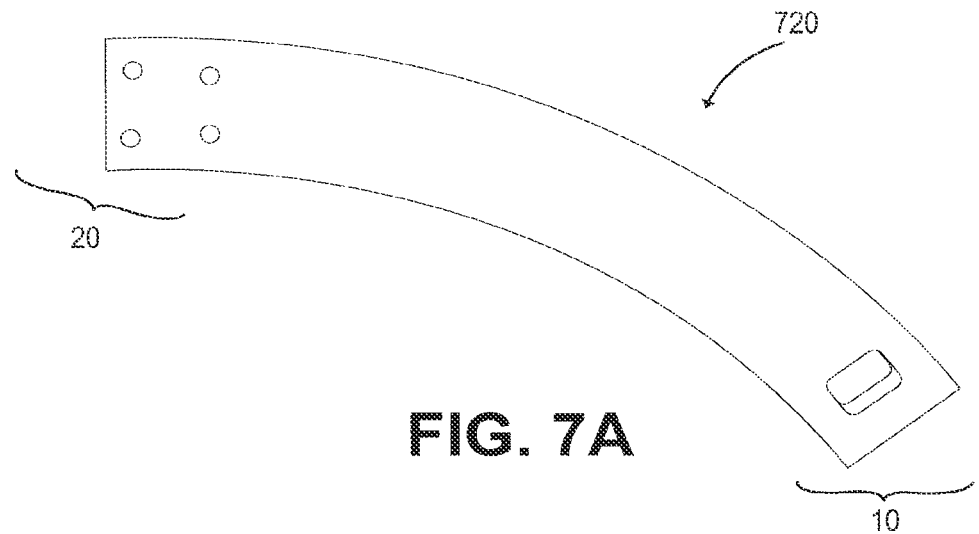
FIGS. 7A-B are views of a hub component of the bone repair device of FIG. 6.
Figure 7B:
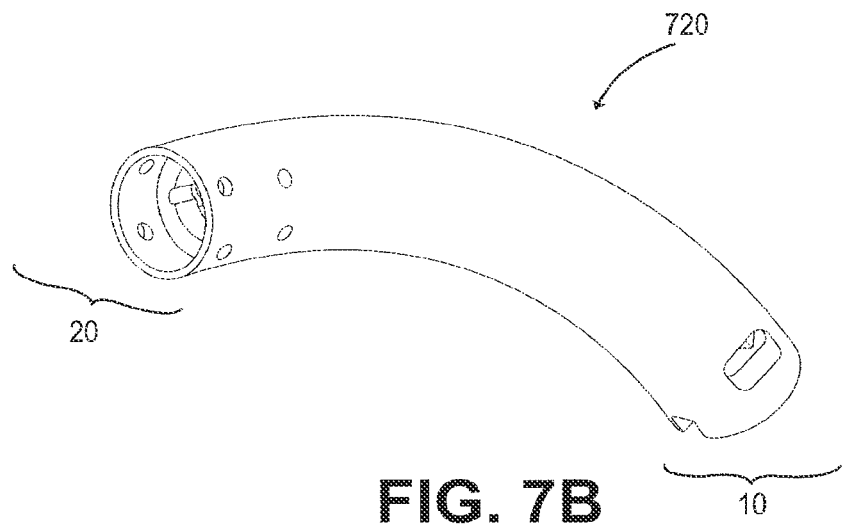

FIGS. 7*a-b* are views of a hub 720 component of the bone repair device of FIG. 6. The metaphysial hub is adapted to engage the repair device 600 at its distal end 20 and is adapted to engage a lock 680 at is proximal end 10. The metaphyseal hub is a component of the device that performs several functions:

Structural Linkage Between Different Compositions of Bone

First, the metaphyseal hub 720 creates the structural linkage between the transitional sections of bone. These are the exterior cortex of bone, the metaphysis, and the diaphysis. The hub can be rigid or flexible. In these embodiments the metaphyseal hub is made of a rigid thermoplastic polymer. Examples of these materials include polyetheretherketone, polyaramids, such as nylon, and ultra high molecular weight polyethylene. The primary advantages of these engineering thermoplastic polymers include geometric conformity to the transition of bone, geometric conformity to the transitional geometry of the device from the exterior cortex through the metaphysis and the diaphysis. In these embodiments the shape of the metaphyseal hub had a circular, tubular shape, curved at a constant radius.

Curved to Allow Minimally Invasive Access to the Intramedullary Space

In some embodiments of the invention, the radius of curvature for the hub 720 is between 2.0 inches to 0.5 inches. The radius of curvature allowed for the angle of penetration through the exterior cortex of the bone to be between 80 degrees from perpendicular to perpendicular to the bone. In the case of the radius the "bone" as described, would be the radial styloid. The circular cross section is designed to match access hole.

The diameter of the cross sectional circular area of the tubular metaphyseal hub 720 is between 0.020 inches to 2 inches as determined by the size of the intramedullary space of the bone that is under repair. The circular cross-section helps to minimize trauma.

Interface to Metaphyseal Bone Attachment Devices (Screws)

The metaphyseal hub 720 allows the placement of bone screws (not shown) or other devices that secure the metaphyseal bone to the metaphyseal hub. In the case of screws, a thermoplastic metaphyseal hub allows the surgeon to drill pilot holes from bone, through the metaphyseal hub, and into bone. A screw that is larger in diameter than the pilot hole would be inserted with a twisting motion and interfere with bone, the metaphyseal hub, and bone. This construction allow secure fixation of the distal fragments (proximal to the surgeon) of the fractured bone to device 600 which in turn is secured to the proximal side of the fractured bone. (distal to the surgeon)

Interface to the Drilling and Screw Placement Outrigger

The metaphyseal hub 720 can also be adapted to interface with an outrigger (See, co-pending application Ser. No. 60/866,976 filed Nov. 22, 2006 to Phillip Jobson for SURGICAL TOOLS FOR USE IN DEPLOYING BONE REPAIR DEVICES which describes an outrigger tool). The outrigger allows exact placement of bone screws so that the screws penetrate bone, then the metaphyseal hub, then the bone on the opposite side of the metaphyseal hub. This hub interface can be a thread, bayonet style spring loaded contact, snap fit, interference fit, or other alternately fixative and stable attachment with removability Interface to the Diaphyseal Fixation Section The metaphyseal hub 720 has an interface to the diaphyseal fixation section of the device 600. This interface attaches the diaphyseal fixation section to the metaphyseal section provides an alternately, reversible, actuator or ratchet 640. This actuator 640 allows single direction translation of the actuator rod 660 or ratcheting guide wire that deploys the diaphyseal cortical interfacial attachment moieties.

Figure 8A:
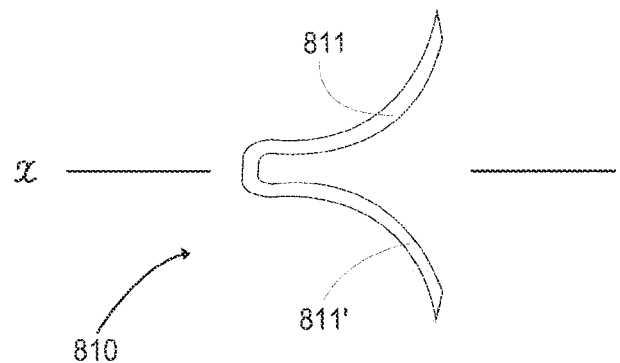
FIGS. 8A-B are views of a gripper component of the bone repair device of FIG. 6.
Figure 8B:
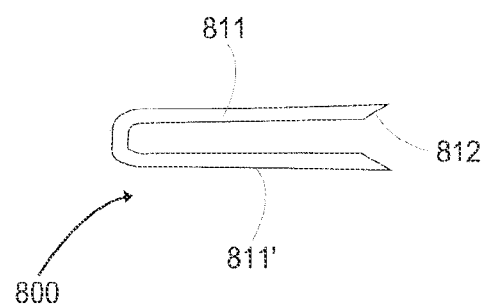

FIGS. 8*a-b* are views of a gripper 810 component of the bone repair device of FIG. 6. The gripper 810 is configured to form a flat bottomed u-shape (similar to a staple). The two sides 811, 811' are configured to flare away from a central axis x of the gripper during deployment. The ends of the grippers can be shaped such that they are sharply pointed 812.

FIG. 9 is a view of a ratchet component of the bone repair device of FIG. 6. A central ratcheting element 944 is traversed by guide wire 960 with grooves 942. This feature extends from the farthest surface of the device from the point of entry. It then extends back toward and completely through the resilient member and metaphyseal hub. The central ratcheting guide wire has several functions. These include: guide wire for location within bone; guide wire for telescoping reaming of the intramedullary space; guide wire for location of the scissor concept implant; fixative datum for stopping intramedullary translation away from the point of entry into bone; rigid actuation surface to collapse scissor grippers and make the flexible to rigid central body rigid; grooves 942, indentations, facets, changed surface features that interact with the resilient ratchet member 944 inside the metaphyseal hub. These feature allow single directional translation of the central ratcheting guide wire 960 towards the point of entry into bone, but prevent translation of the central ratcheting guide wire away point of entry into bone; collapses the scissor grippers thereby causing interdigitation into bone, this causes an expansion of the grippers away from the central axis; allows the surgeon to cut off the central ratcheting guide wire so that it is below the outer surface of the metaphyseal hub; once the resilient ratchet member is deflected away from the grooves, indentations, facets, changed surface features, the central ratcheting guide wire can be pushed away from the point of entry into bone, thereby collapsing the scissor grippers towards the central axis; through out all of the functions of the central ratcheting guide wire, it is flexible and allows the bone fixation devices such as device 600 to bend around a radius of curvature less than 1.6 inches. The ratchet locks and releases the axial and angular position of the device.

A corollary embodiment of the previously described art include axial translation from distal to proximal ends of the device thereby drawing bone and tissue together through shortening the axial distance distal to proximal between the two sides of the fracture(s). These embodiments have specific applications in fracture non-unions, joint fusions and certain fractures that require the compression of the fracture surfaces.

Additional embodiments, methods, and uses are envisioned in accordance with the inventive attributes. One embodiment of the present invention provides a low weight to volume mechanical support for fixation, reinforcement and reconstruction of bone or other regions of the musculo-skeletal system. The method of delivery of the device is another aspect of the invention. The method of delivery of the device in accordance with the various embodiments of the invention reduces the trauma created during surgery, decreasing the risks associated with infection and thereby decreasing the recuperation time of the patient. The framework may in one embodiment include an expandable and contractible structure to permit re-placement and removal of the reinforcement structure or framework.

In accordance with the various embodiments of the present invention, the mechanical supporting framework or device may be made from a variety of materials such as metal, composite, plastic or amorphous materials, which include, but are not limited to, steel, stainless steel, cobalt chromium plated steel, titanium, nickel titanium alloy (nitinol), superelastic alloy, and polymethylmethacrylate (PMMA). The supporting framework or device may also include other polymeric materials that are biocompatible and provide mechanical strength, that include polymeric material with ability to carry and delivery therapeutic agents, that include bioabsorbable properties, as well as composite materials and composite materials of titanium and polyetheretherketone (PEEK™), composite materials of polymers and minerals, composite materials of polymers and glass fibers, composite materials of metal, polymer, and minerals.

Within the scope of the present invention, each of the aforementioned types of device may further be coated with proteins from synthetic or animal source, or include collagen coated structures, and radioactive or brachytherapy materials. Furthermore, the construction of the supporting framework or device may include radio-opaque markers or components that assist in their location during and after placement in the bone or other region of the musculo-skeletal systems.

Further, the reinforcement device may, in one embodiment, be osteo incorporating, such that the reinforcement device may be integrated into the bone.

In a further embodiment, there is provided a low weight to volume mechanical supporting framework or device deployed in conjunction with other suitable materials to form a composite structure in-situ. Examples of such suitable materials may include, but are not limited to, bone cement, high density polyethylene, Kapton®, polyetheretherketone (PEEK™), and other engineering polymers.

Once deployed, the supporting framework or device may be electrically, thermally, or mechanically passive oractive at the deployed site within the body. Thus, for example, where the supporting framework or device includes nitinol, the shape of the device may be dynamically modified using thermal, electrical or mechanical manipulation. For example, the nitinol device or supporting framework may be expanded or contracted once deployed, to move the bone or other region of the musculo-skeletal system or area of the anatomy by using one or more of thermal, electrical or mechanical approaches.

The invention also includes a method for repairing a bone fracture comprising: accessing a fracture along a length of bone through a bony protuberance at an entry portal; introducing the bone fixation device into the medullary canal through the entry portal; bending the bone fixation device along its length to advance into the medullary space in the bone; bending the bone fixation device along its length to traverse the fracture site; placing a flexible elbow in the medullary canal at the fracture site; stiffening the bone fixation device; locking the bone fixation device to the bone; reducing the fracture with the bone fixation device in place in the medullary canal; locking the flexible elbow to achieve intramedullary reduction of the fracture. The method can further include the step of introducing a guide wire into the medullary space through a bony protuberance at an entry portal. Additionally, the guide wire can be reamed through the bony protuberance at an entry portal. The location of the reamed boney canal can be determined by the fracture geometry and bone anatomy. In some embodiments of the method, a sleeve can be advanced along the bone fixation device. In such embodiments, the sleeve can function to unlock the spikes from the fixation device. Once the spikes are unlocked from the fixation device, the spikes then fix the device to the bone. Locking butterfly rings can also be employed to lock the device to the bone. The butterfly rings can be locked to the fixation device in some embodiments. Additionally, the rings can be threaded over the device. In other embodiments, a guide jig guides screws through the butterfly rings. Further self tapping screws lock the butterfly rings to the bone and bone fixation device. A set screw can also be used to lock the device at the fracture site. The device can also be stiffened. In performing the method of the invention, fracture fragments can be reduced.

Yet another aspect of the invention includes a barb-screw comprising a sleeve, one or more teeth deployable at a distal end of the sleeve, and an actuable lock adapted to secure the sleeve within the space of the bone from an end of the device.

Where the proximal end of a device in the anatomical context is the end closest to the body midline and the distal end in the anatomical context is the end further from the body midline, for example, on the humerus, at the head of the humerus (located proximal, or nearest the midline of the body) or at the lateral or medial epicondyle (located distal, or furthest away from the midline); on the radius, at the head of the radius (proximal) or the radial styloid process (distal); on the ulna, at the head of the ulna (proximal) or the ulnar styloid process (distal); for the femur, at the greater trochanter (proximal) or the lateral epicondyle or medial epicondyle (distal); for the tibia, at the medial condyle (proximal) or the medial malleolus (distal); for the fibula, at the neck of the fibula (proximal) or the lateral malleoulus (distal); the ribs; the clavicle; the phalanges; the bones of the metacarpus; the bones of the carpus; the bones of the metatarsus; the bones of the tarsus; the sternum and other bones, the device will be adapted and configured with adequate internal dimension to accommodate mechanical fixation of the target bone and to fit within the anatomical constraints. As will be appreciated by those skilled in the art, access locations other than the ones described herein may also be suitable depending upon the location and nature of the fracture and the repair to be achieved. Additionally, the devices taught herein are not limited to use on the long bones listed above, but can also be used in other areas of the body as well, without departing from the scope of the invention. It is within the scope of the invention to adapt the device for use in flat bones as well as long bones.

The devices disclosed herein can be deployed in a variety of suitable ways, as would be appreciated by those skilled in the art. For example, a provisional closed reduction of the fracture can be performed wherein a 1.5 to 2 inch incision is made overlying the metaphyseal prominence of the bone. Blunt dissection is then carried to the fascia whereupon the fascia is incised. The surgical approach to the central aspect (anterior-posterior) proceeds by either splitting the tendon or ligament or muscle longitudinally or by elevating structures of the bone in a subperiosteal fashion. The choice of the particular approach varies with respect to the fractured bone that is being treated. A specialized soft tissue retractor is placed onto the bone retracting the soft tissues away from the entry point of the bone.

A guide wire can then be drilled at an angle into the insertion point along the metaphyseal prominence. The angle of placement of the guide wire along the longitudinal axis of the bone depends on the fracture anatomy and particular bone being treated. The guide wire can then be placed under fluoroscopic guidance. An optimally chosen reamer is introduced over the guide wire opening the metaphyseal entry point. Both devices are then removed.

A curved guide wire is introduced across the open channel of the metaphysis and is advanced across the fracture site into the diaphysis of the bone. Sequential reaming appropriate for the particular device is performed to prepare the diaphysis. The distance from the fracture site to the entry point is estimated under fluoroscopy and the appropriate device is selected. The reamer is withdrawn and the device is introduced over the guide wire into the metaphysis and across the fracture into the diaphysis. Fluoroscopy confirms the location of the universal joint at the metaphyseal/diaphyseal fracture site. Alternatively, the device is introduced into the metaphysic after the removal of the guide wire.

The diaphyseal teeth of the device are deployed and the device is rigidly fixed to the diaphysis of the fractured bone distal to the fracture site. Any extension of the fracture into the joint can now be reduced in a closed fashion and held with K wires or in an open fashion via a dorsal approach to the intra-articular portion of the fracture. Metaphyseal locking flanges with targeting outriggers attached are now advanced (in to the metaphyseal bone) across the metaphysis. Using the attached targeting outrigger, guide wires are now placed through the metaphyseal locking flanges. The guide wires are directed fluoroscopically to stabilize the intra-articular portion of the fracture and/or to stabilize the metaphyseal fracture securely. Holes are drilled over the guide wires with a cannulated drill bit, or alternatively, holes are drilled guided by the outrigger without the use of guidewires and with a non-canulated drill bit. Then, self tapping screws are advanced over the guide wires to lock the bone to the shaft and metaphyseal locking flange or alternatively, self tapping screws are advanced guided by the outrigger without the use of a guide wire to lock the bone to the shaft and metaphyseal locking flange. The device is now locked within the proximal and distal bone fragments (metaphyseal or diaphyseal) and distal (diaphyseal) bone. This provides for rigid fixation of the comminuted intra-articular fragments to each other, and the fixation between these screws interlocking in to the metaphyseal flange component provides rigid fixation of these intra-articular fragments in the metaphyseal region to the diaphyseal shaft as well. The extremity and fracture is now manipulated until a satisfactory reduction is achieved as visualized under fluoroscopy. Thereafter, the fracture is manipulated under fluoroscopic guidance in order to achieve anatomic alignment of the bone fragments. Once optimal intramedullary reduction is achieved, the universal joint is locked. The fracture is now fixed securely. The guide wire is removed and the wound is closed repairing the periosteum over the metaphyseal entry point and repairing the fascia and closing the skin. A splint may be applied.

The embodiments shown in FIGS. 10*a-b*, 11*a-b* and 12 are described below, after the discussion of FIGS. 13-59.

Figure 13:
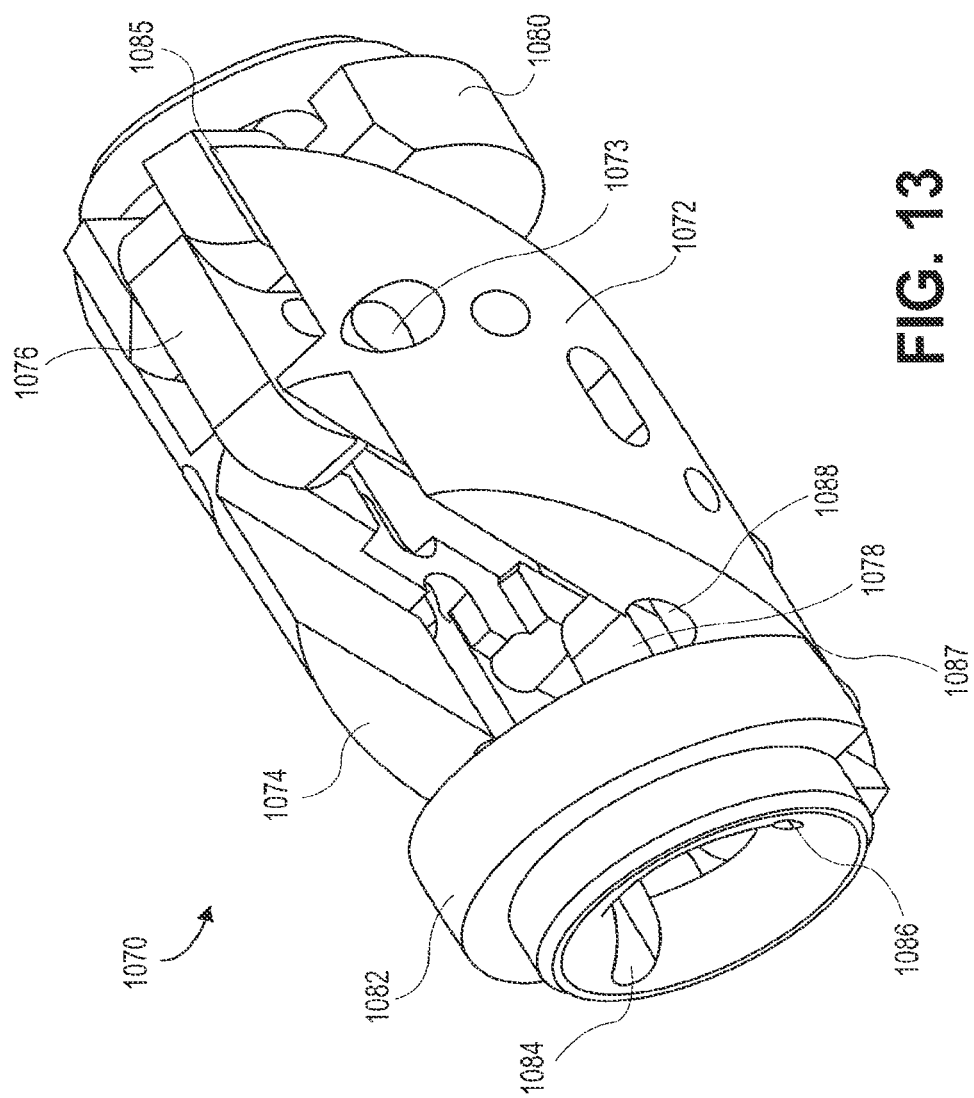
FIGS. 13-18 show details of one embodiment of an actuatable gripper for use with a fracture fixation device.
Figure 14:
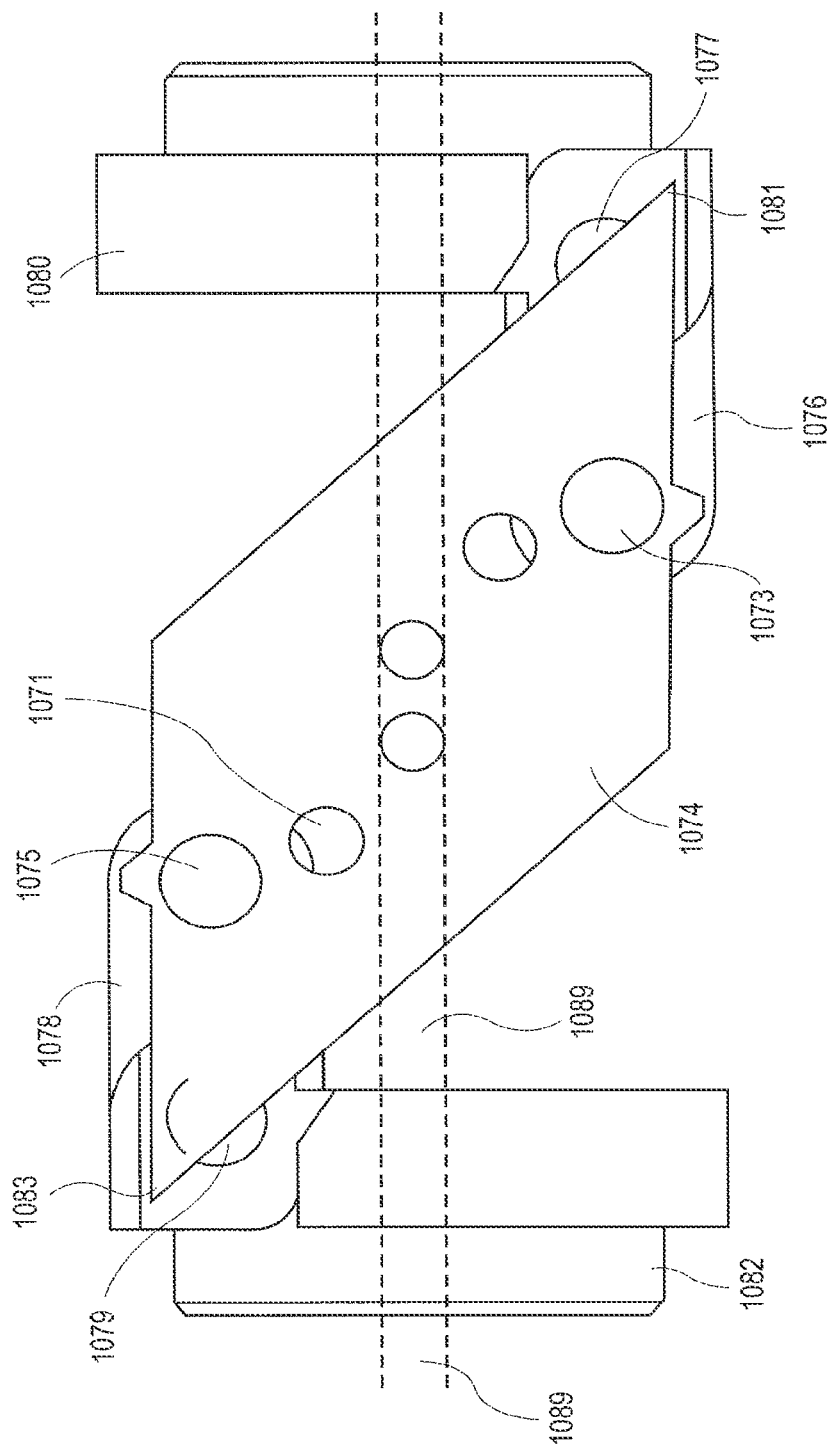
Figure 15:
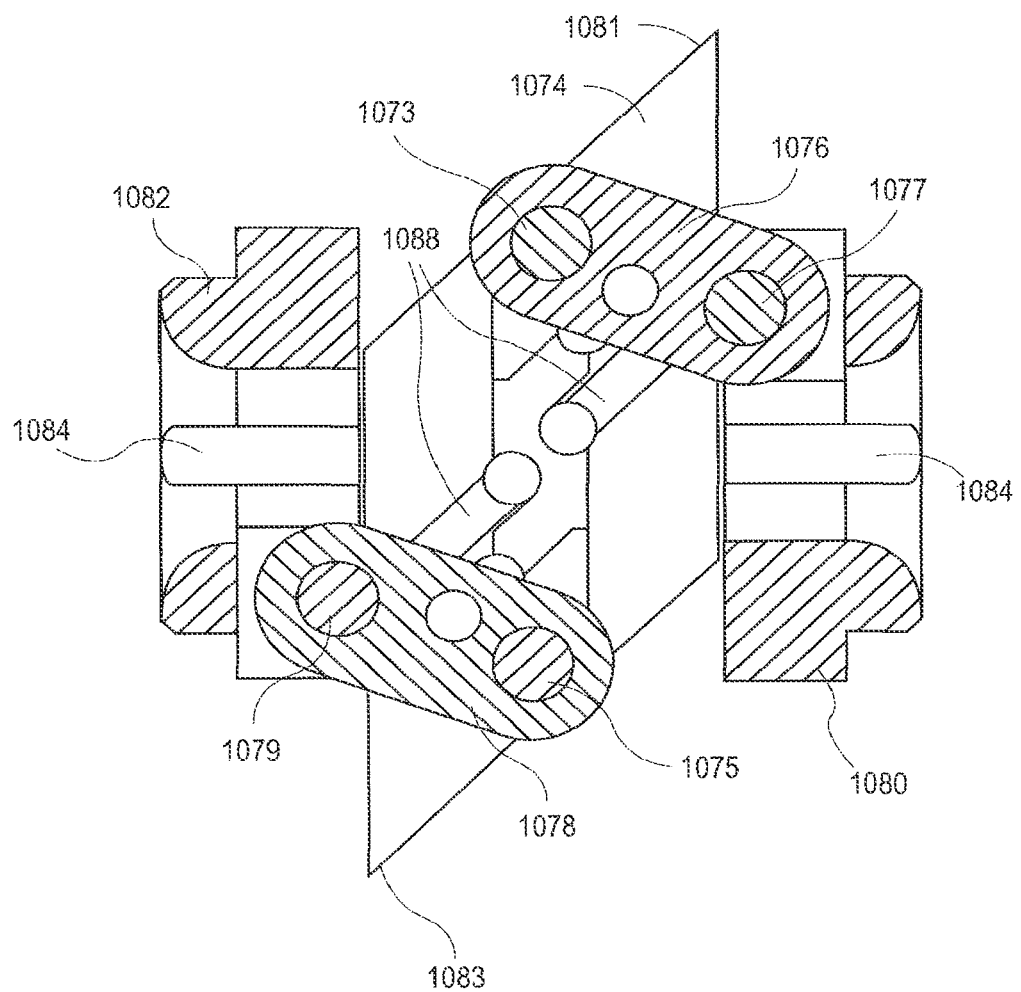

FIGS. 13-15 show details of an actuatable gripper 1070 for use with, e.g., the fracture fixation device embodiments described above. In this embodiment, gripper 1070 has two rotatable cams 1072 and 1074. Cams 1072 and 1074 are attached by pins 1073 and 1075 to cam arms 1076 and 1078, respectively. Pins 1073 and 1075 are rotationally and axially fixed to cams 1072 and 1074. Pins 1073 and 1075 are axially fixed to arms 1076 and 1078 but free to move rotationally. Arms 1076 and 1078 are attached by pins 1077 and 1079 to flanges 1080 and 1082, respectively. Pins 1077 and 1079 are axially and rotationally fixed to flanges 1080 and 1082, but arms 1076 and 1078 are only constrained axially and free to move rotationally. Flanges 1080 and 1082 connect with the components on either end of the device. In the undeployed configuration shown in FIGS. 13 and 14, cams 1072 and 1074 are oriented such that the sharp tips 1085 and 1087 of cam 1072 and the sharp tips 1081 and 1083 of cam 1074 do not extend from the cylinder of the gripper. When foreshortened during deployment, however, movement of flanges 1080 and 1082 toward each other causes cam arms 1076 and 1078 to rotate about pins 1077 and 1079 with respect to flanges 1080 and 1082 and causes cams 1072 and 1074 to rotate about pins 1073 and 1075 with respect to cam arms 1076 and 1078 so that the sharp tips swing out from the cylinder of the gripper, as shown in FIG. 15. Thus, when part of a fracture fixation device that has been inserted into a bone, deployment of the gripper 1070 causes the sharp tips of the cams to dig into the bone to anchor the device. An alternative design combines cams 1072 and 1074 into one integral component.

In order to prevent inadvertent deployment of the gripper, one or more optional lock wires may be inserted into the gripper. As shown in FIG. 13, lock wire channels 1084 and 1086 may be formed in flanges 1080 and 1082, and corresponding channels may be formed in flange 1080. Likewise, lock wire channels may be formed in the cams, such as channel 1088 formed in cam 1074, to line up with the lock wire channels formed in the flanges when the gripper is in its undeployed configuration, thereby permitting a lock wire 1089 to be inserted through the gripper, as shown in FIG. 14. Lock wire 1089 must be removed before the gripper can be rotated to its foreshortened deployed configuration, as shown in FIG. 15. A lock wire may also be inserted across the gripper through holes 1071.

Figure 16:
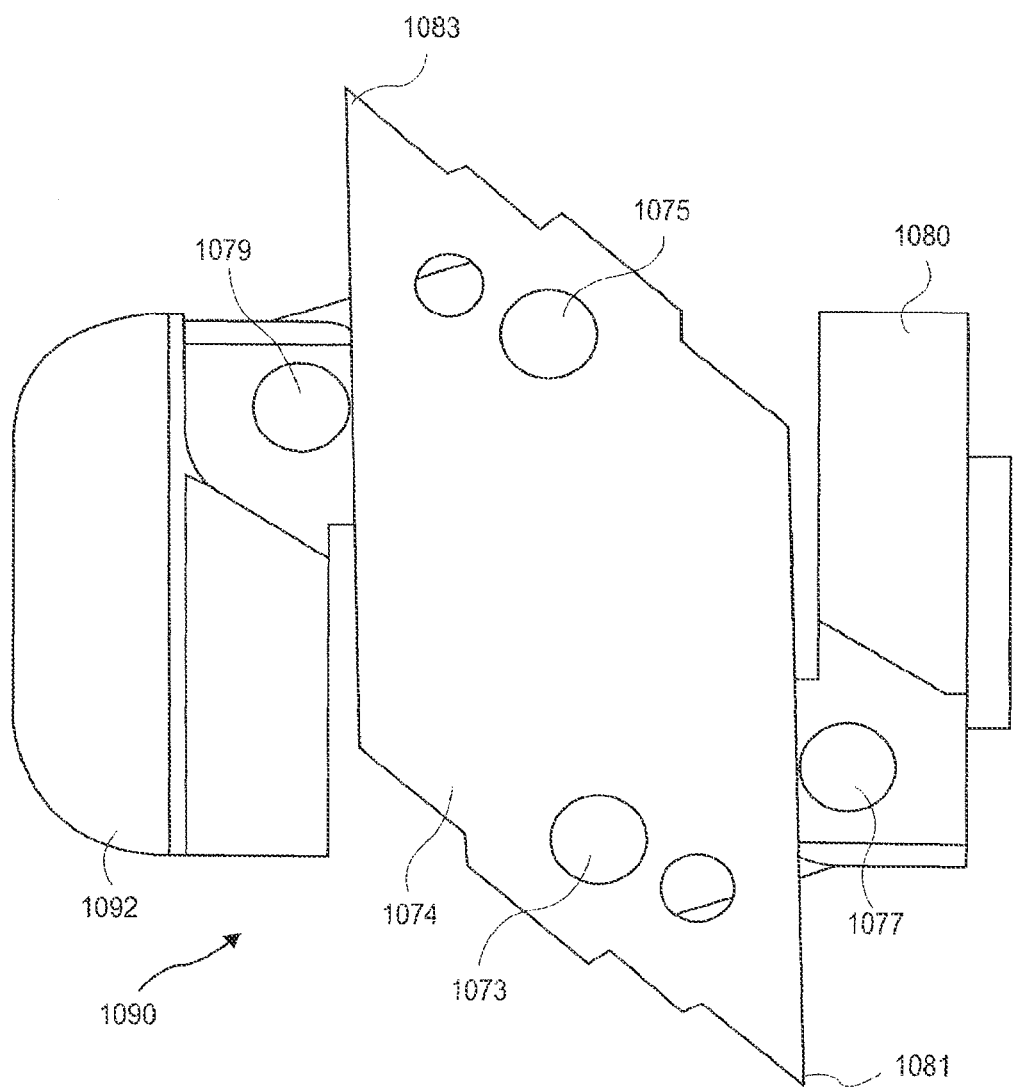
Figure 17:
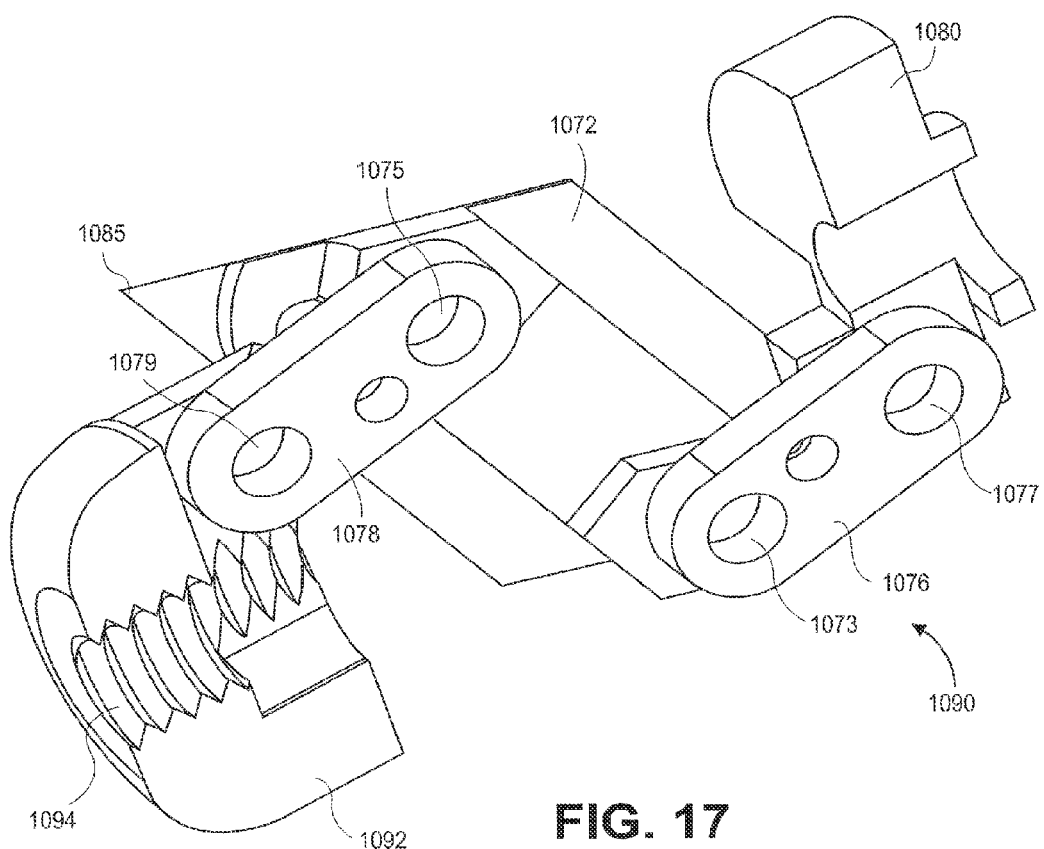
Figure 18:
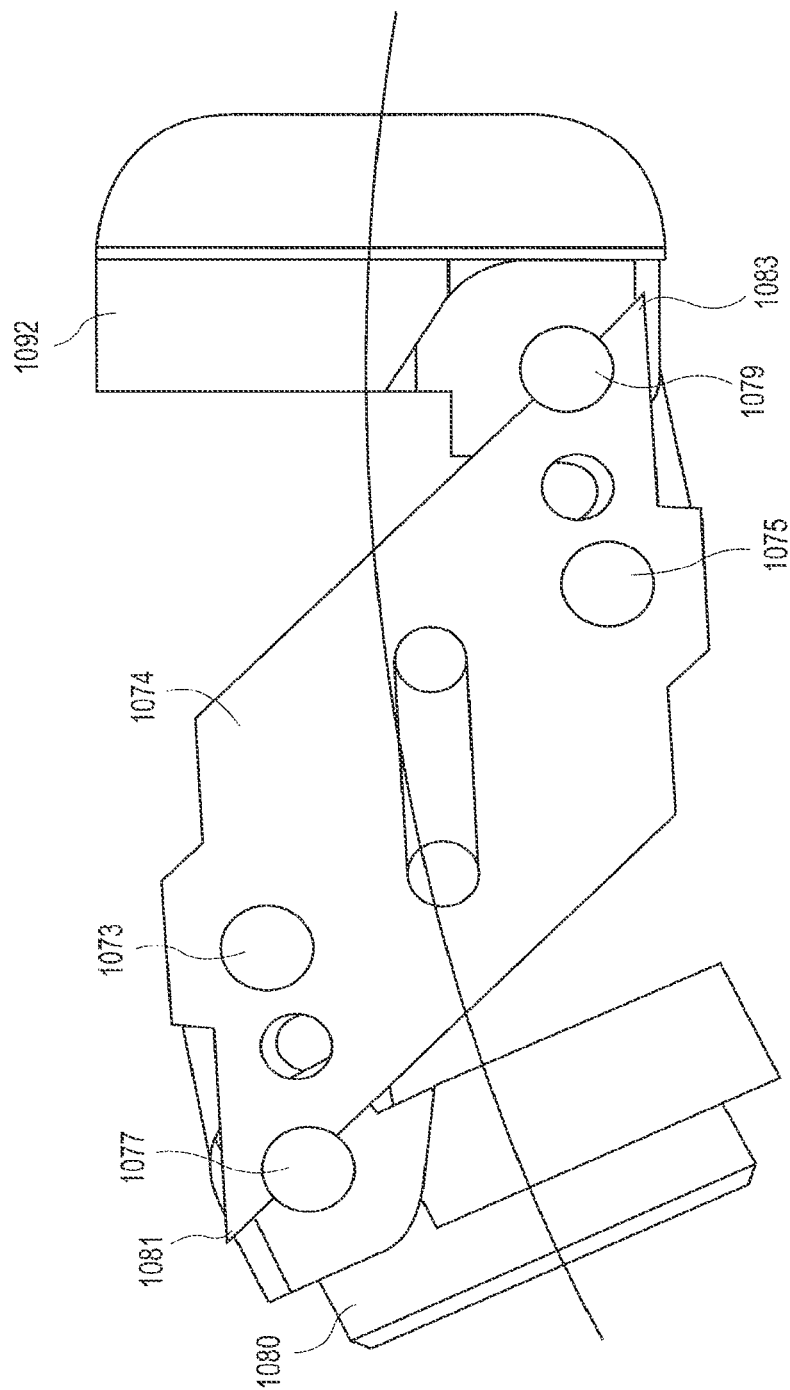

FIGS. 16-18 show a gripper 1090 for use on one end of an actuatable fracture fixation device according to one embodiment of the invention. In this embodiment, a threaded flange 1092 replaces flange 1082 of the earlier gripper embodiment. Internal threads 1094 in flange 1092 interact with a threaded actuator, such as actuator 1614 shown in FIGS. 10 and 11, for use in foreshortening during deployment.

FIG. 18 also demonstrates an advantage of the grippers 1070 and 1090 shown in FIGS. 13-18. During insertion into the interior of a bone along a curved insertion path, grippers 1070 and 1090 can adapt to the curve of the insertion path, as shown by the curved line in FIG. 18.

Figure 19:
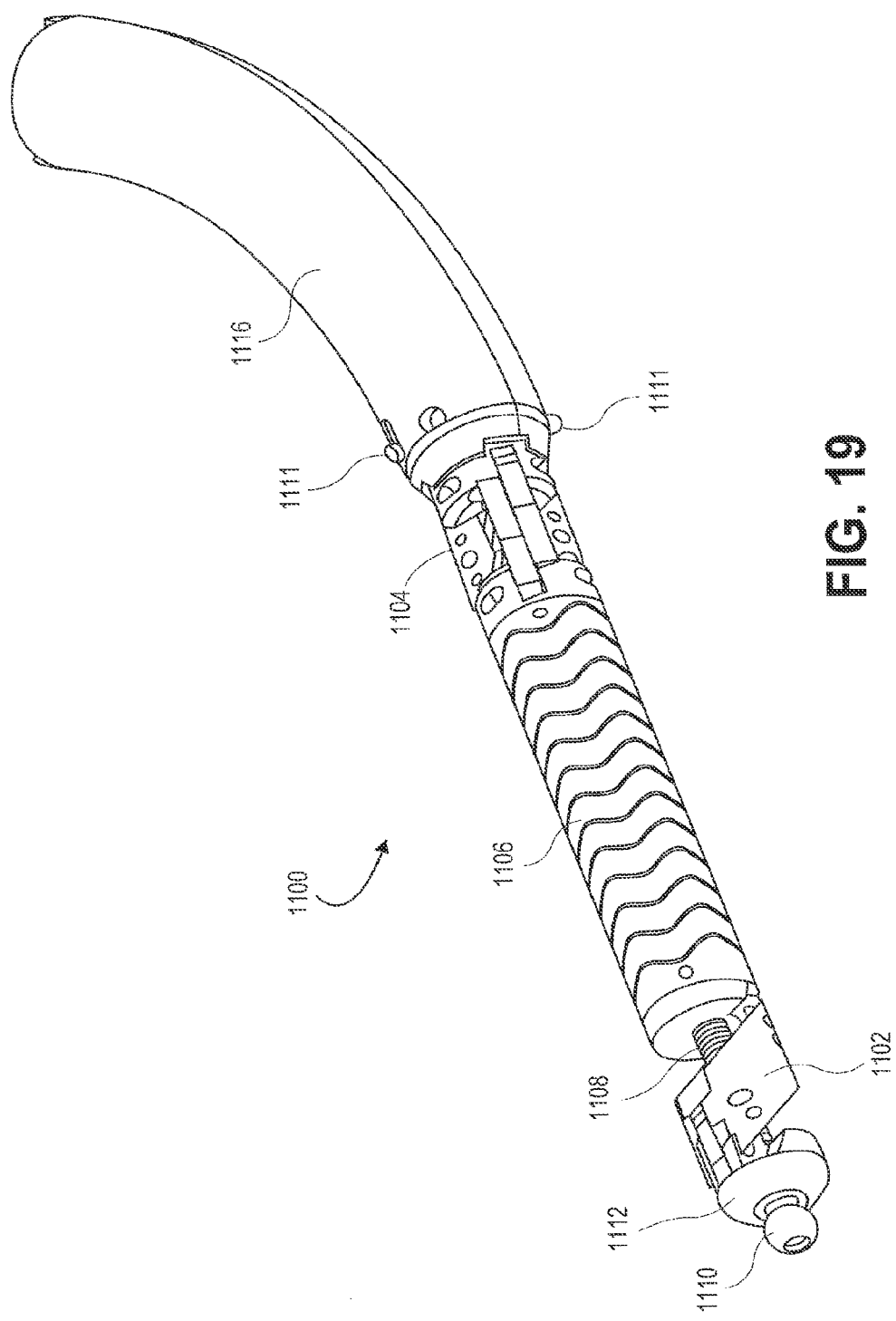
FIGS. 19-21 show yet another embodiment of a fracture fixation device according to the invention.
Figure 20:
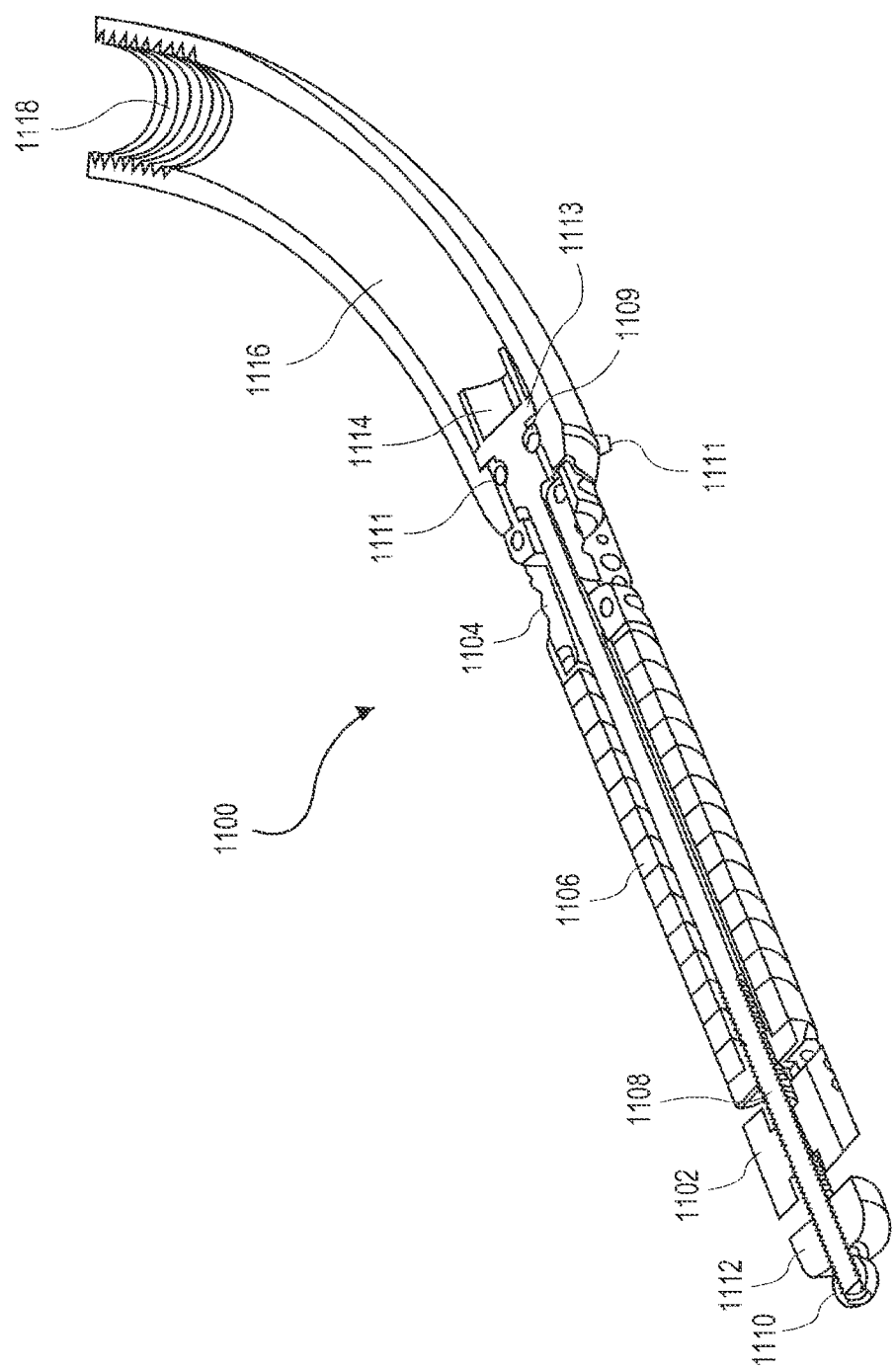
Figure 21:
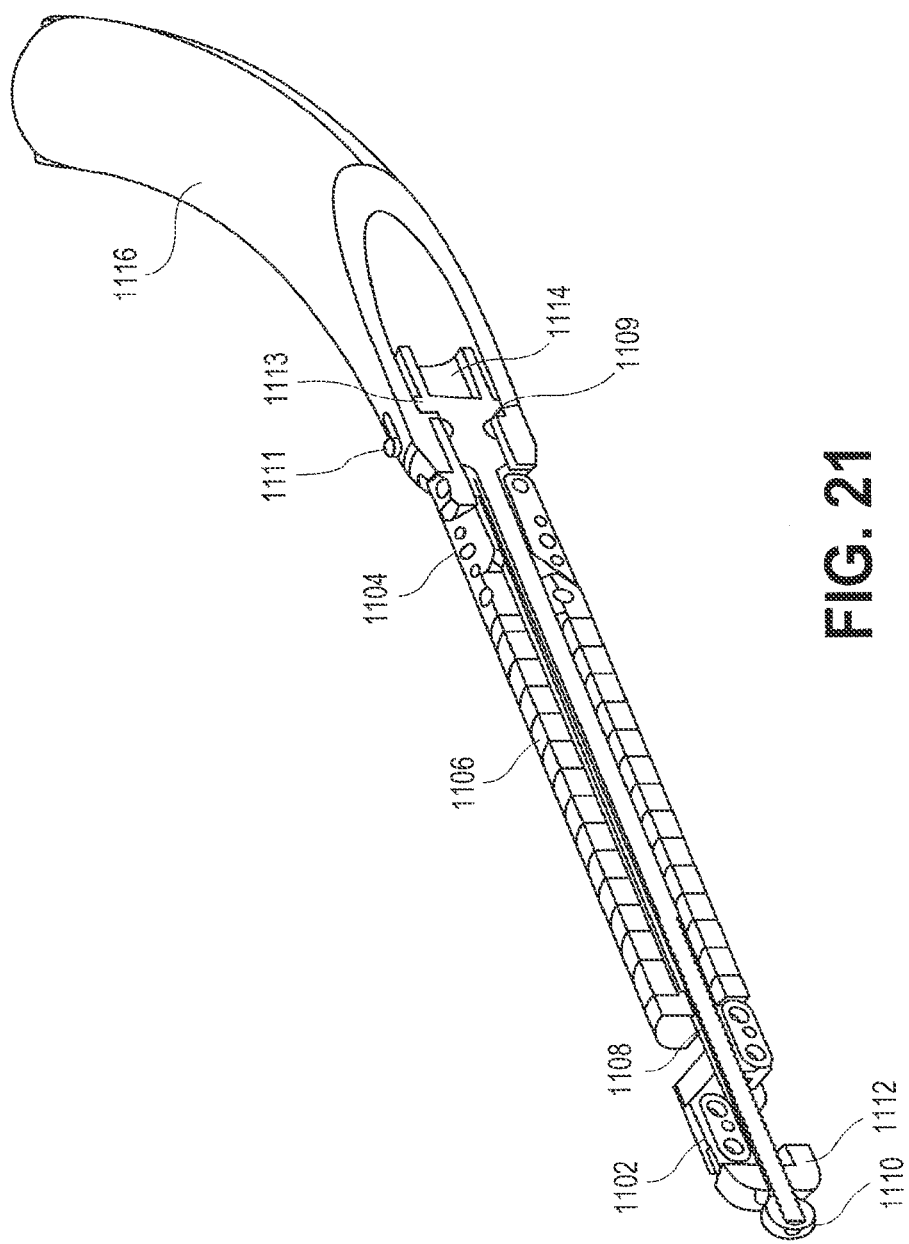

FIGS. 19-21 show yet another embodiment of a fracture fixation device 1100 according to the invention. In this embodiment, device 1100 has a first gripper 1102 constructed, e.g., like the grippers described above with respect to FIGS. 13-18, and a second gripper 1104. Extending between grippers 1102 and 1104 is a flexible-to-rigid body 1106. A threaded actuator 1108 with a blunt end 1110 extends through grippers 1102 and 1104, body 1106 and an internally threaded head 1112. A tool engagement feature 1114 extends from one end of actuator 1108 to enable a screw driver or other tool to rotate actuator 1108 to actuate, foreshorten and rigidize fracture fixation device 1100. A curved hub 1116 is attached to the device distal to gripper 1104 (distal relative to the patient). Pins 1111 secure hub 1116 and actuator 1108 axially to the device while still permitting the actuator to rotate with respect to the device and hub. A flange 1113 formed in tool engagement feature 1114 engages a lip 1109 formed on the inside of hub 1116 to transfer any loads from the actuator directly to the hub to avoid overloading pins 1111. Internal threads 1118 in hub 1116 provide for attachment to a deployment tool (such as, e.g., tool 1300 shown in FIGS. 34-41) or for the insertion of a plug (not shown) after deployment of fracture fixation device 1100 within a fractured bone. Hub 1116 that transverses the fracture is designed with a larger external diameter than the rest of the device. This features in the hub 1116 limits, during the healing process of the fracture, the amount of bone in-growth and calluses that would otherwise prevent the removal of the device. The external diameter of the hub 1116 is preferably also tapered to facilitate the release and removal of the device. The larger diameter of the hub 1116 during withdrawal leaves behind an opening larger than the rest of the device such as the grippers 1104, 1108 and flex-to-rigid body 1106 and thus facilitates the removal of the device.

Figure 22:
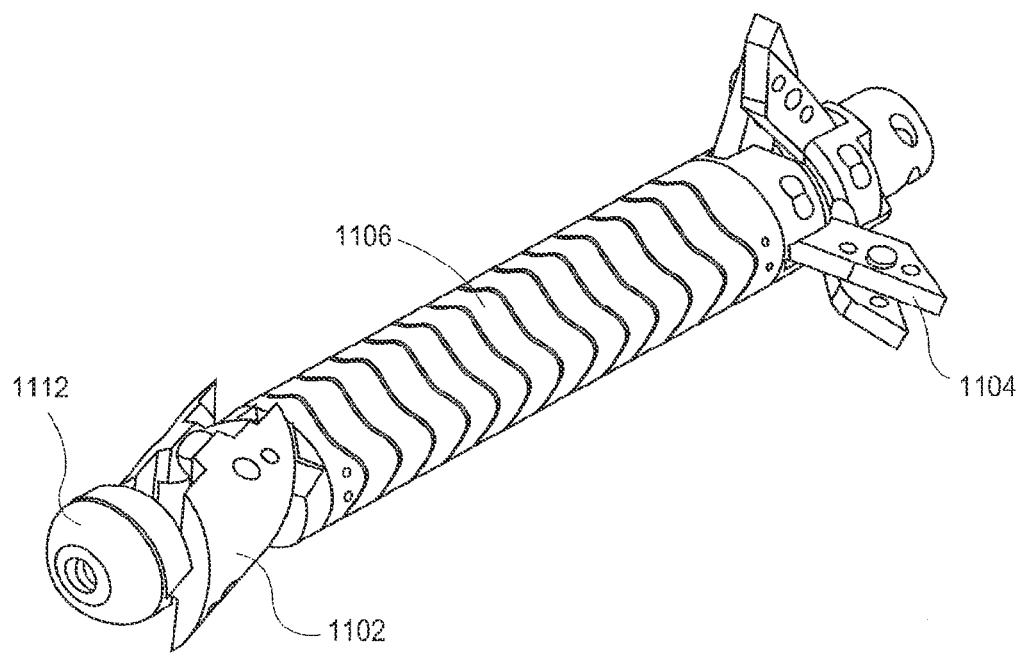
FIG. 22 shows a portion of fracture fixation device of FIGS. 19-21 in a deployed configuration.

FIG. 22 shows device 1100 of FIGS. 19-21 without hub 1116, actuator 1108 and blunt end 110. As shown, grippers 1102 and 1104 are in the deployed configuration.

Figure 23:
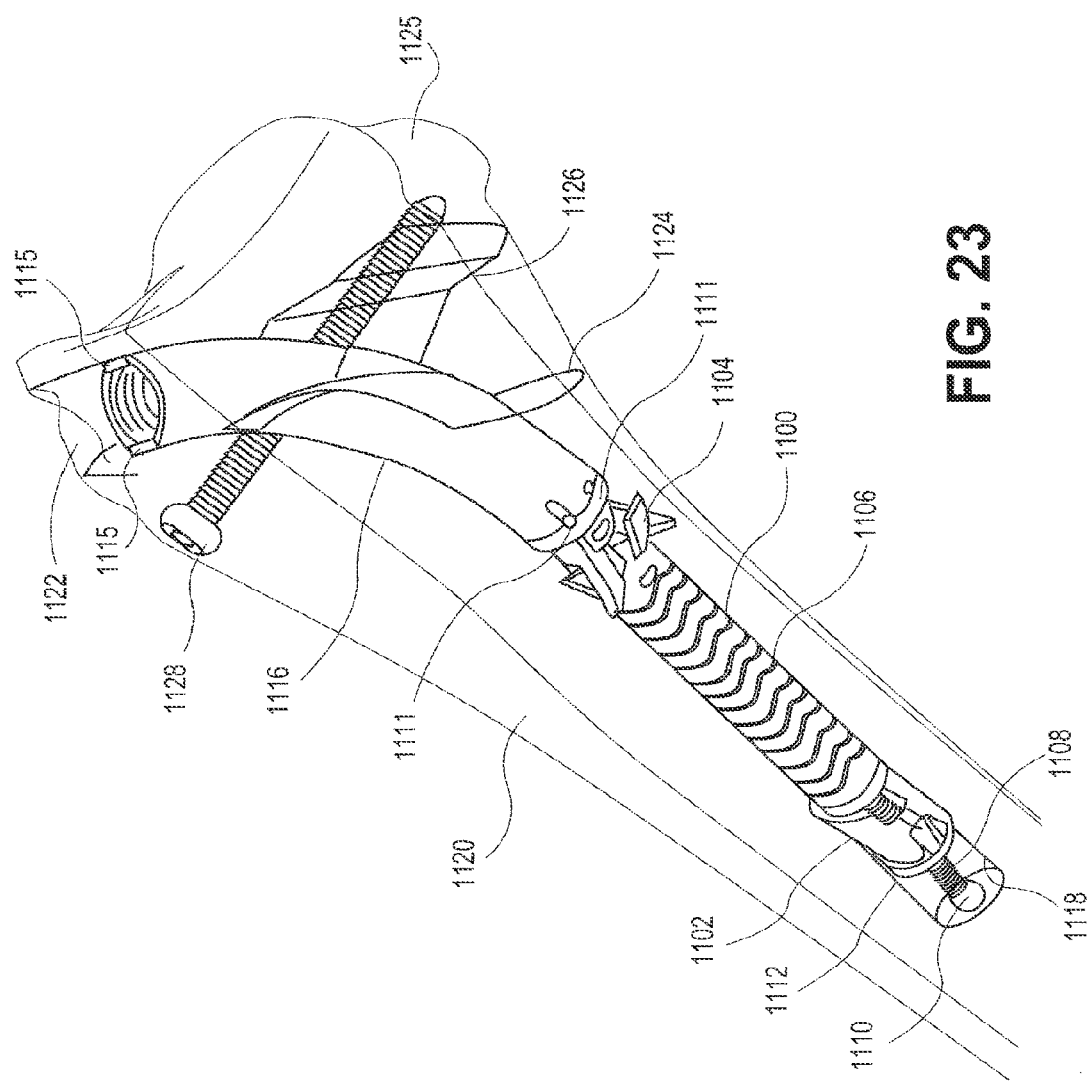
FIGS. 23-25 show the fracture fixation device of FIGS. 19-22 deployed within a bone.
Figure 24:
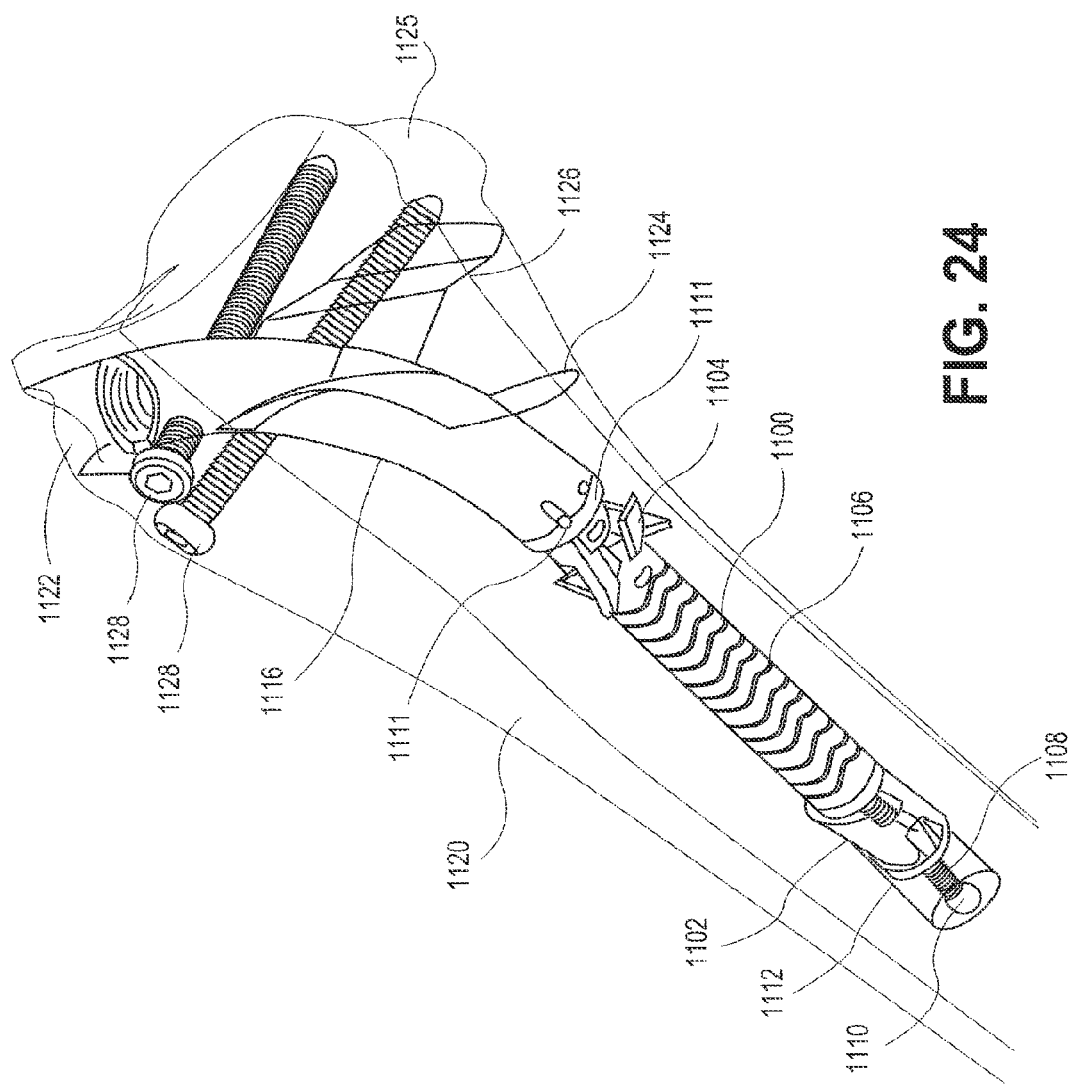
Figure 25:
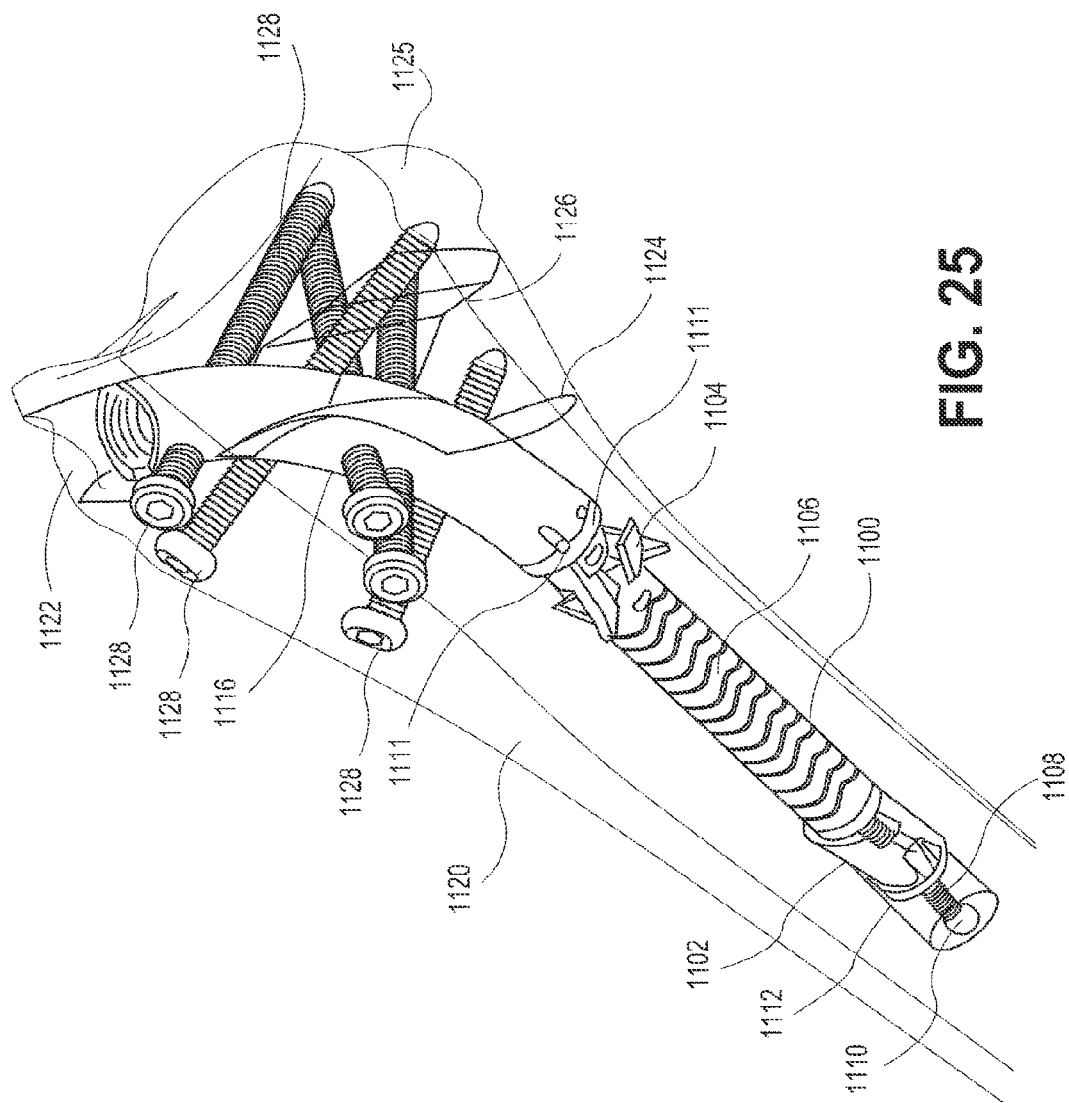

FIGS. 23-25 show fracture fixation device 1100 of FIGS. 19-22 deployed within a space 1118 formed in a bone 1120. Device 1100 has been inserted through an opening 1122 formed in a bony protuberance of bone 1120, and the grippers 1102 and 1104 have been actuated to grip the interior of the bone. Appropriate tools (such as those discussed herein) have been used to form space 1118 with a curved distal portion (distal with respect to the patient) extending proximally from opening 1122 to a substantially straight proximal portion through one or more fracture areas, such as fracture lines 1124 and 1126. As shown, hub 1116 is disposed within the curved portion of space 1118 while flexible-to-rigid body 1106 and the grippers 1102 and 1104 are disposed in the substantially straight portion of space 1118. During delivery to space 1118 in the device's undeployed configuration, grippers 1102 and 1104 and body 1106 are substantially flexible so as to accommodate the curve of the distal portion of the opening. After actuation, however, the device body 1106 becomes rigid through the compression and interaction of its segments during foreshortening and deployment of grippers 1102 and 1104.

In this embodiment, hub 1116 is substantially rigid and has a curve approximating that of the curved portion of opening 1118. In some embodiments of the method of this invention, some or all of hub 1116 is placed on one side of a bone fracture while the remainder of the fracture fixation device is placed on the other side of the fracture.

In some embodiments, hub 1116 is made of PEKK or PEEK implantable grade material and may be injection molded. Using the tools of this invention, a hole through bone 1120 may be drilled at any angle and through any portion of hub to permit a screw to be inserted through the bone and fixation device. In FIG. 23, one screw 1128 has been inserted through hub 1116 to help anchor device 1100 within the bone and to hold bone fragment 1125 to the main portion of the bone 1120. In FIGS. 24 and 25, multiple screws 1128 have been inserted in various positions and orientations. These figures illustrate the ability to place screws wherever needed and at whatever orientation required.

According to aspects of the invention, it has been discovered that placing a screw 1128 through the back of hub 1116 and just below the subchondral bone (superficially and proximally of the subchondral bone) prevents the subchondral bone from moving proximally after removal of the cast. This undesirable subchondral bone migration can otherwise occur when forces from the hand tendons crossing the fracture draws the subchondral bone proximately (relative to the patient) when the hand is used before the bone fracture is completely healed. In some embodiments of the invention, it is preferable to insert at least one screw 1128 in a dorsal to volar direction, and at least one other screw in a volar to dorsal direction, such as shown by the example depicted in FIG. 24. Such an arrangement of screws 1128 may form a cross pattern as shown, or screws 1128 may be generally parallel but in opposing directions. In some embodiments, it is desirable to form a cross pattern so as to capture four cortices of bone around the fracture. A third screw can be added in a more proximal to distal orientation to form a very strong triangle of bone fixation. Screw holes in hub 1116 may be preformed, may be formed in situ, or a combination thereof.

Figure 26:
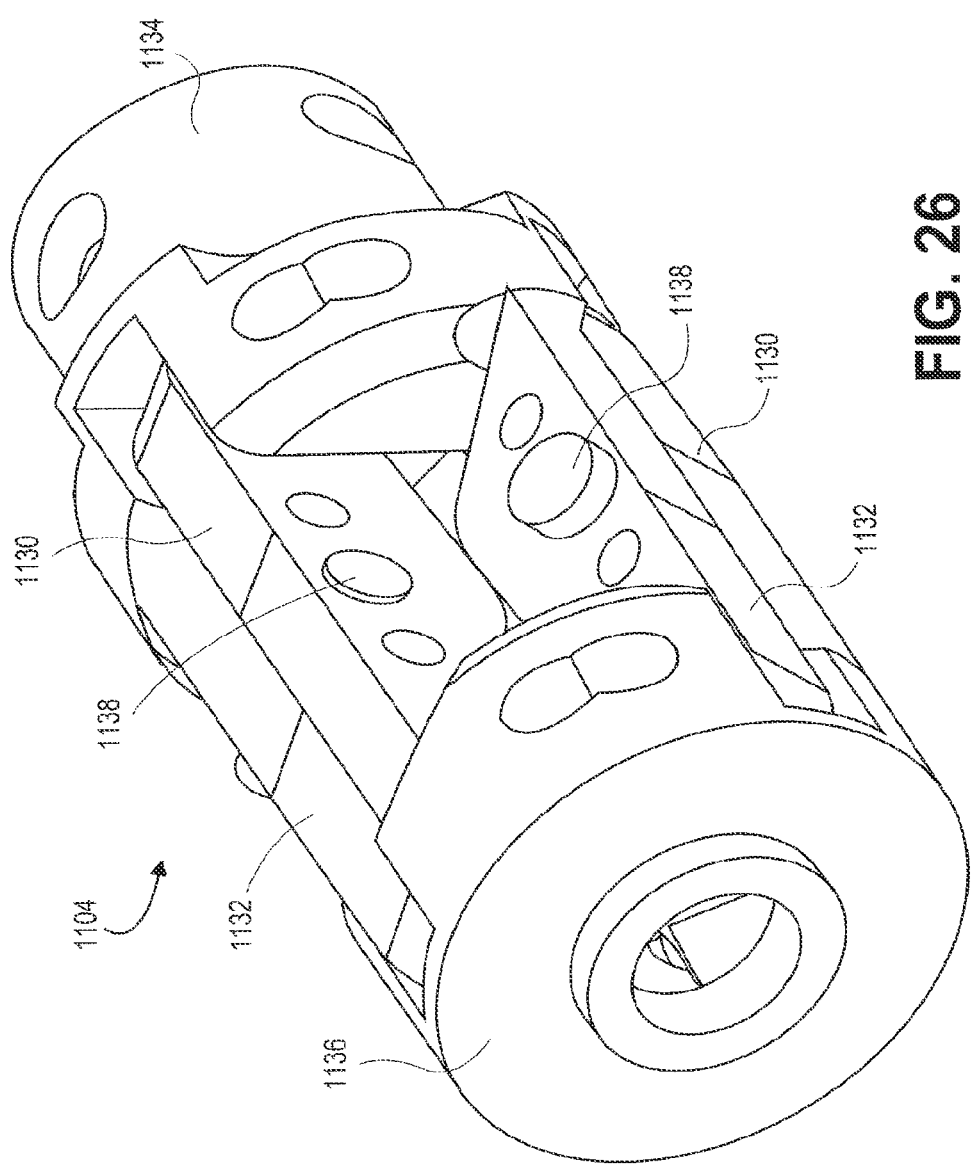
FIGS. 26-31 show details of a gripper for use with a fracture fixation device.
Figure 27:
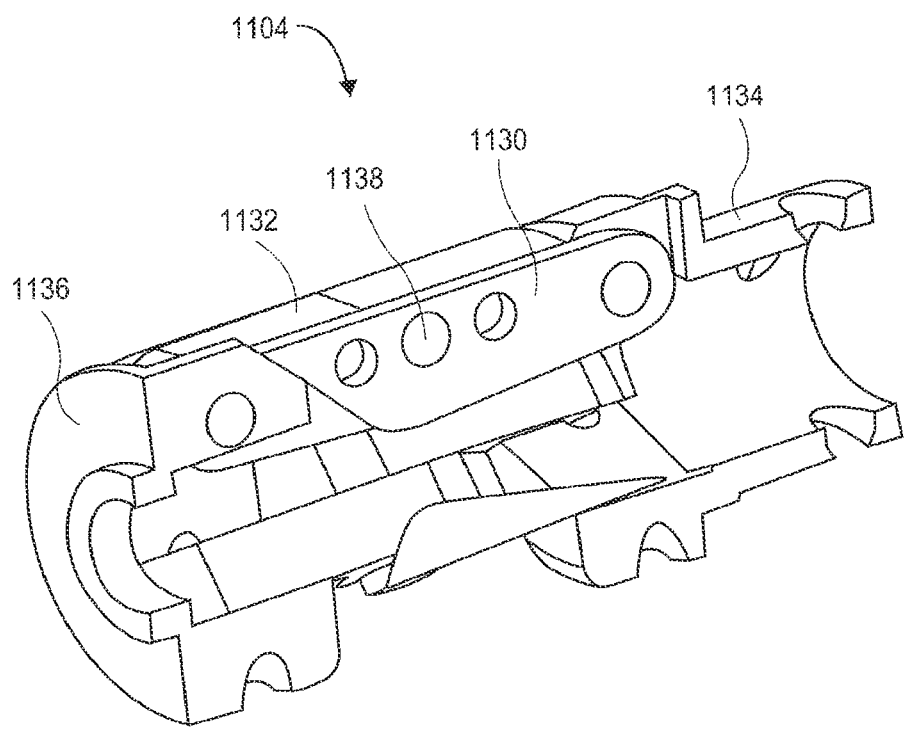
Figure 28:
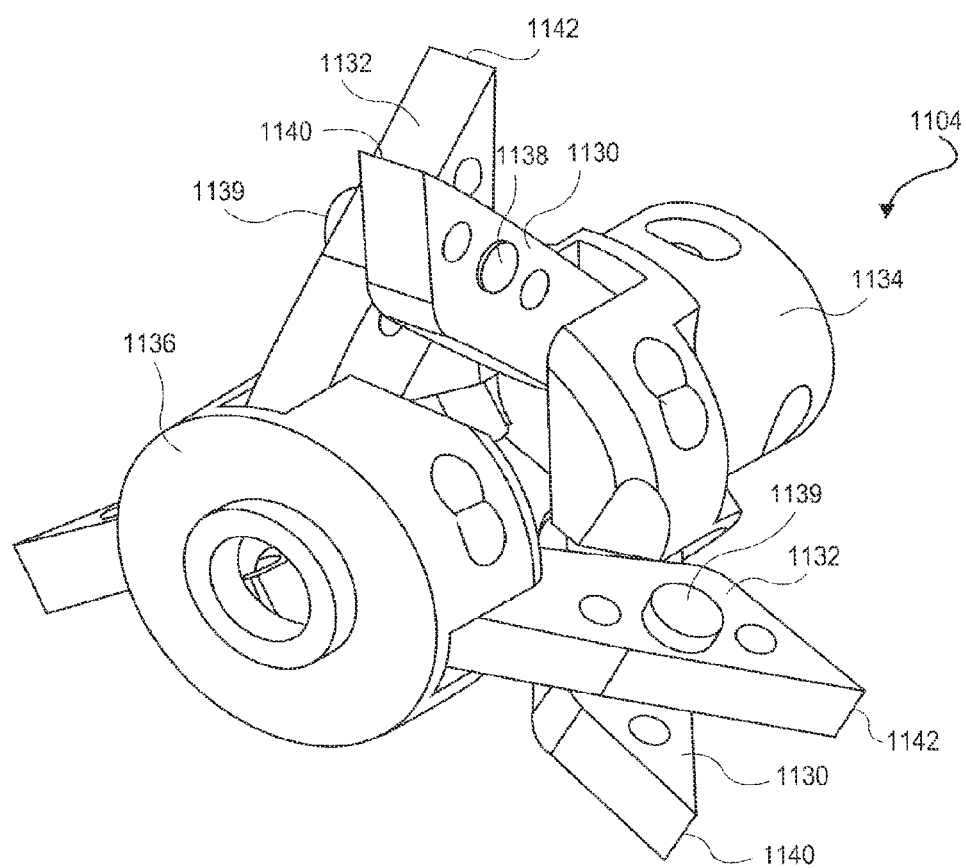
Figure 29:
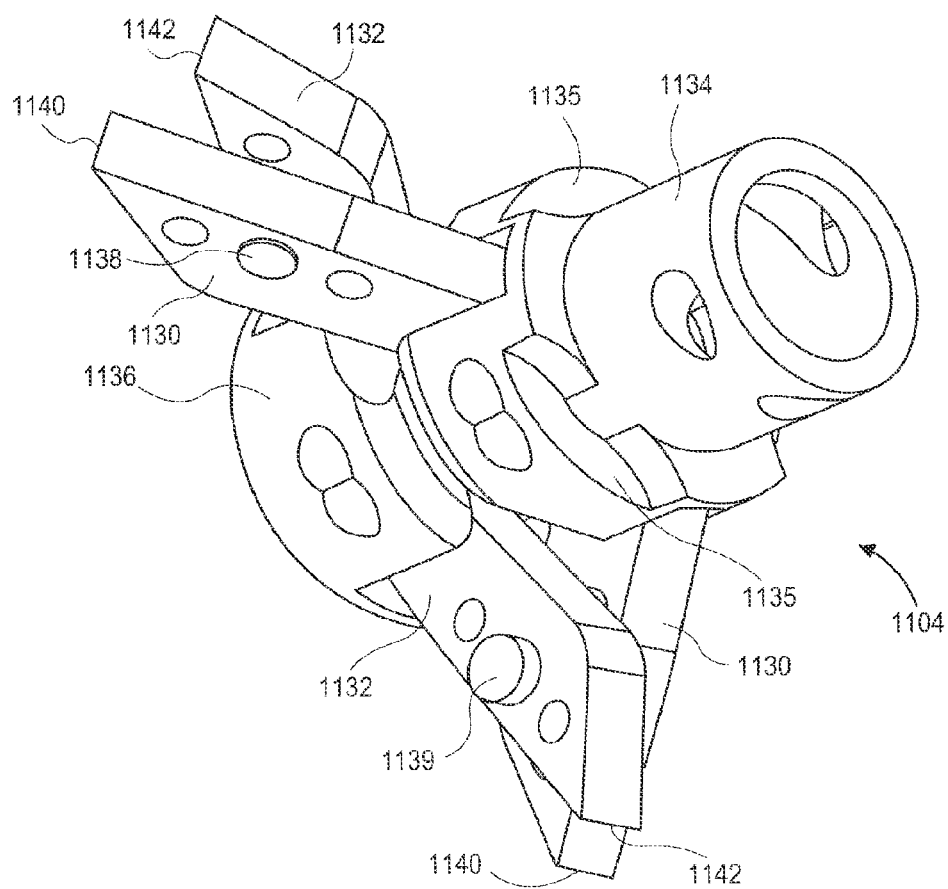
Figure 30:
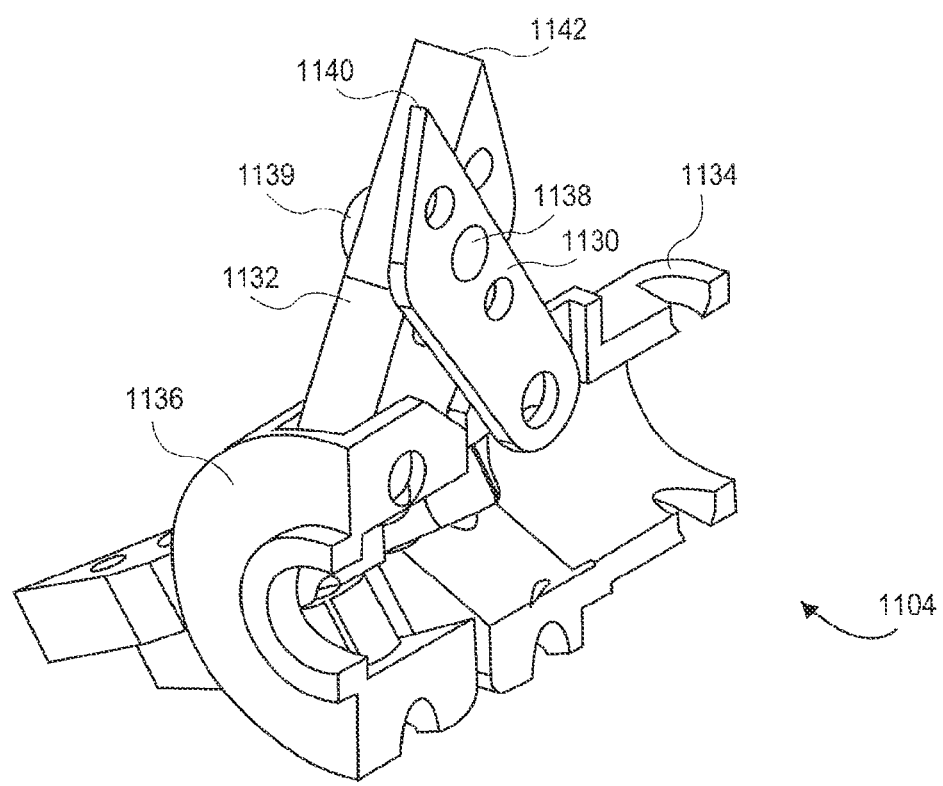
Figure 31:
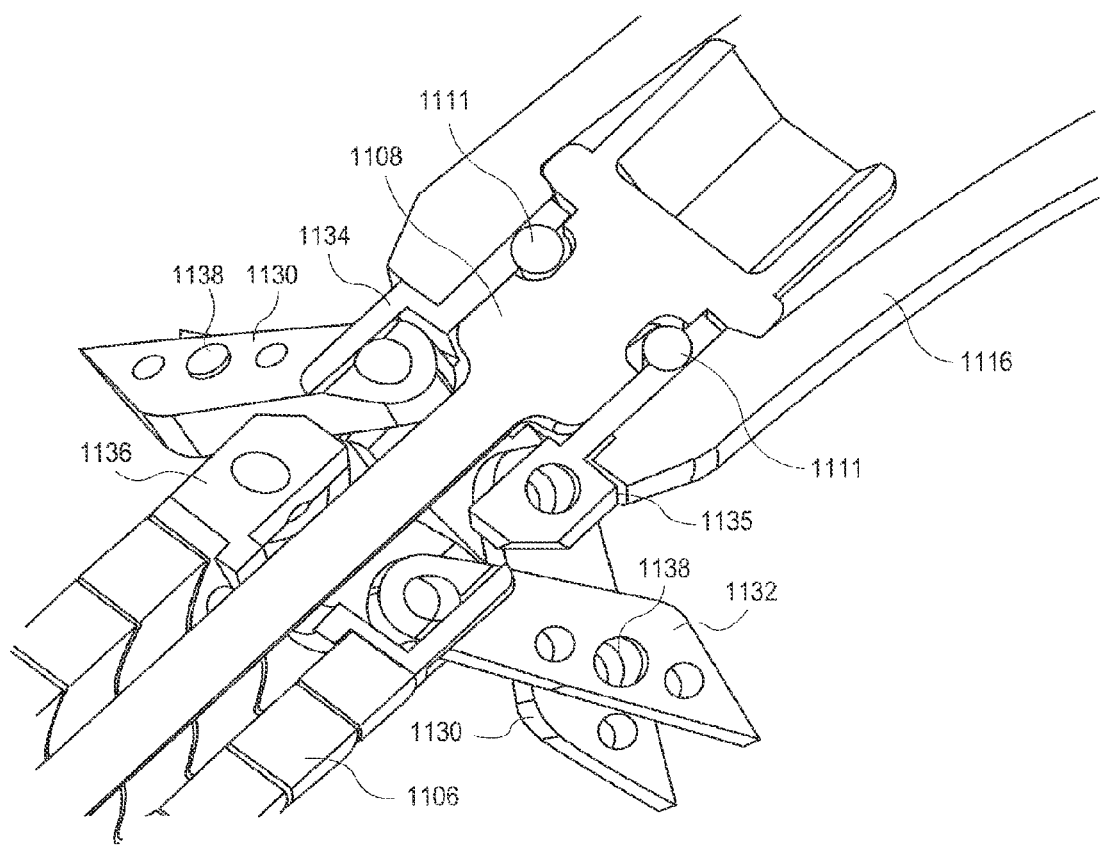

FIGS. 26-31 show details of a gripper 1104 for use with a fracture fixation device, such as the devices of FIG. 1-5, 6-12 or 19-25. FIGS. 26 and 27 show gripper 1104 in an undeployed configuration. FIGS. 28-31 show gripper 1104 in deployed configurations. Gripper 1104 has three sets of anchor elements, with each set including a first anchor leg 1130 and a second anchor leg 1132. Anchor leg 1130 is connected to flange 1134 and extends toward flange 1136, and anchor leg 1132 is connected to flange 1136 and extends toward flange 1134. Legs 1130 and 1132 are rotatably connected by a pin 1138 that is fixedly attached to leg 1130. Leg 1132 rotates freely about pin 1138. A larger head portion 1139 on pin 1138 keeps leg 1132 rotatably mounted on pin 1138. In the undeployed configuration of FIGS. 26 and 27, legs 1130 and 1132 lie substantially parallel to each other within the circular projection of flanges 134 and 136. When the fracture fixation device is actuated by, e.g., turning an actuator 1108 to foreshorten the device (as shown in FIG. 31), flanges 1134 and 1136 are moved closed together. This movement causes the outer edges 1140 and 1142 of legs 1130 and 1132, respectively, to rotate radially outwardly to grip the inside surface of the bone in a deployed configuration, as shown, e.g., in FIGS. 23-25. Movement of flanges 1134 and 1136 away from each other retracts legs 1130 and 1132 toward and into their undeployed configuration for repositioning and/or removal of the device from the bone. Cut-outs 1135 formed in gripper 1104 mate with corresponding shapes in the hub to provide a rotational keying feature enabling the transmission of torque from the hub to the rest of the device without overloading the pins connecting the hub to gripper 1104, as shown in FIGS. 29 and 31.

Figure 32:
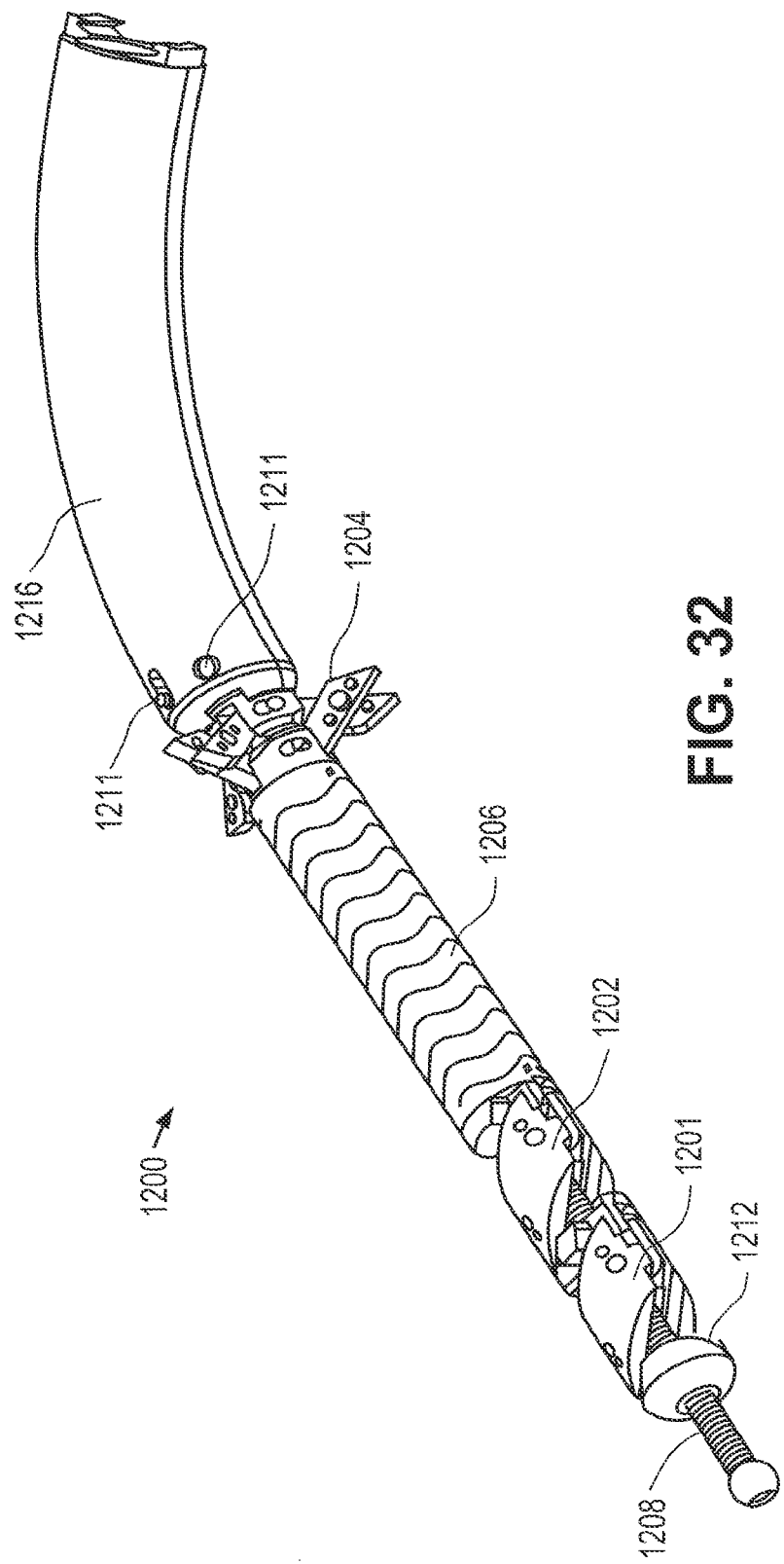
FIGS. 32 and 33 show yet another embodiment of a fracture fixation device according to the invention.
Figure 33:
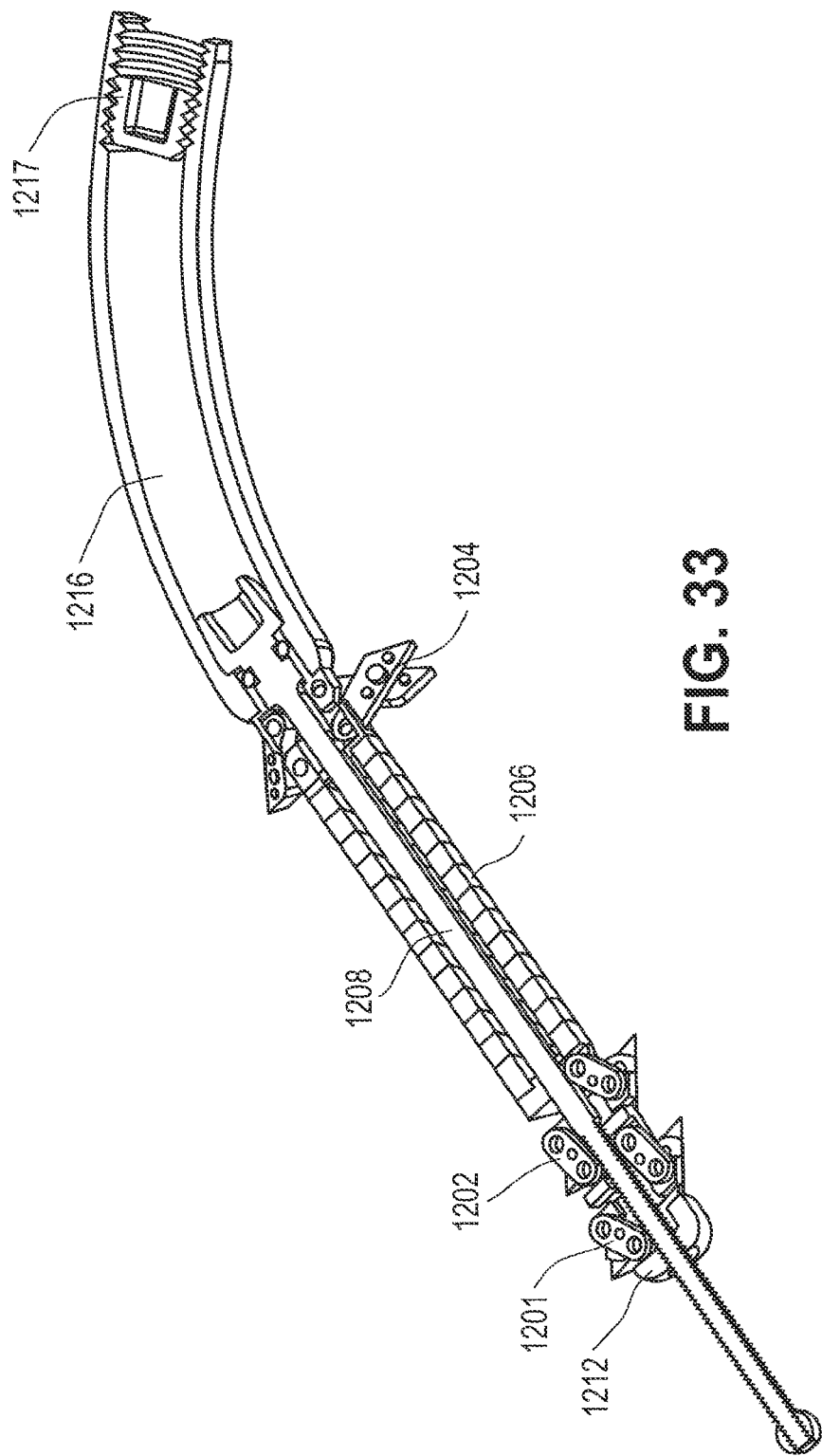

FIGS. 32 and 33 show yet another embodiment of a fracture fixation device according to the invention. Like the embodiment shown in FIGS. 19-31, device 1200 has a curved hub 1216, a distal gripper 1204 (formed, e.g., like gripper 104 of the prior embodiment), a flexible-to-rigid body 1206 and two proximal grippers 1201 and 1202 (each formed, e.g., like gripper 102 of the prior embodiment). Pins 1211 attach hub 1216 to gripper 1204. As in the embodiment of FIGS. 19-31, a threaded actuator 1208 cooperates with an internally threaded head 1212 to foreshorten and actuate the device. The sectional view of FIG. 33 shows a threaded plug 1217 that has been inserted into the distal opening of hub 1216 to seal the device after actuation.

As seen from the discussion above, the devices of this invention can be easily modified by adding grippers or by placing grippers in different positions on the device to address fractures where more gripping forces are needed.

Figure 34:
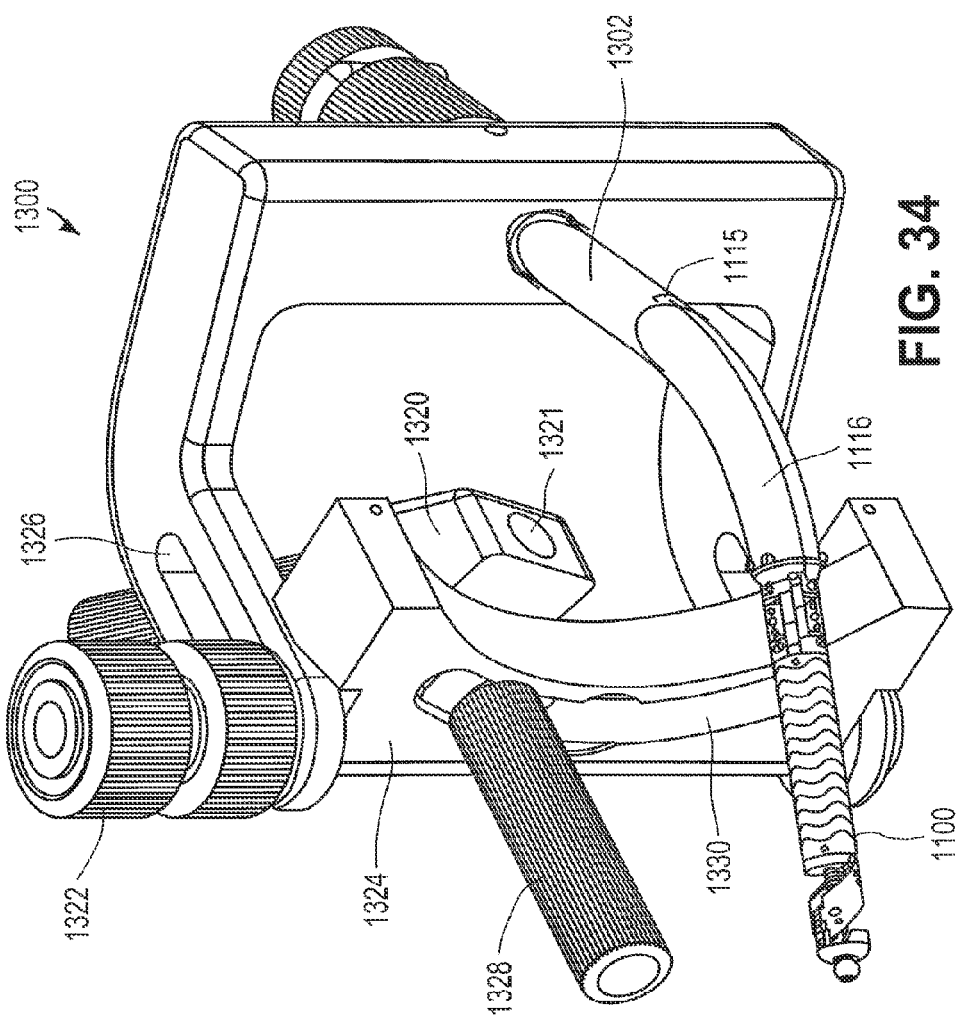
FIGS. 34-39 show a deployment tool for use with a fracture fixation device of this invention.
Figure 35:
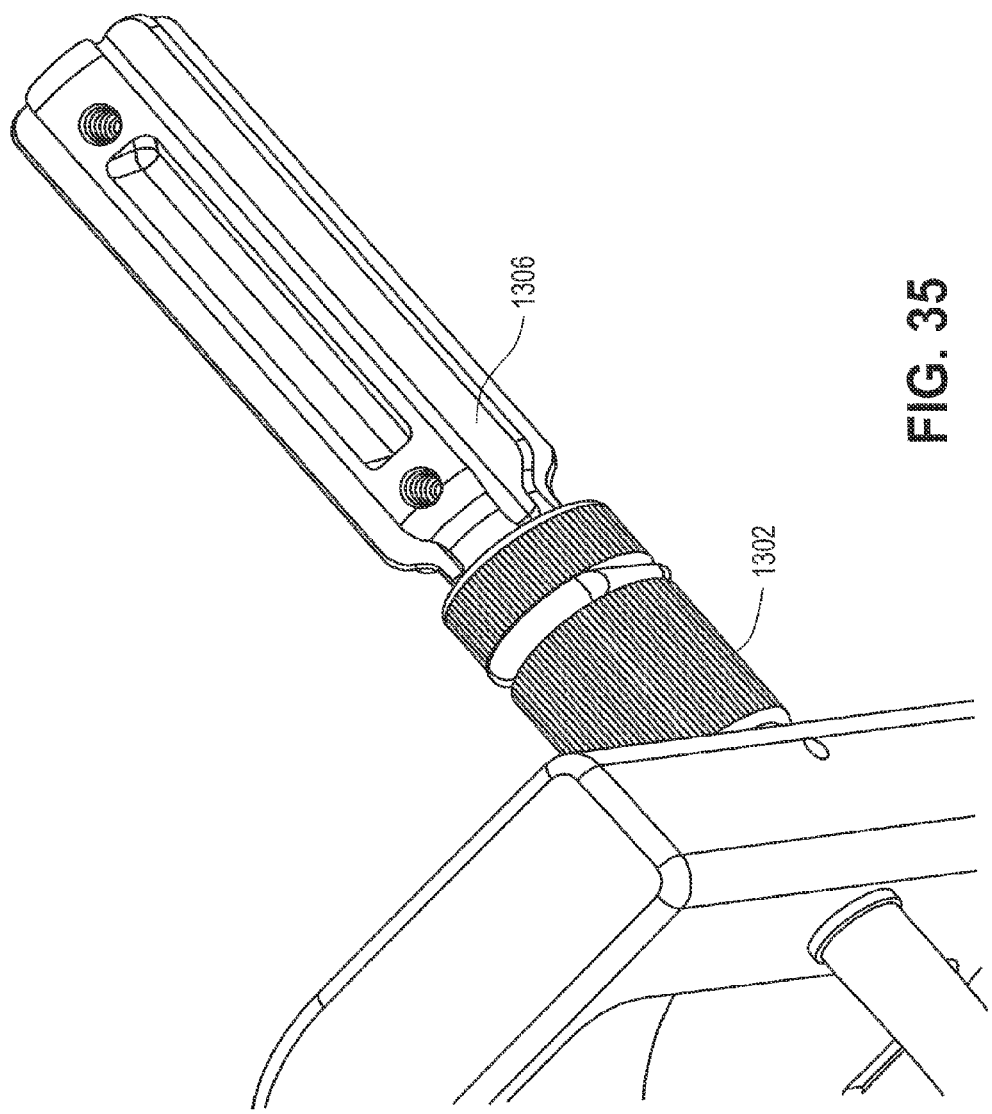

FIGS. 34-39 show a deployment tool 1300 for use with a fracture fixation device 100 of this invention. As shown in FIG. 34, the hub 1116 of fixation device 1100 connects to a stem 1302 of tool 1300. Hub 1116 may be provided with, e.g., alignment features 1115 and attachment features 1114 for this purpose, as shown, e.g., in FIG. 23. This connection orients fixation device 1100 with tool 1300. In particular, tool 1300 aids in the use of a fixation device actuation tool and alignment of a drill with the fixation device's hub after the device has been deployed within a fractured bone and in the insertion of screws into the hub and bone.

Figure 36:
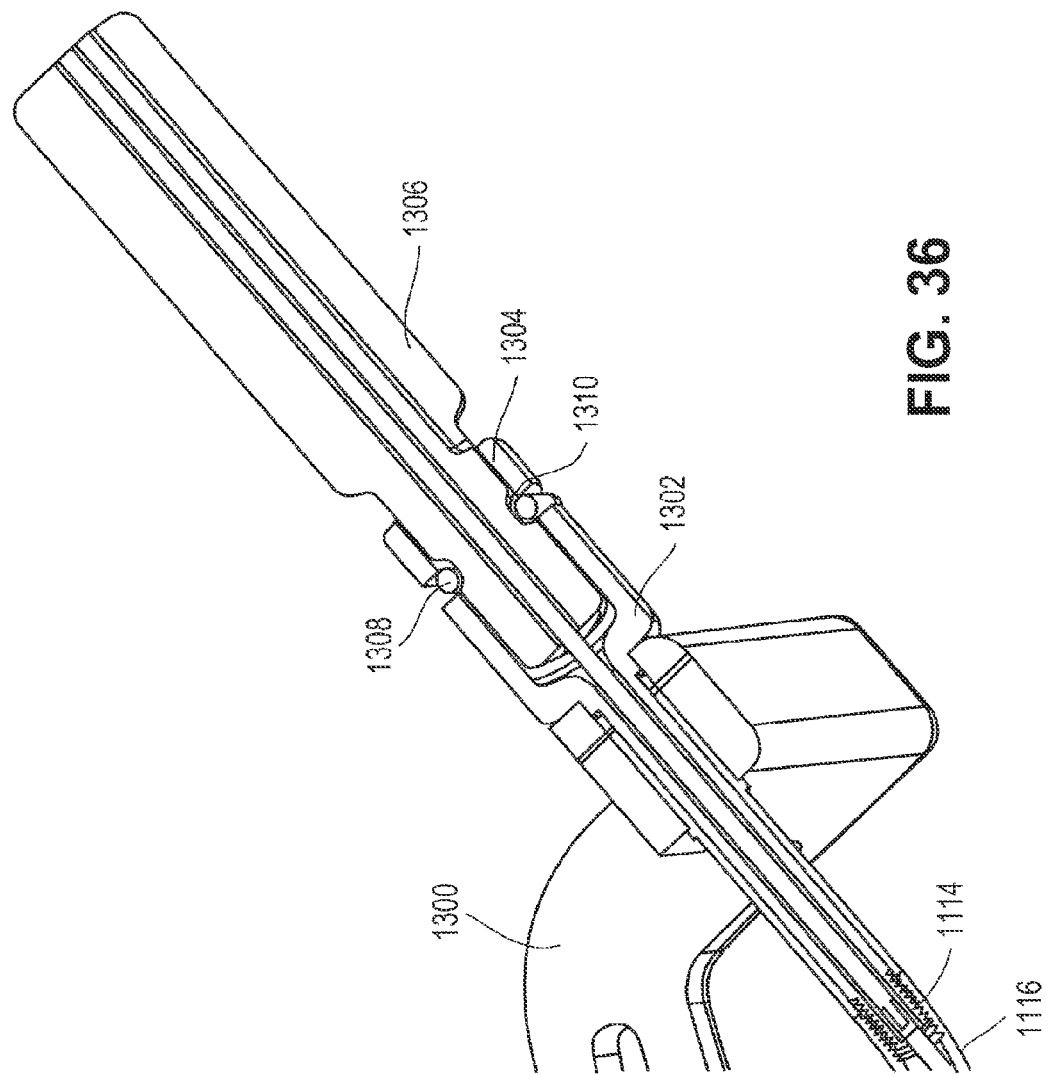
Figure 37:
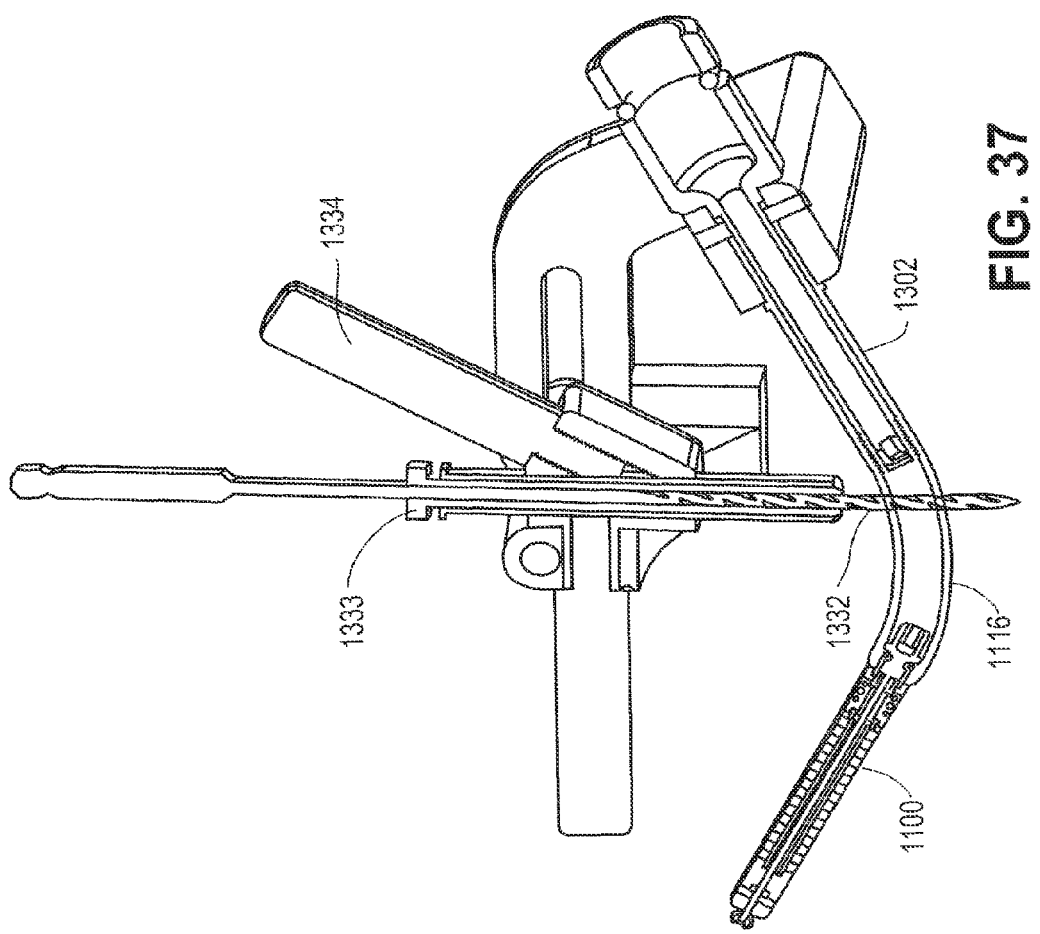
Figure 38:
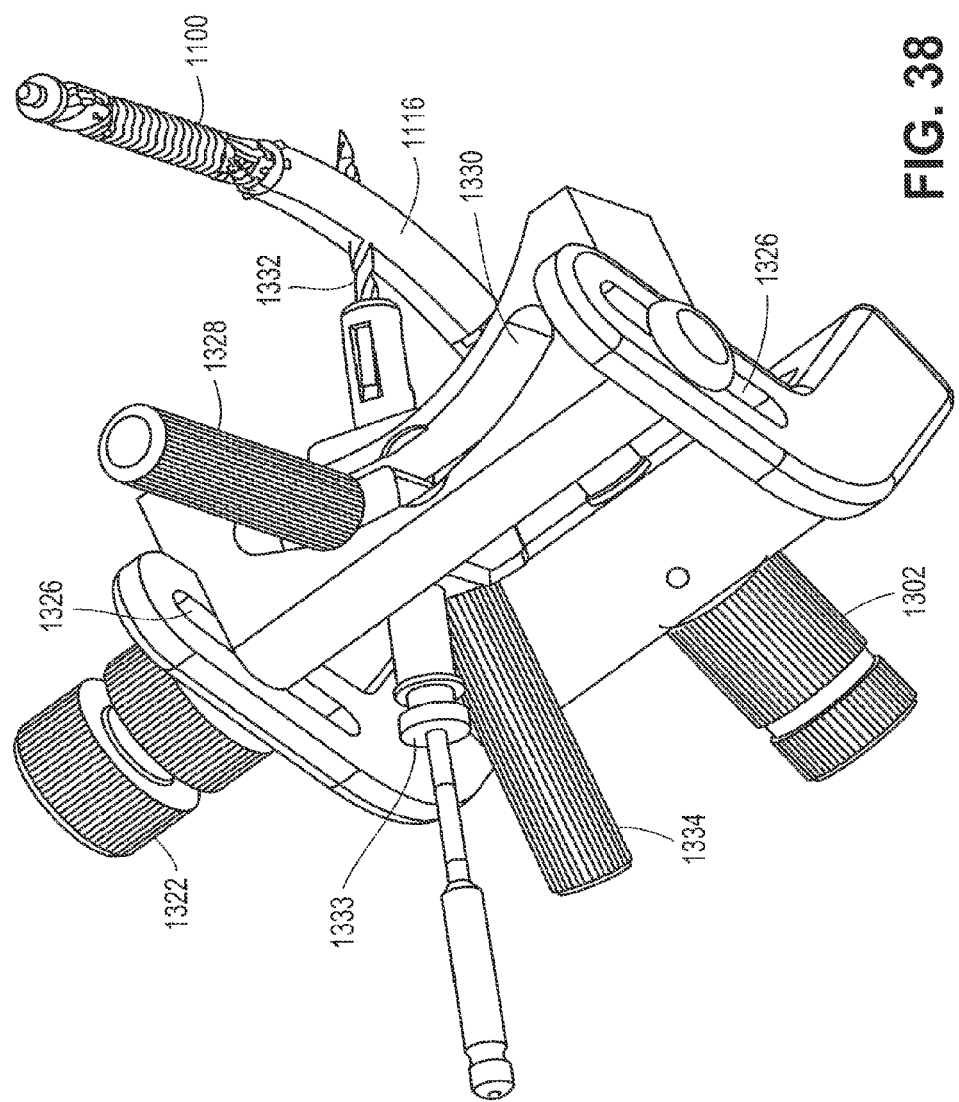
Figure 42:
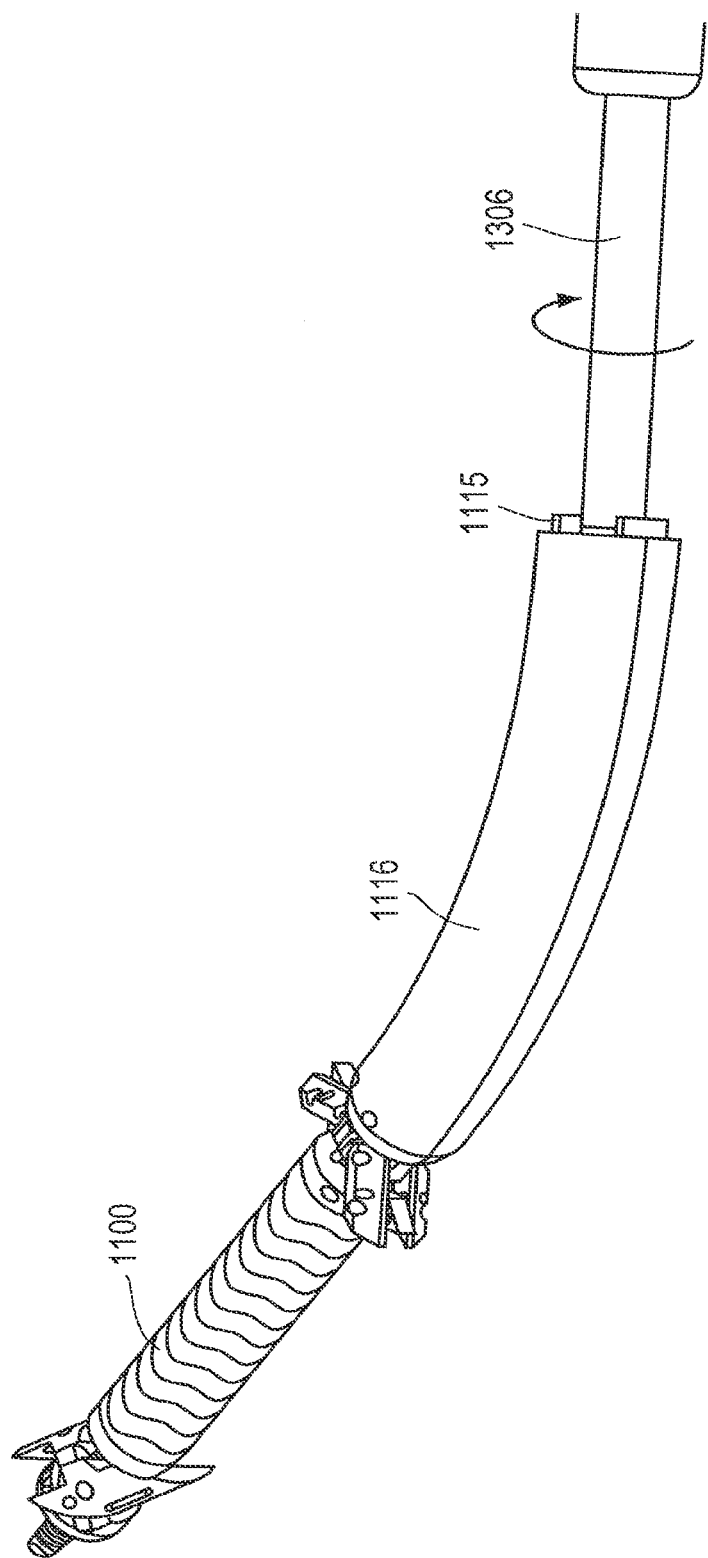
FIGS. 42-43 show the interaction between a flexible screw driver and the actuator of a fixation device.
Figure 43:
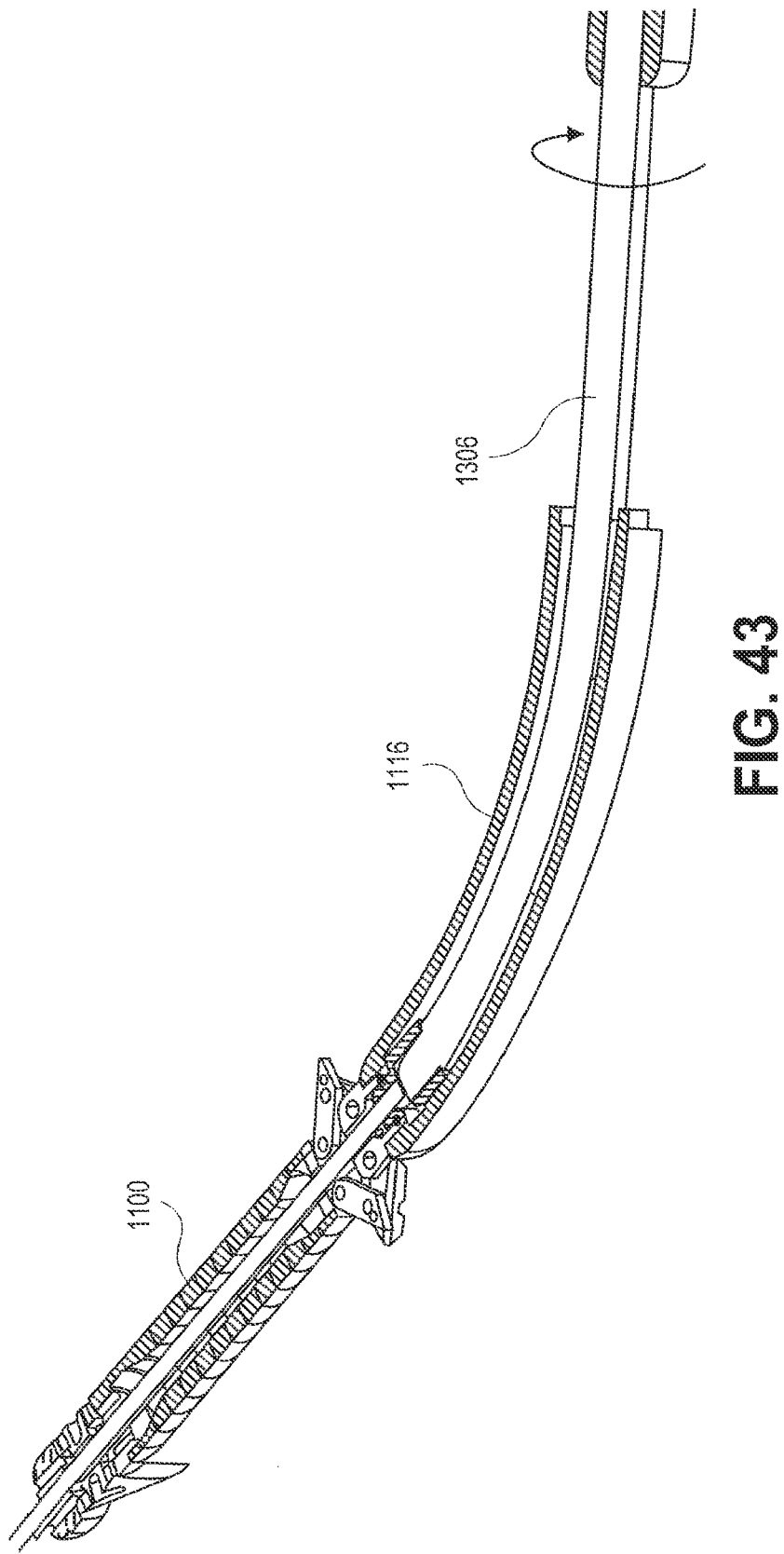
Figure 44:
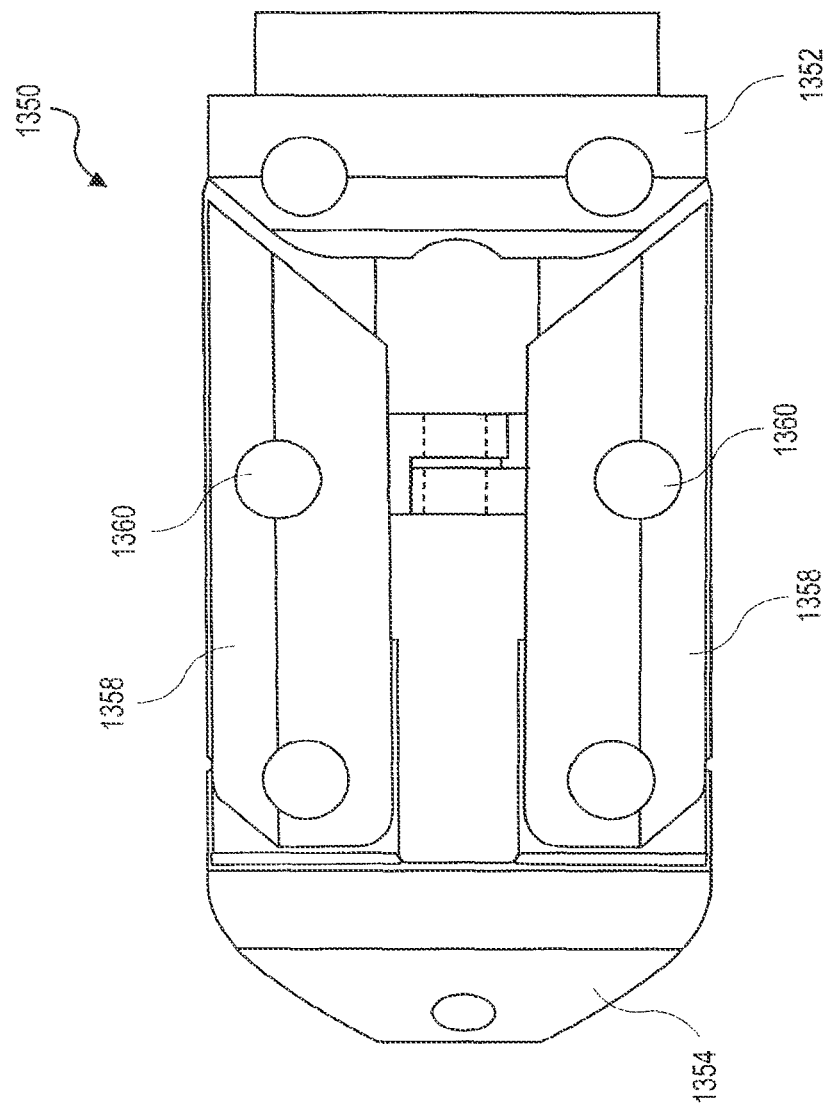
FIGS. 44-48 show another embodiment of a gripper for use with a fracture fixation device.
Figure 45:
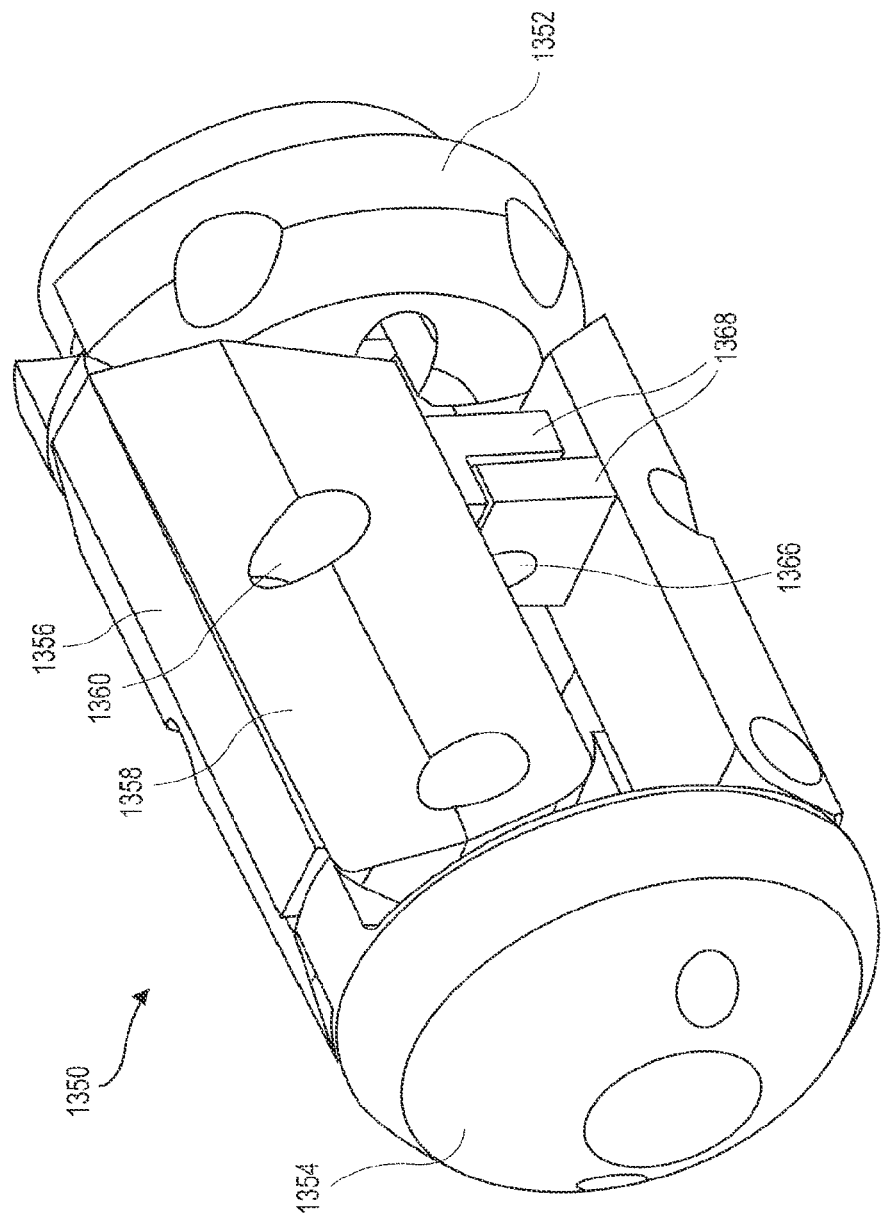
Figure 46:
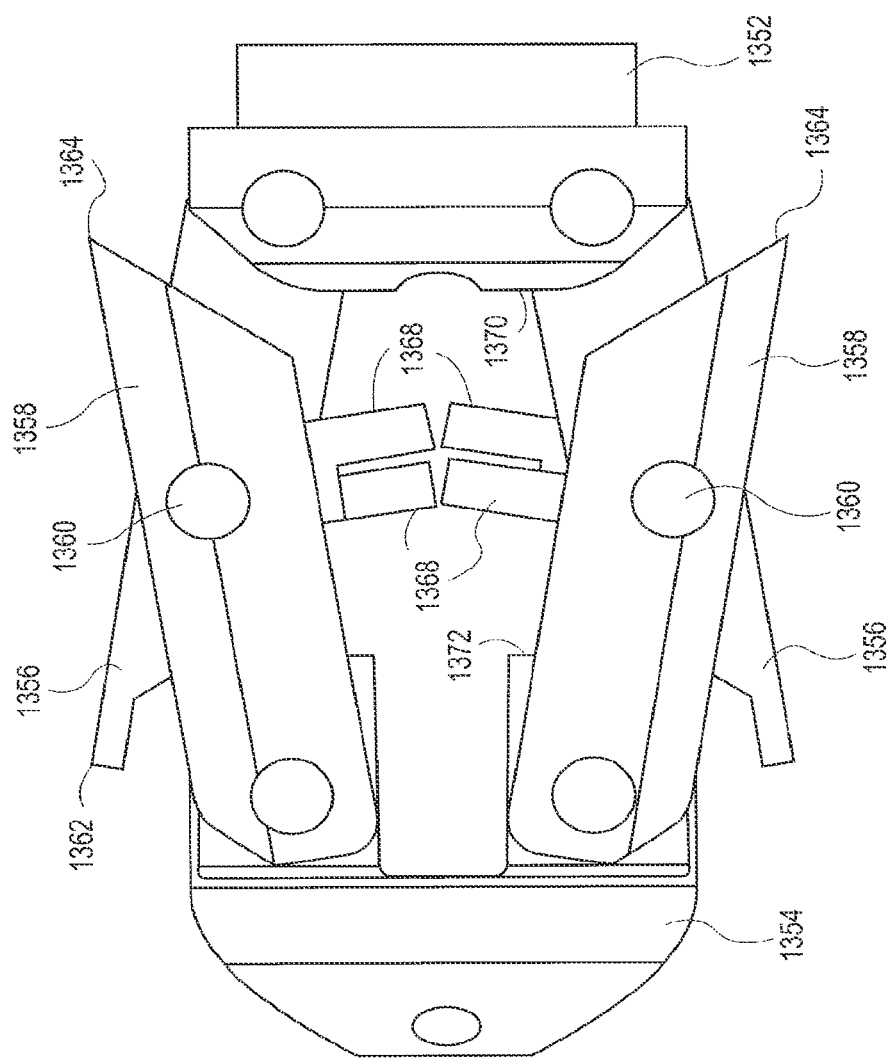
Figure 47:
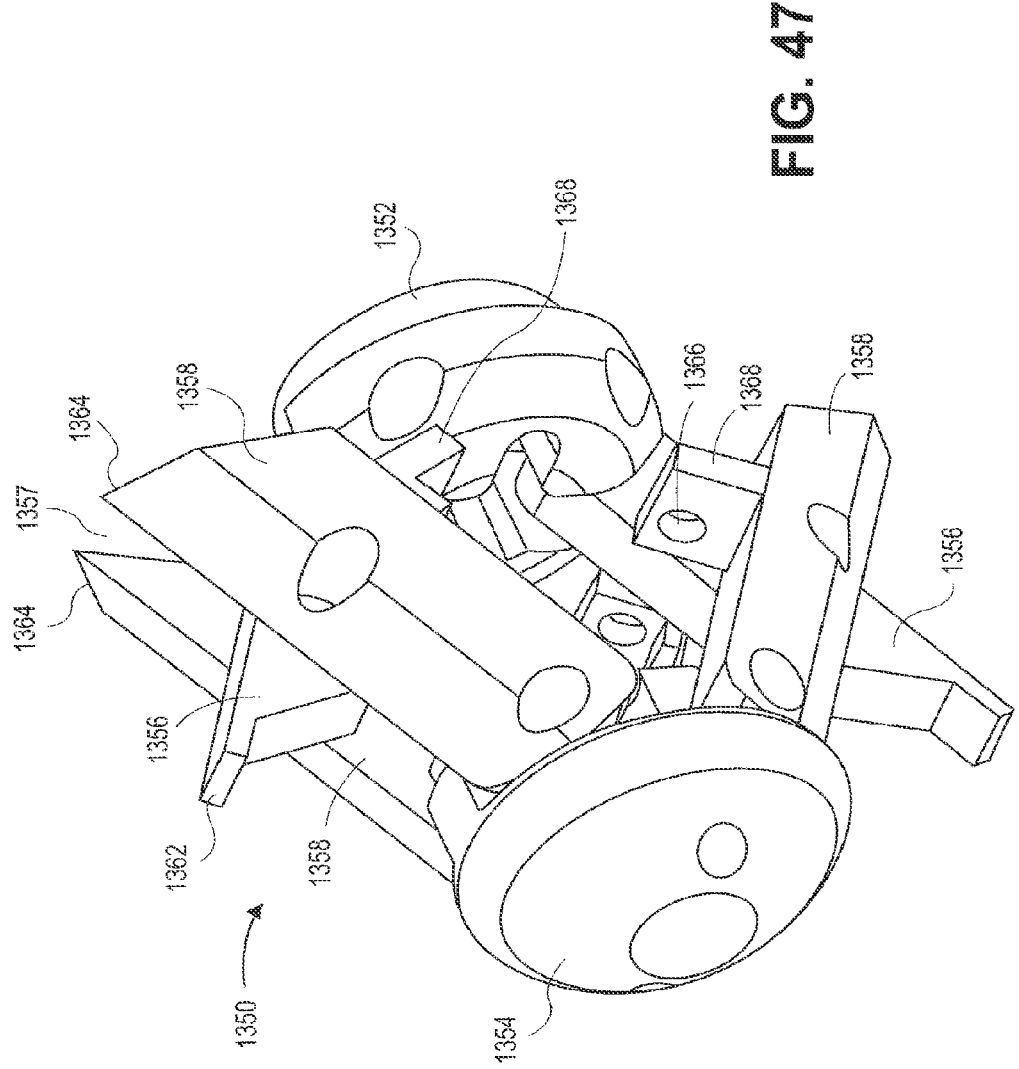

Access to the interior of fixation device 1100 is provided by a port 1304 through stem 1302 so that, e.g., a flexible screw driver 1306 may be inserted through hub 1116 to device feature 1114 of actuator 1108, as shown in FIG. 36. Rotation of flexible screw driver 1306 and actuator 1108 moves device 1100 from an undeployed flexible configuration to a deployed rigid configuration, as shown in FIGS. 42 and 43 (which show the interaction of flexible screw driver 1306 and fixation device 1100 outside of tool 1300). A flexible ring 1308 may be provided to interact with a groove 1310 formed in flexible screw driver 1306 to provide proper axial positioning between the screw driver and the tool engagement feature 1114 of actuator 1108 while still permitting the flexible screw driver to rotate.

Tool 1300 also helps orient a drill and enables it to find the hub of the fixation device even when the fixation device is inside the bone and cannot be seen by a user. When fixation device 1100 is properly attached to stem 1302, the bore 1321 of drill guide 1320 points toward the device's hub 1116 even when the drill guide is rotated along curved guide 1300 or translated along grooves 326. In order to provide the user with flexibility in drill placement (e.g., in order to place one or more screws through hub 1116 as shown in FIGS. 23-25), tool 1300 permits drill guide 1320 to be moved with respect to stem 1302 and attached hub 1116. Drill guide 1320 may be translated proximally and distally with respect to hub 1116 by loosening knob 1322 and moving support 1324 along grooves 1326. In addition, drill guide 1320 may be rotated about hub 1116 by loosening knob 1328 and moving drill guide 1320 along curved groove 1330.

Figure 39:
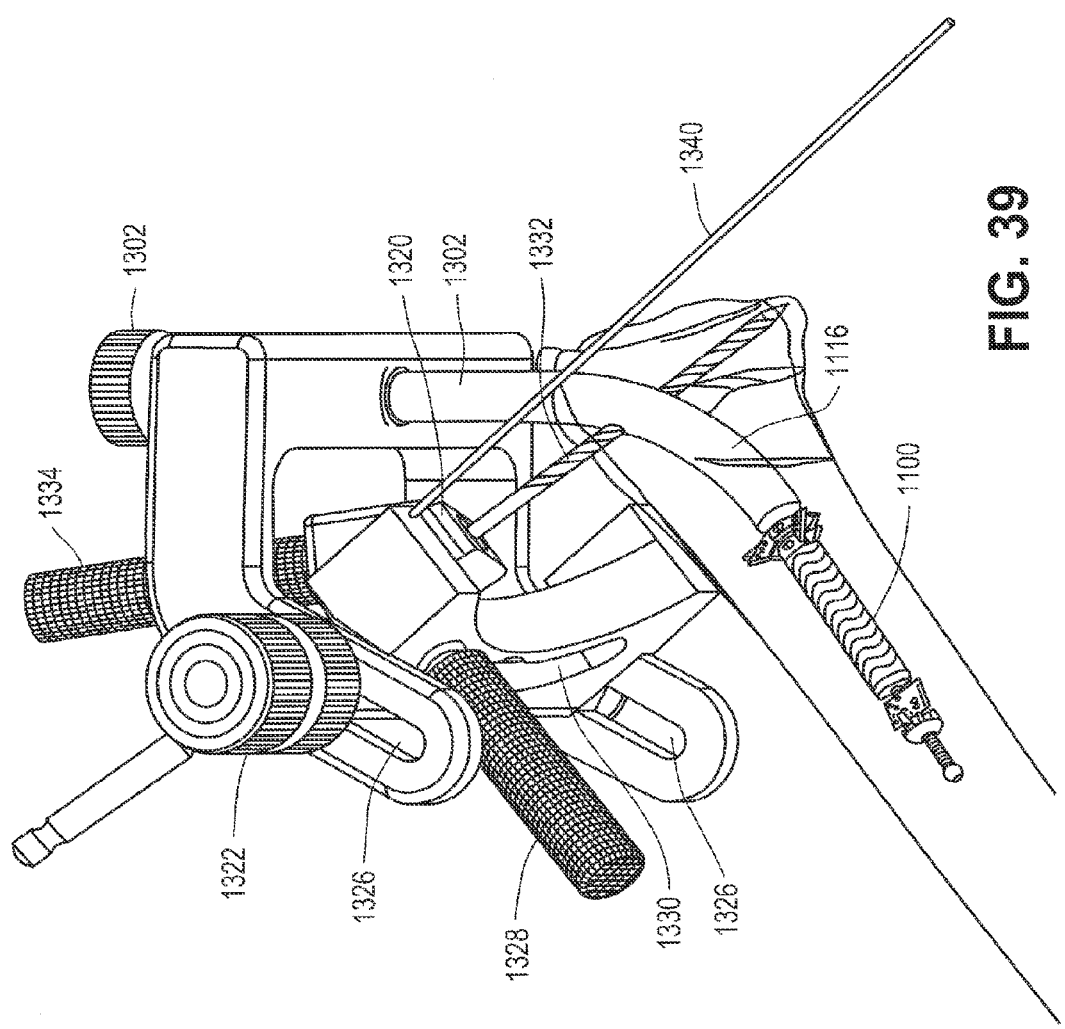
Figure 40:
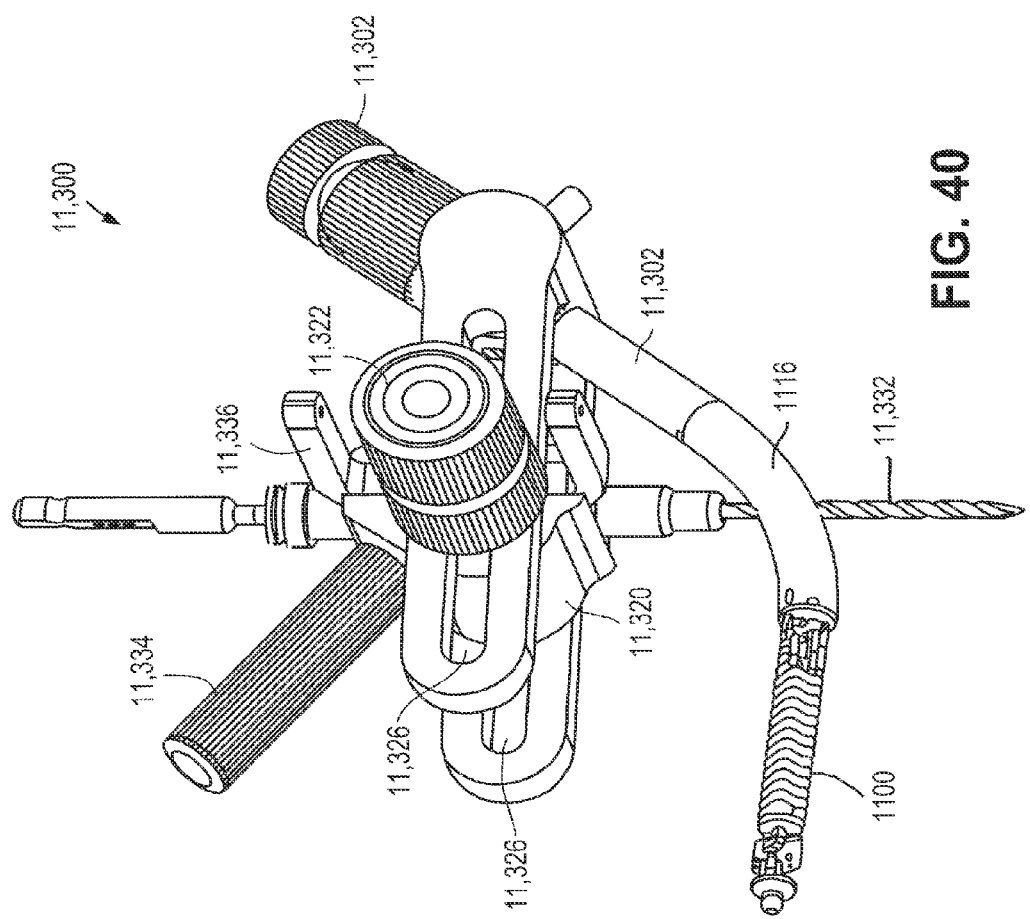
FIGS. 40-41 show another embodiment of a deployment tool for use with a fracture fixation device of this invention
Figure 41:
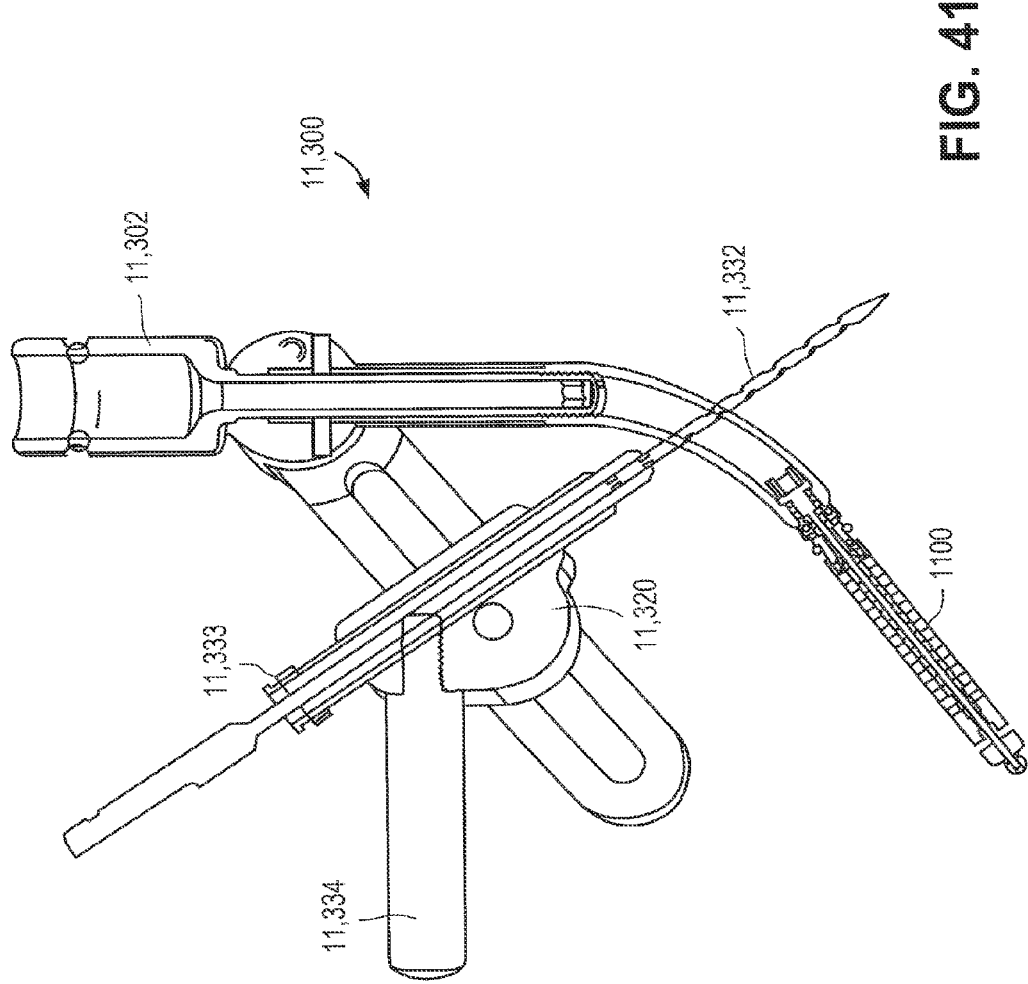

FIGS. 37-41 show tool 1300 being used to guide a drill 1332 toward and through hub 116 (and through the bone, as shown in FIG. 41). The drill sleeve 1333 surrounding drill bit 1332 is held in place within bore 1321 by a thumb screw 1334. An external x-ray visible aim 1340 may extend from drill guide 1320 to show on x-rays the orientation of the drill bit 1332 and projected trajectory within the patient's bone, as shown in FIG. 39. The drill bit may be provided with a scale to show depth of the drilled hole and, therefore, the length of the screw needed. In some embodiments, the drill 332 may have a sharp tip to reduce skittering of the drill against the device hub and/or bone during drilling. The tip included angle may be less than 100.0 degree. and preferably between 25.0 degree. and 35.0 degree. to ensure penetration of the hub.

FIGS. 40-41 show an alternative planar tool 11300 being used to guide a drill 11332 toward and through the hub 1116 of a fracture fixation device. As with the earlier embodiment, access to the interior of fixation device 1100 is provided by a port 11304 through a stem 11302 so that, e.g., a flexible screw driver may be inserted through hub 1116 to device actuator 1108. A flexible ring 11308 may be provided to interact with a groove formed in the flexible screw driver to provide proper axial positioning between the screw driver and the tool engagement feature 1114 of actuator 1108 while still permitting the flexible screw driver to rotate.

Like the deployment tool described above, tool 11300 also helps orient a drill and enables it to find the hub of the fixation device even when the fixation device is inside the bone and cannot be seen by a user. When fixation device 1100 is properly attached to stem 11302, the bore of drill guide 11320 points toward the device's hub 1116 even when the drill guide is translated along grooves 11326 or is rotated above the axis of knob 11322. In order to provide the user with flexibility in drill placement (e.g., in order to place one or more screws through hub 1116 as shown in FIGS. 23-25), tool 11300 permits drill guide 11320 to be moved with respect to stem 11302 and attached hub 1116. Drill guide 11320 may be translated proximally and distally with respect to hub 1116 by loosening knob 11322 and moving support drill guide 11320 along grooves 11326. In addition, drill guide 11320 may be rotated about stem 11302 and hub 1116.

FIGS. 44-48 show another embodiment of a gripper 1350 for use with a fracture fixation device. As shown, gripper 1350 is designed to be used on the leading end of the fixation device. It should be understood that this gripper could be used at other points in the fixation device as well.

Figure 48:
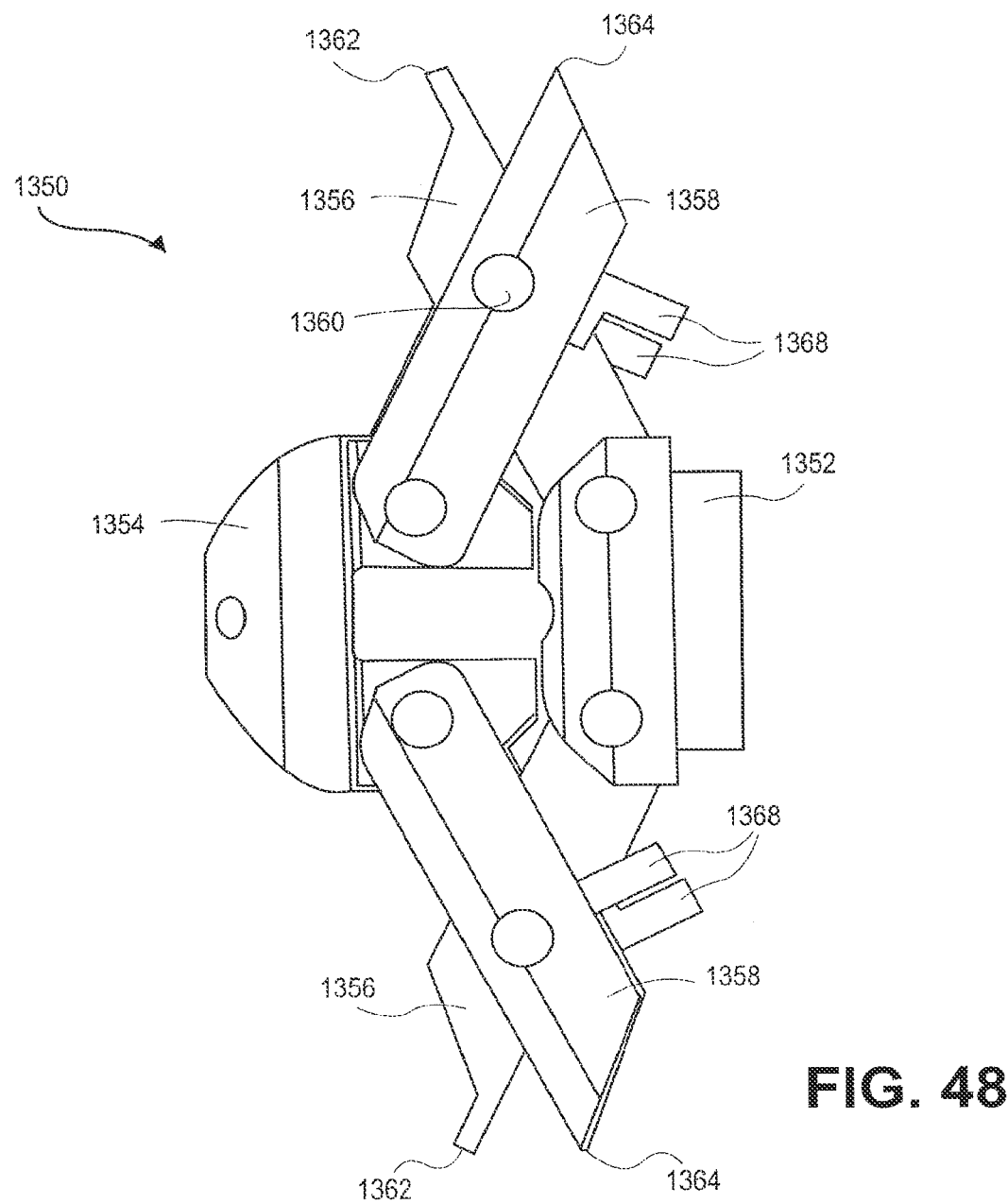

Extending between flange 1352 and nose cone flange 1354 are two sets of anchor elements. Anchor legs 1356 are rotatably attached to flange 1352 and extend toward flange 1354, and split anchor legs 1358 are rotatably attached to nose cone flange 1354 and extend toward flange 1352. Anchor legs 1356 are disposed in the split 1357 of anchor legs 1358. Legs 1356 and 1358 are rotatably connected by a pin 1360. In the undeployed configuration of FIGS. 44 and 45, legs 1356 and 1358 lie substantially parallel to each other within the cylinder of flanges 1352 and 1354. When the fracture fixation device is actuated by, e.g., turning an actuator to foreshorten the device, flanges 1352 and 1354 are moved closer together. This movement causes the outer edges 1362 and 1364 of legs 1356 and 1358, respectively, to rotate outward to grip the inside surface of the bone in a deployed configuration, as shown, e.g., in FIGS. 46-48. Movement of flanges 1352 and 1354 away from each other retracts legs 1356 and 1358 toward and into their undeployed configuration for repositioning and/or removal of the device from the bone. A lock wire (shown in phantom in FIG. 44) disposed in channels 1366 formed in projections 1368 extending between the two sides of the proximal anchor legs 1358 prevents inadvertent actuation of the anchors. Stop surfaces 1370 and 1372 on flanges 1352 and 1354, respectively, meet to provide a limit to extension of gripper 1350, as shown in FIG. 48.

Figure 49:
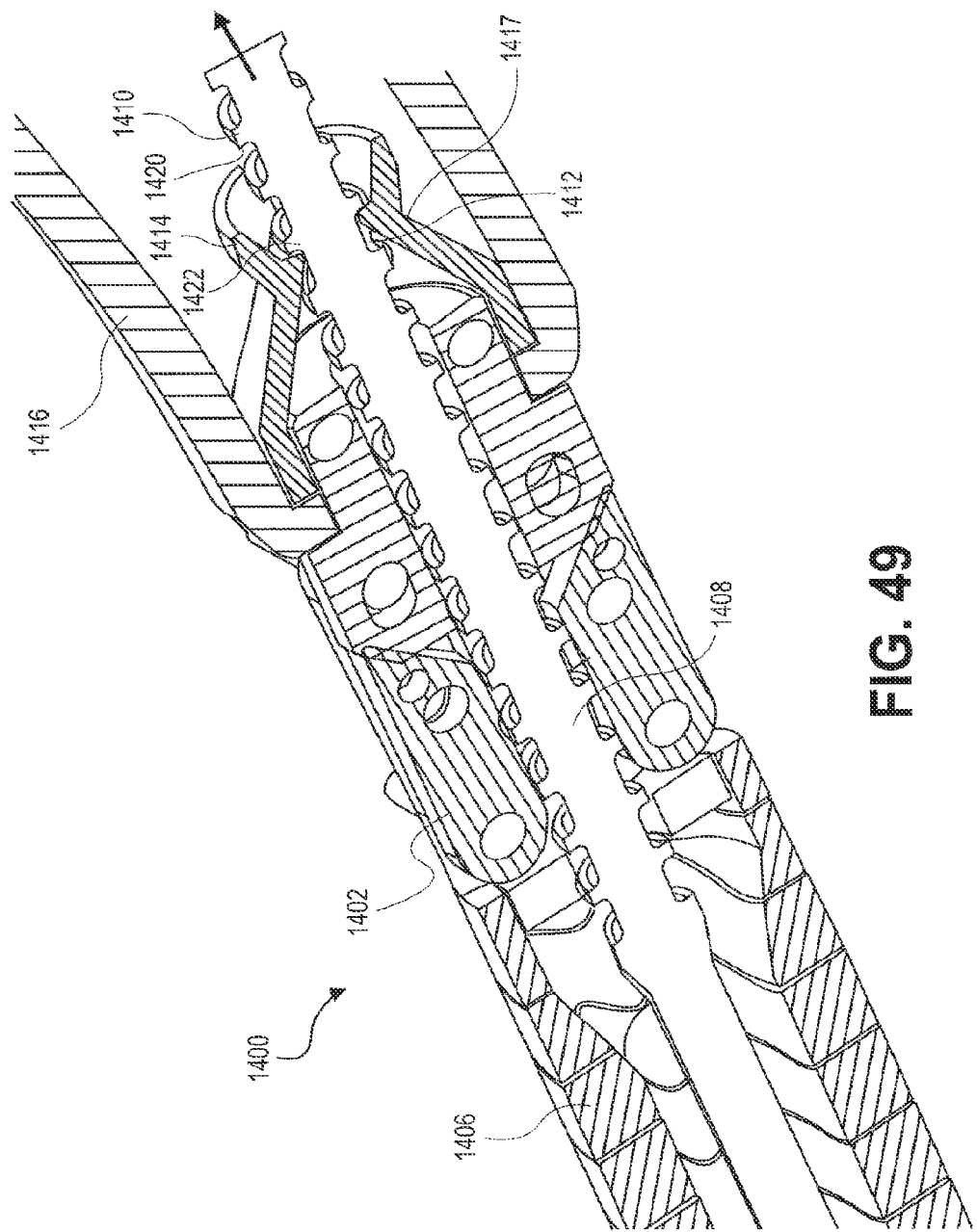
FIGS. 49-50 show another embodiment of a fracture fixation device similar to the device shown in FIGS. 19-25 using a distal gripper similar to that shown in FIGS. 44-48 but using an alternative actuator/locking mechanism.
Figure 50:
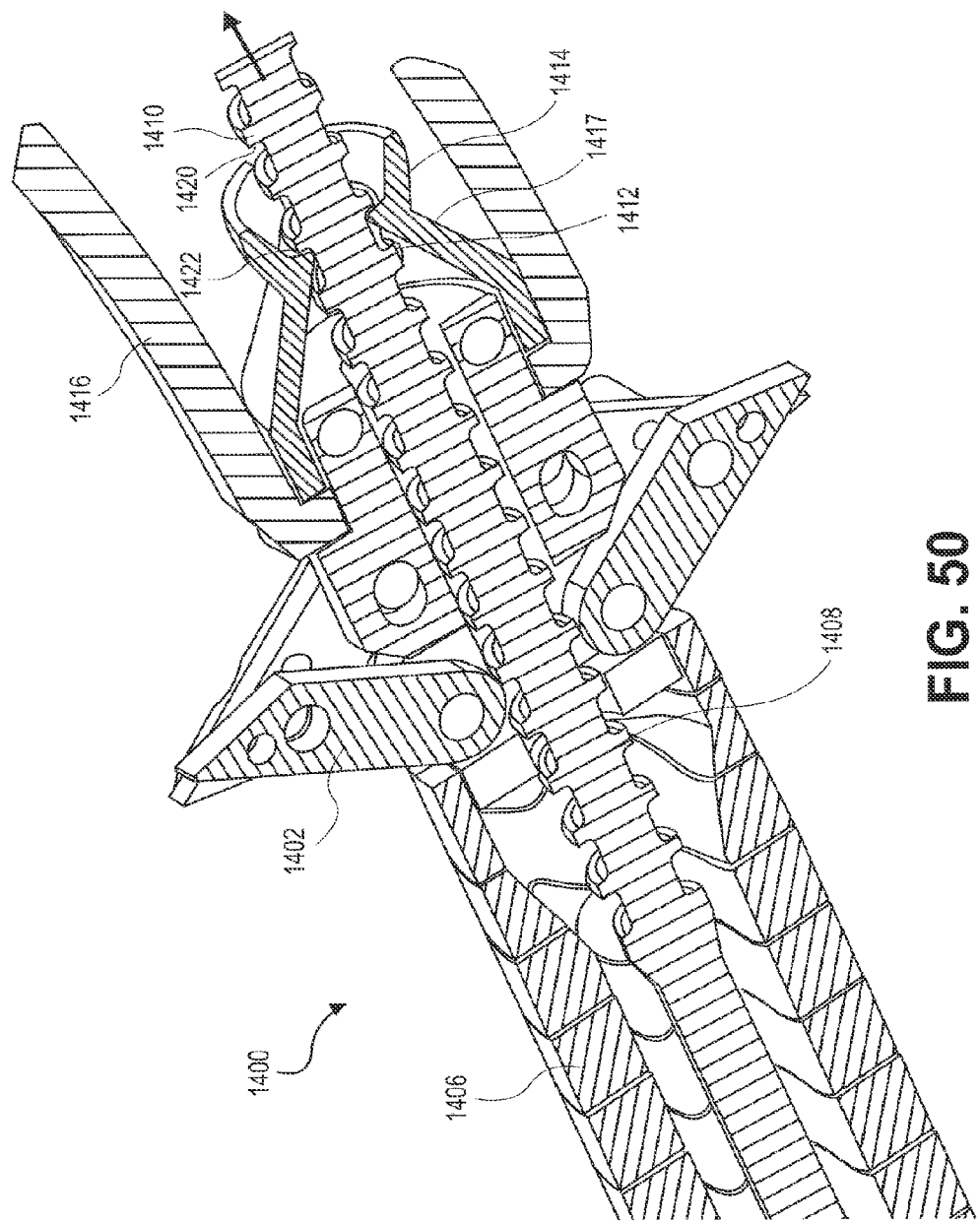

FIGS. 49-50 show another embodiment of a fracture fixation device 1400 similar to device 1100 shown in FIGS. 19-25 using a distal gripper 1402 similar to that shown in FIGS. 44-48. Instead of a threaded rotating actuator, however, device 1400 uses a ratcheting actuator 408. Actuator passes through device hub 1416, gripper 1402 and flexible-to-rigid body 1406 to a flange (not shown) at the other end of the fixation device. To foreshorten and actuate the fixation device (thereby extending the grippers and rigidizing the flexible-to-rigid body, actuator 1408 is tensioned by pulling in the direction of the arrow in FIG. 49 while keeping the rest of the device 1400 stationary. As it moves distally, ridges 1410 formed in actuator push against a cam surface 1412 formed in crown 1414 in ratchet 1417, expanding the crown enough to permit the ridges to pass through. After passing through the crown, surface 1420 of ridge 1410 meets a stop surface 1422 of ratchet crown 1414, thereby preventing proximal movement of actuator 1408 after it has been tensioned. After deployment of the fracture fixation device within a fractured bone, the portion of actuator 1408 extending from the end of the device after suitable tensioning may be cut and removed. A tool (not shown) may be used to release the ratchet in the event fixation device 1400 must be repositioned or removed.

Figure 51:
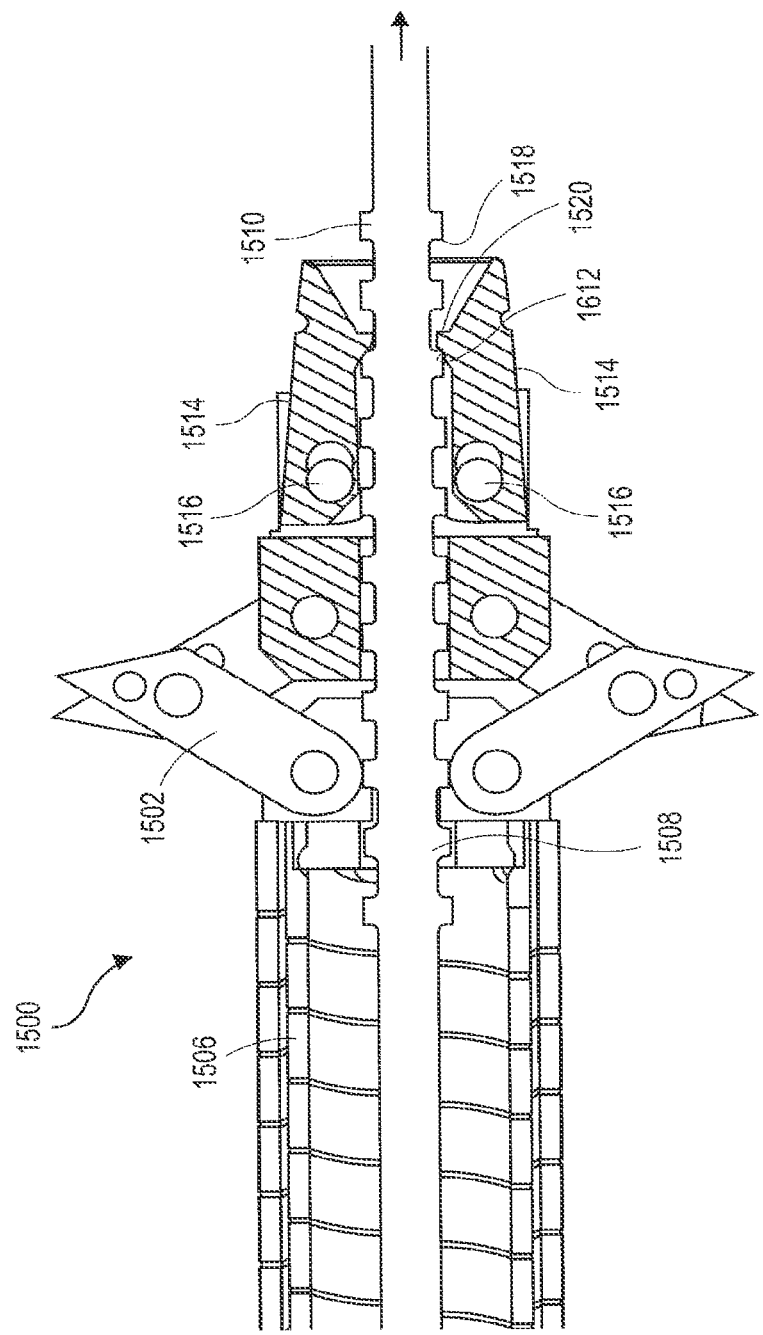
FIGS. 51-52 show yet another embodiment of a fracture fixation device similar to the device shown in FIGS. 49-50 but using another alternative actuator and an alternative flexible-to-rigid body.
Figure 52:
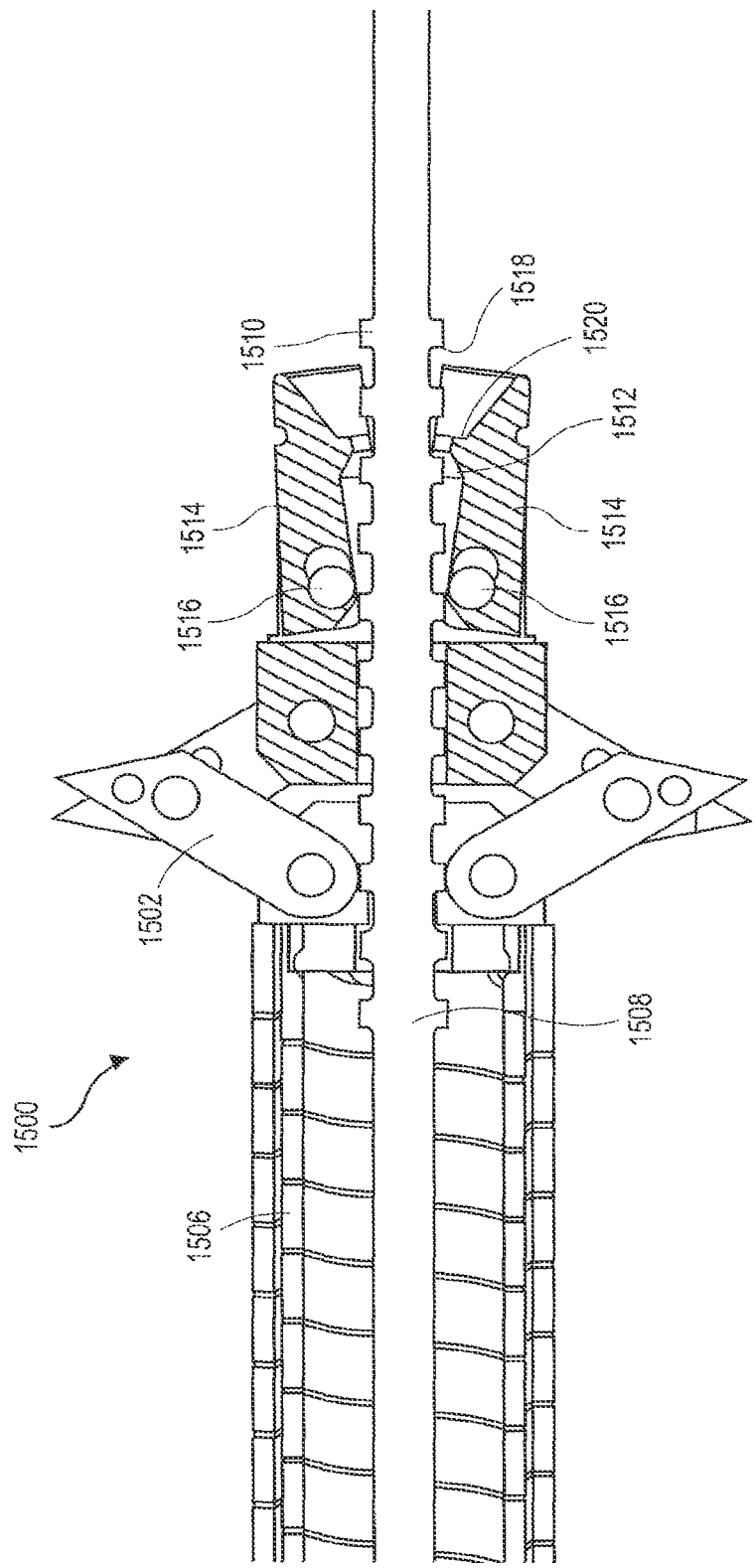

FIGS. 51-52 show yet another embodiment of a fracture fixation device 1500 similar to that of FIGS. 49-50. Flexible body has two concentric tubular members 1506A and 1506B with opposing clockwise/counterclockwise helical cuts. In order to rigidize flexible body 506 and deploy gripper 1502, actuator 1508 is tensioned in the direction of Arrow A in FIG. 51. As it moves in that direction, ridges 1510 of actuator 1508 move against cam surfaces 1512 of ratchet members 1514, which rotate outwardly around pins 1516. The interaction of face 1518 of ridge 1510 with face 1520 of ratchet member 1514 prevents actuator 1508 from moving back the direction it came. The actuator 1508 may be released from the ratchet by using a tool (not shown) to move the ratchet members 1514 to the position shown in FIG. 52.

Figure 53:
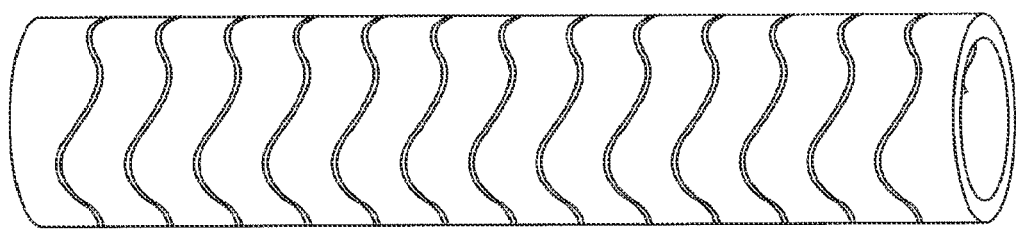
FIGS. 53-59 show alternative designs for the flexible-to-rigid body of a fracture fixation device according to this invention.
Figure 54:
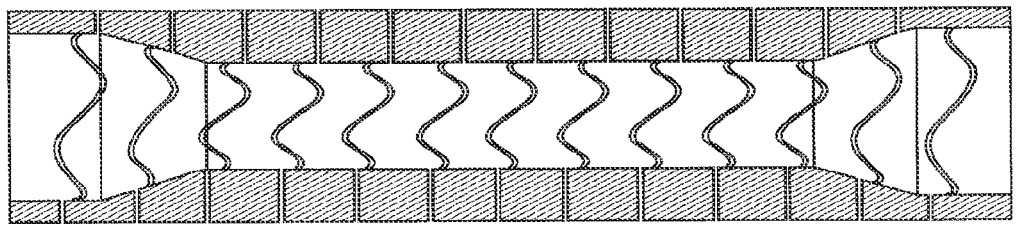
Figure 55:
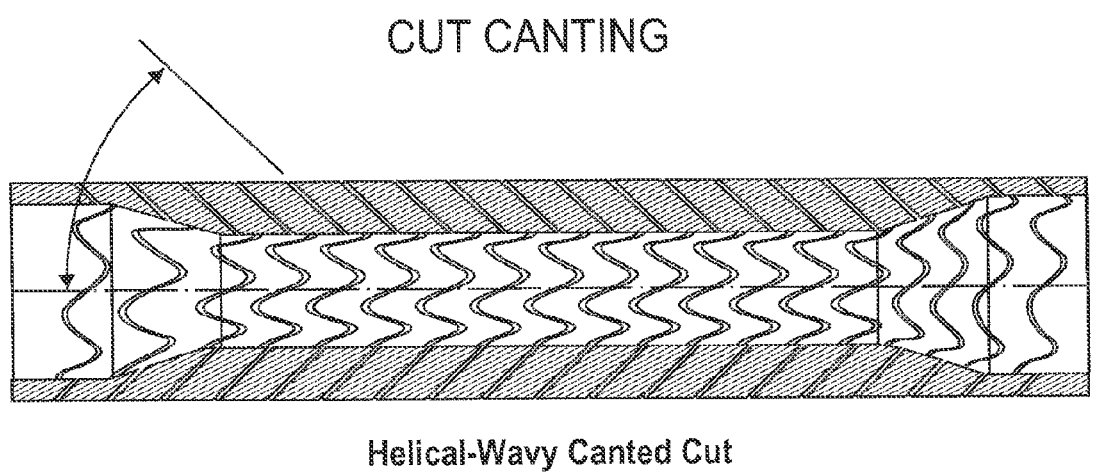
Figure 56:
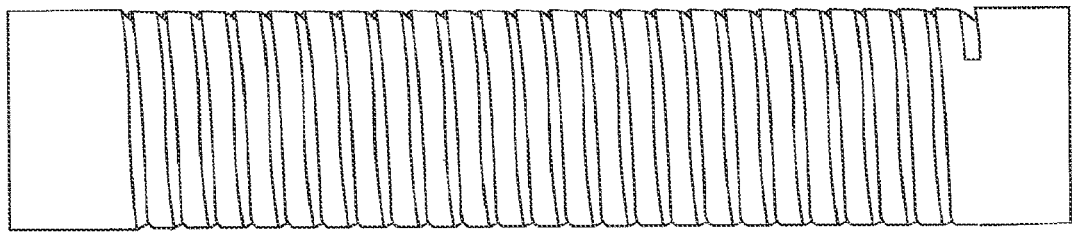
Figure 57:
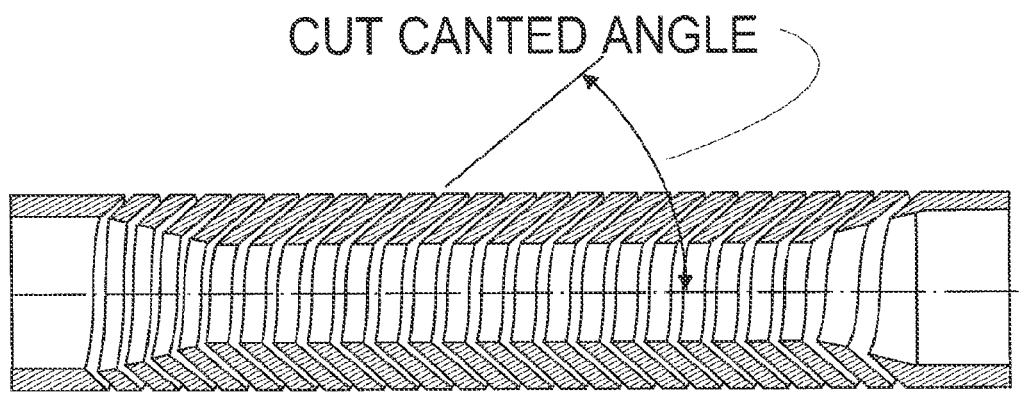
Figure 58:
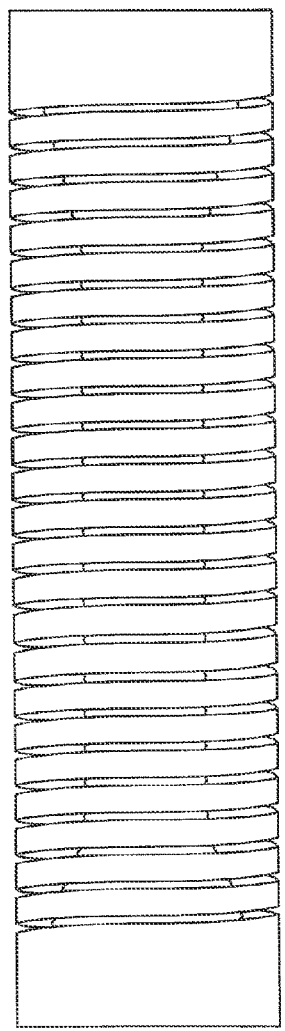
Figure 59:
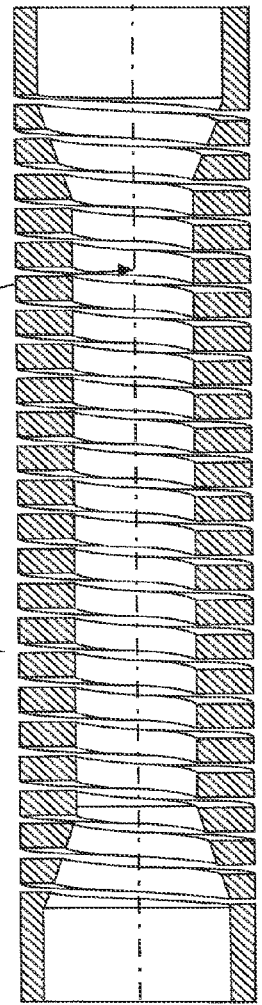

FIGS. 53-59 show alternative designs for the flexible body of a fracture fixation device according to this invention. FIGS. 53 and 54 show helical wavy cuts formed in the flexible-to-rigid body so that it is flexible when not compressed and rigid when foreshortened and compressed. FIG. 55 shows a canted helical wavy cut formed in the flexible-to-rigid body. FIGS. 56 and 57 show canted angles formed in the helical cuts of the flexible-to-rigid body. FIGS. 58 and 59 show a helical cut to form the flexible-to-rigid body. As in the earlier embodiments, the shape of the helical turns enables the transmission of bending and torque along the flexible-to-rigid body, in addition to the rigidizing function the body performs.

Figure 10B:
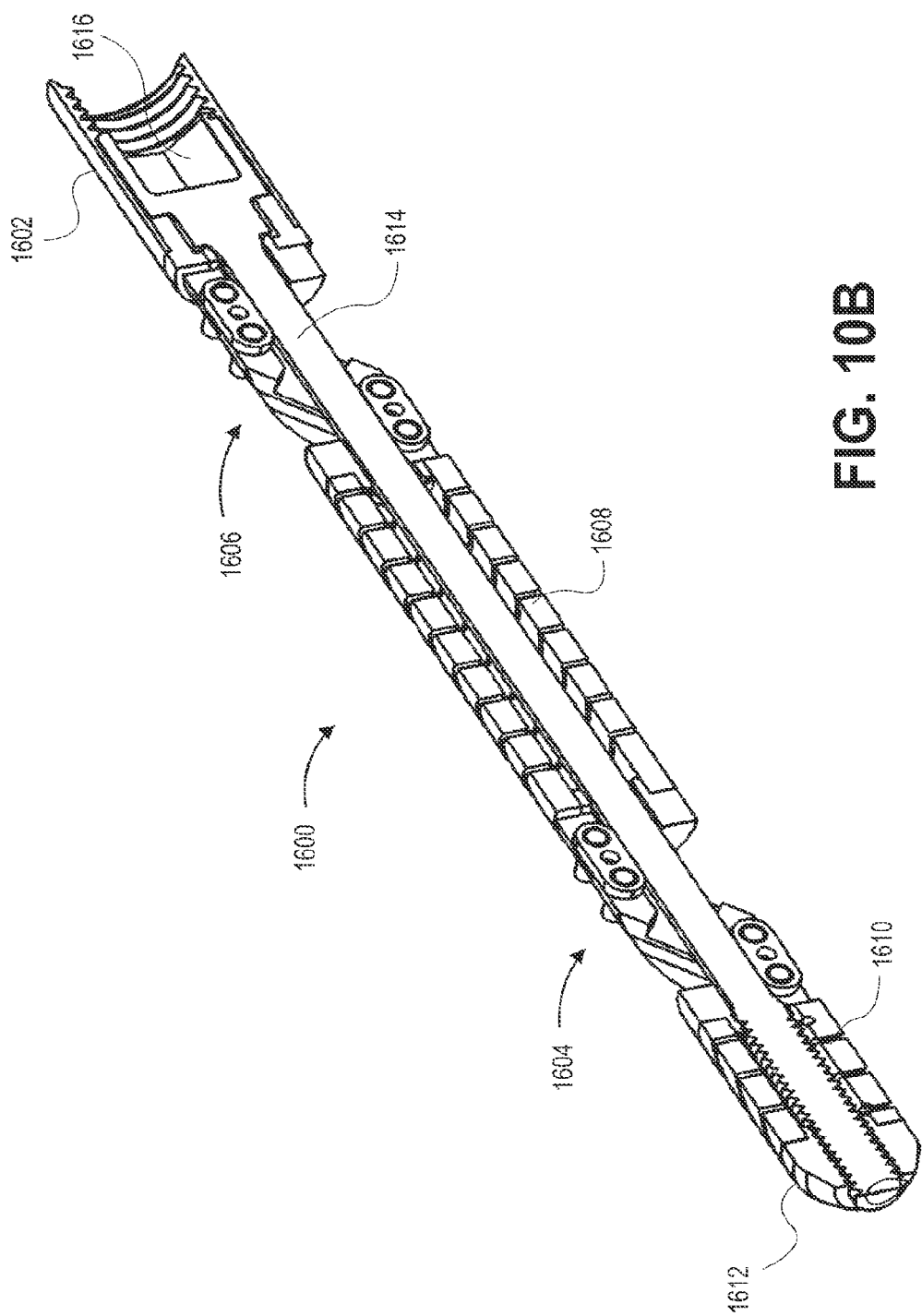
Figure 11A:
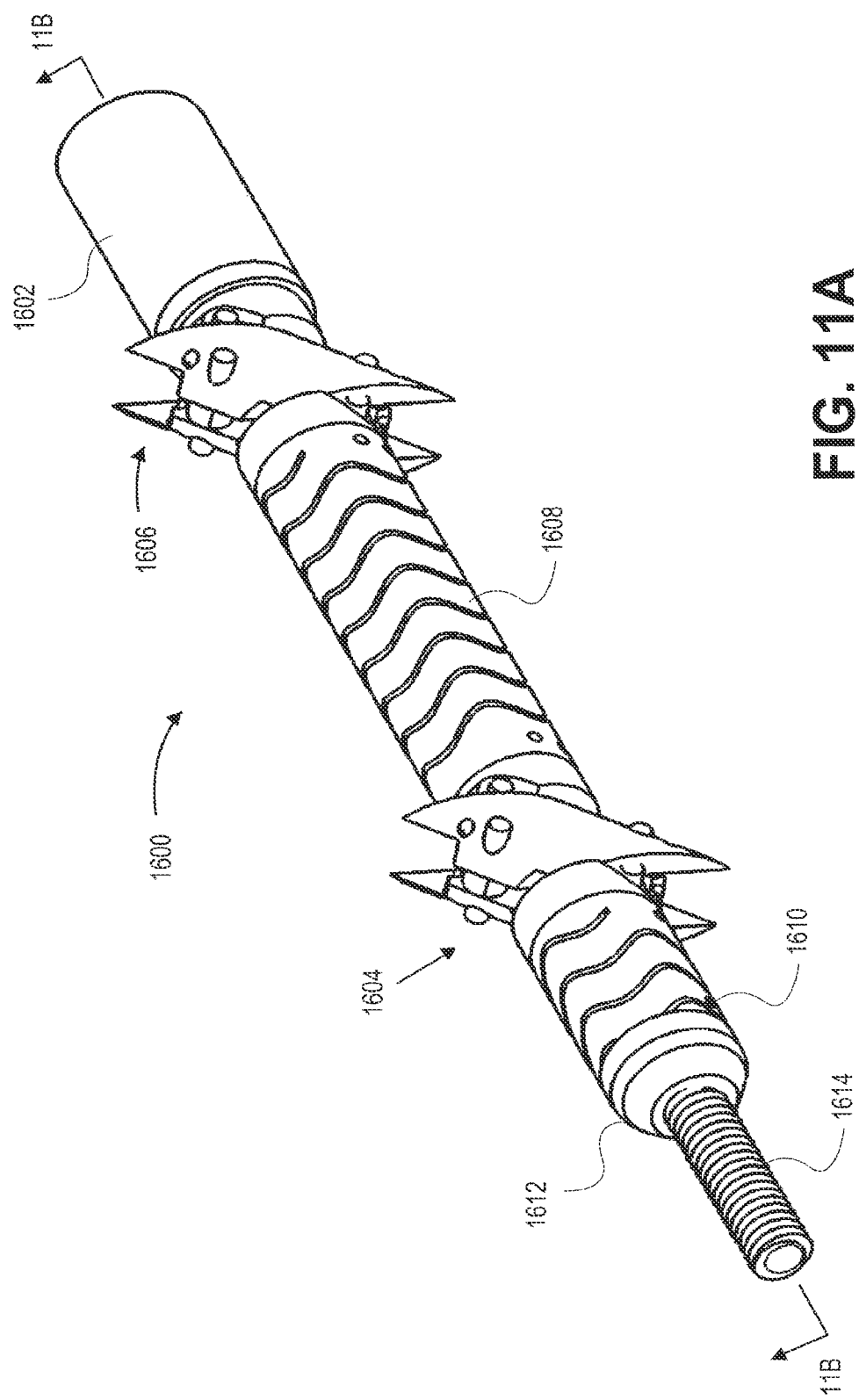
FIG. 11A is a perspective view showing the bone repair device of FIGS. 10a and 10b in a deployed state.
Figure 11B:
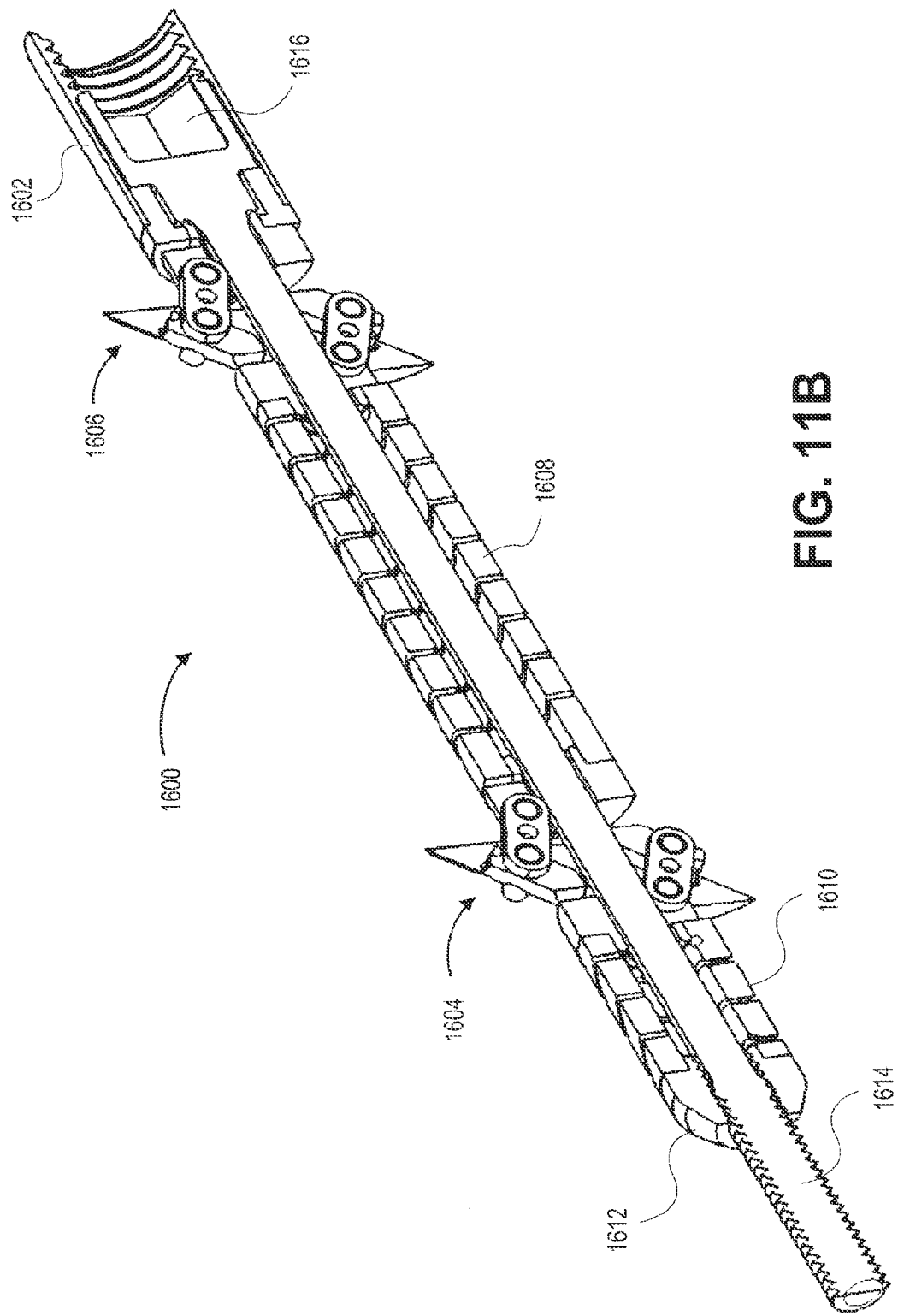
Figure 12:
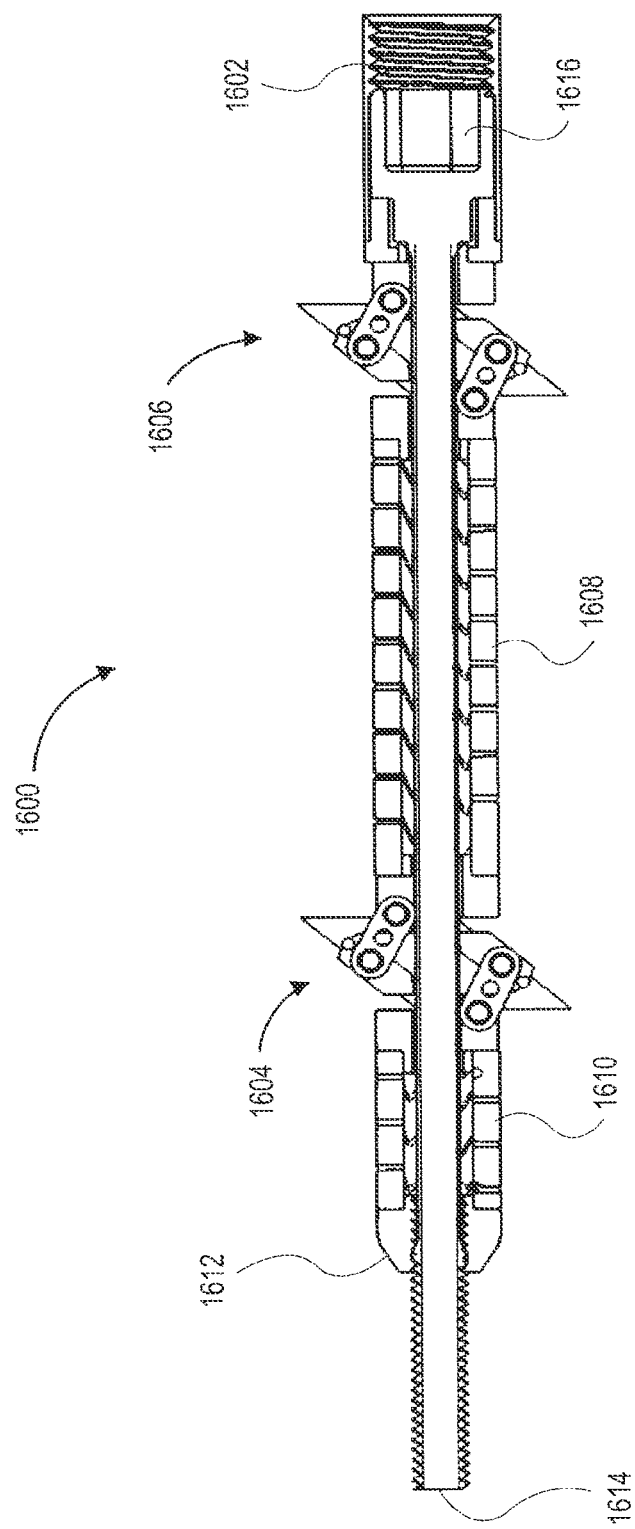
FIG. 12 is a cross sectional elevation view showing the bone repair device of FIG. 11b.

FIGS. 10a-10b, 11a-11b and 12 show an alternative embodiment of a fracture fixation device 1600 according to aspects of the invention. In FIGS. 10a-10b, device 1600 is shown in a retracted state, and in FIGS. 11a-11b and FIG. 12, device 1600 is shown in a deployed state. Like some earlier embodiments, fixation device 1600 has a hub 1602, grippers 1604 and 1606 and a flexible-to-rigid body 1608. Grippers 1604 and 1606 may be constructed in a manner similar to gripper 1070 shown in FIGS. 13-15 and described above. One or more additional flexible-to-rigid body sections may be used, such as section 1610 located between gripper 1604 and nose cone 1612 as shown. A threaded actuator 1614 extends through the device to threadably engage nose cone 1612. A rotational tool engagement portion 1616 may be provided on the hub end of the actuator b to rotate the actuator.

After device 1600 is inserted in place within an intramedullary space of a fractured bone and spanning a fracture site, actuator 1614 may be rotated with a tool inserted in portion 1616. As actuator 1614 is rotated, threaded nose cone 1612 travels distally with respect to the grippers and the flexible-to-rigid components while hub 1602 remains stationary. This action foreshortens device 1600 to deploy grippers 1604 and 1606 and to rigidize components 1608 and 1610. When deployed to the configuration shown in FIGS. 11a-11b and FIG. 12, grippers 1604 and 1606 tilt outward to dig their tips into the interior surface of the bone. To reposition or remove device 1600 from the bone, the actuator may be rotated in the other direction to release the grippers and to permit the flexible-to-rigid components to become flexible again.

Figure 60A:
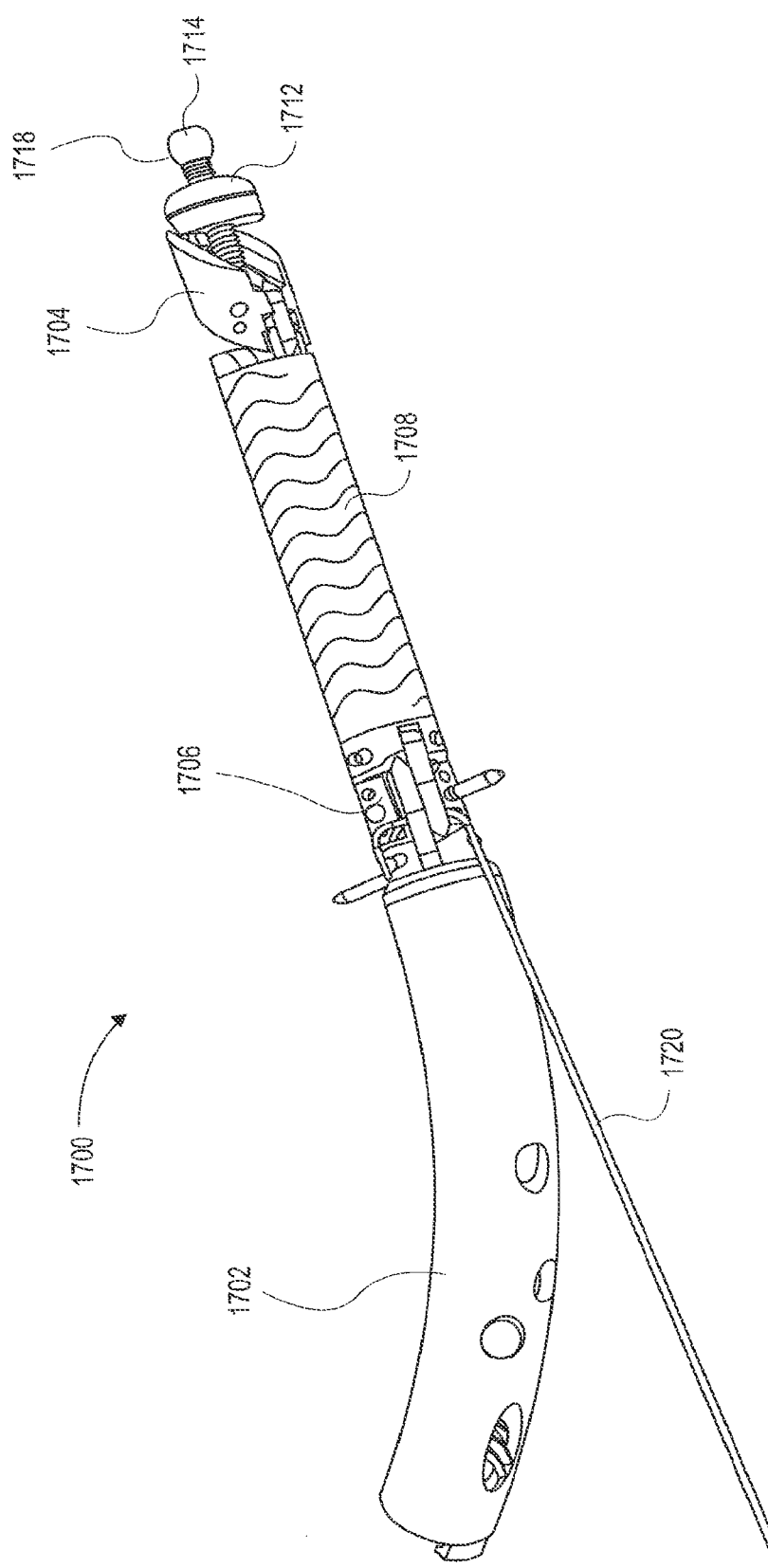
FIGS. 60A-B show an alternative embodiment of a fracture fixation device in a retracted state.
Figure 60B:
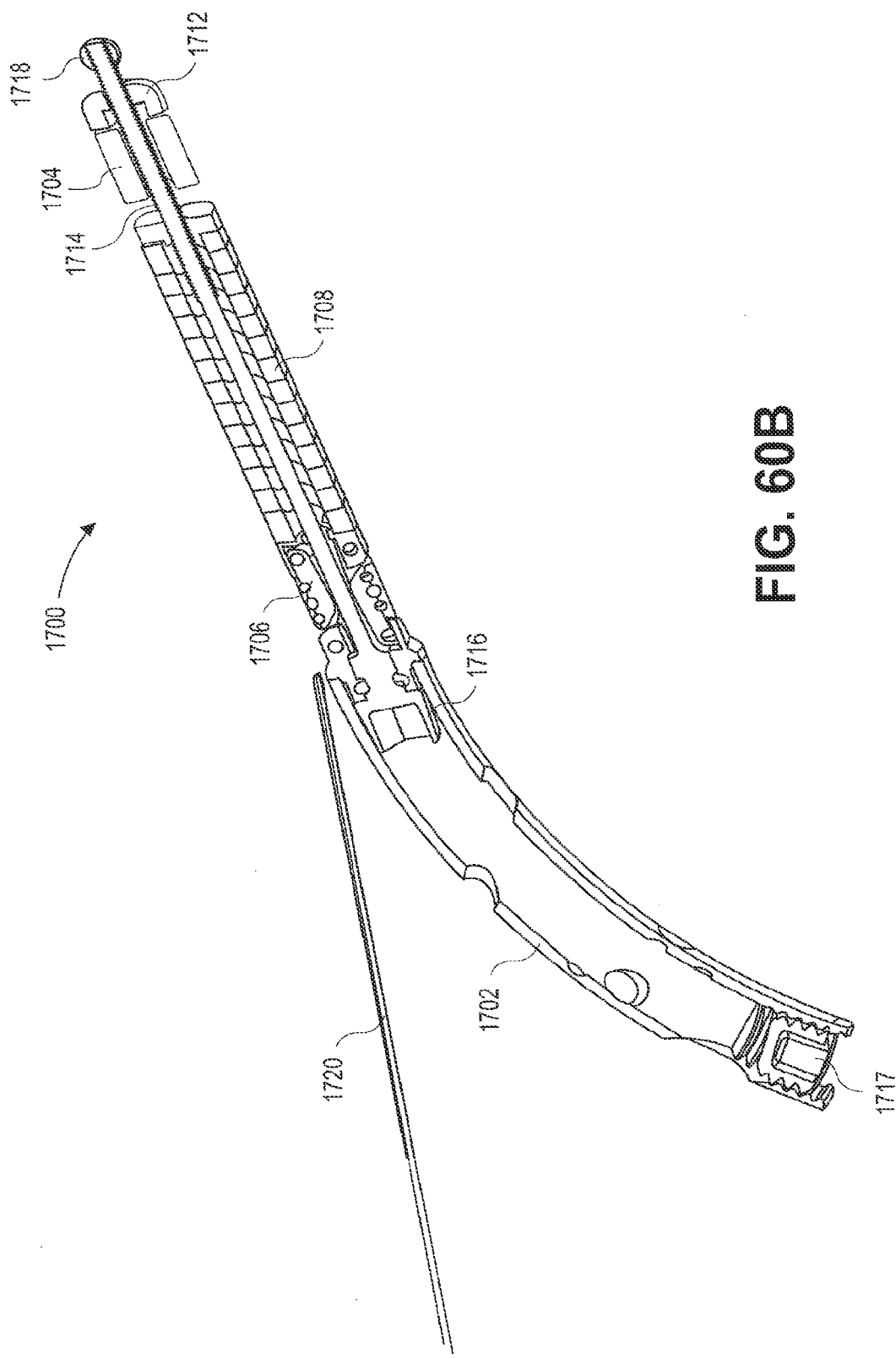
Figure 61A:
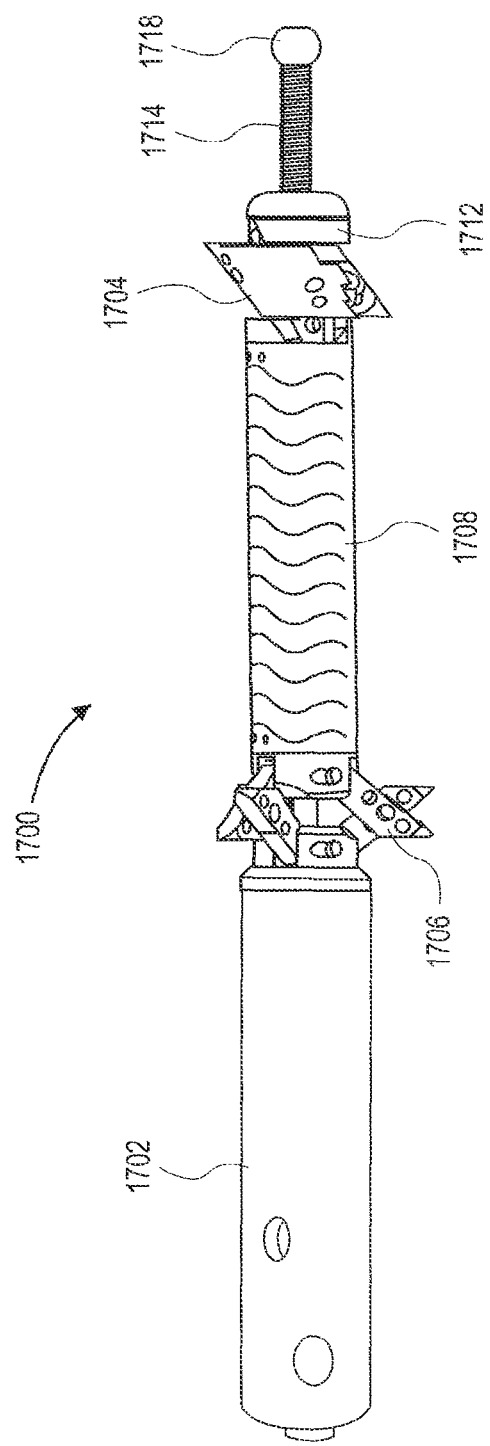
FIGS. 61A-B show the device of FIGS. 60a-b in a deployed state.
Figure 61B:
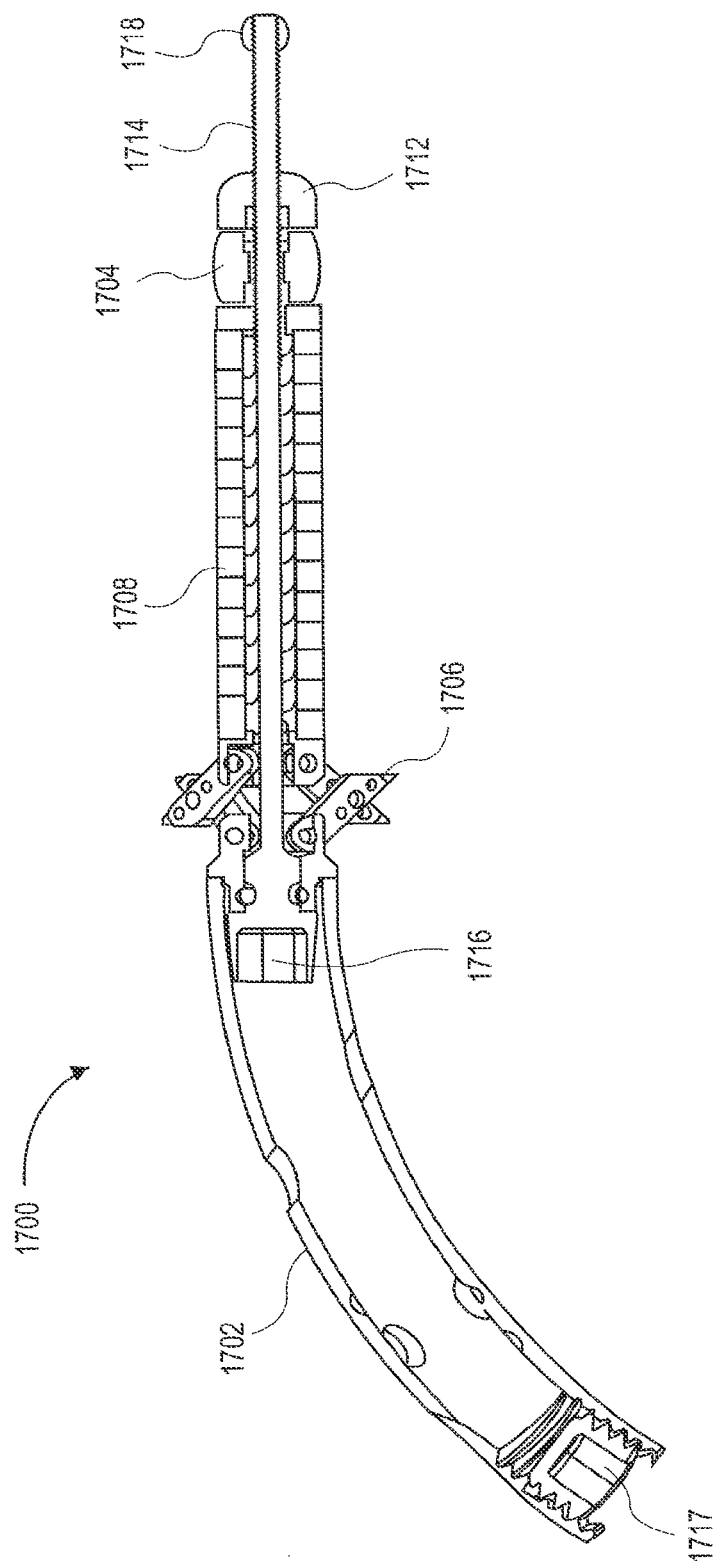

FIGS. 60a-60b and 61a-61b show an alternative embodiment of a fracture fixation device 1700 according to aspects of the invention. In FIGS. 60a-60b, device 1700 is shown in a retracted state, and in FIGS. 61a-61b, device 1700 is shown in a deployed state. Like some earlier embodiments, fixation device 1700 has a hub 1702, grippers 1704 and 1706 and a flexible-to-rigid body 1708. Gripper 1704 may be constructed in a manner similar to gripper 1070 shown in FIGS. 13-15 and described above. Tripod gripper 1706 may be constructed in a manner similar to gripper 1104 shown in FIGS. 22-33 and described above. A threaded actuator 1714 extends through the device to threadably engage nose cone 1712. A rotational tool engagement portion 1716 may be provided on the hub end of the actuator 1714 to rotate the actuator. A threaded cap 1717 may be provided to close opening of hub 1702 after fixation of the fracture to prevent bone and tissue ingrowths. A stop element, such as ball 1718, may be crimped, welded or otherwise attached to the opposite end of actuator 1714 to prevent the actuator from being turned so far in the gripper retraction direction that actuator 1714 disengages from nose cone 1712 and device 1700 comes apart, particularly after insertion into the bone.

The bent tip of a safety wire 1720 may be engaged in the aligning holes of a pair of arms of gripper 1706 when in a retracted position, as shown in FIGS. 60a-60b. Such an arrangement can help ensure that tripod gripper 1706 does not prematurely deploy as device 1700 is being inserted into a medullary canal. After device 1700 is inserted into the medullary canal, safety wire 1720 may be disengaged and removed. Actuator 1714 can then be rotated, drawing nose cone 1712 toward the hub end of device 1700 to actuate grippers 1704 and 1706 in a radially outward direction, and compressing body section 1708 in an axial direction to change it from a flexible state to a rigid state as previously described.

Figure 62A:
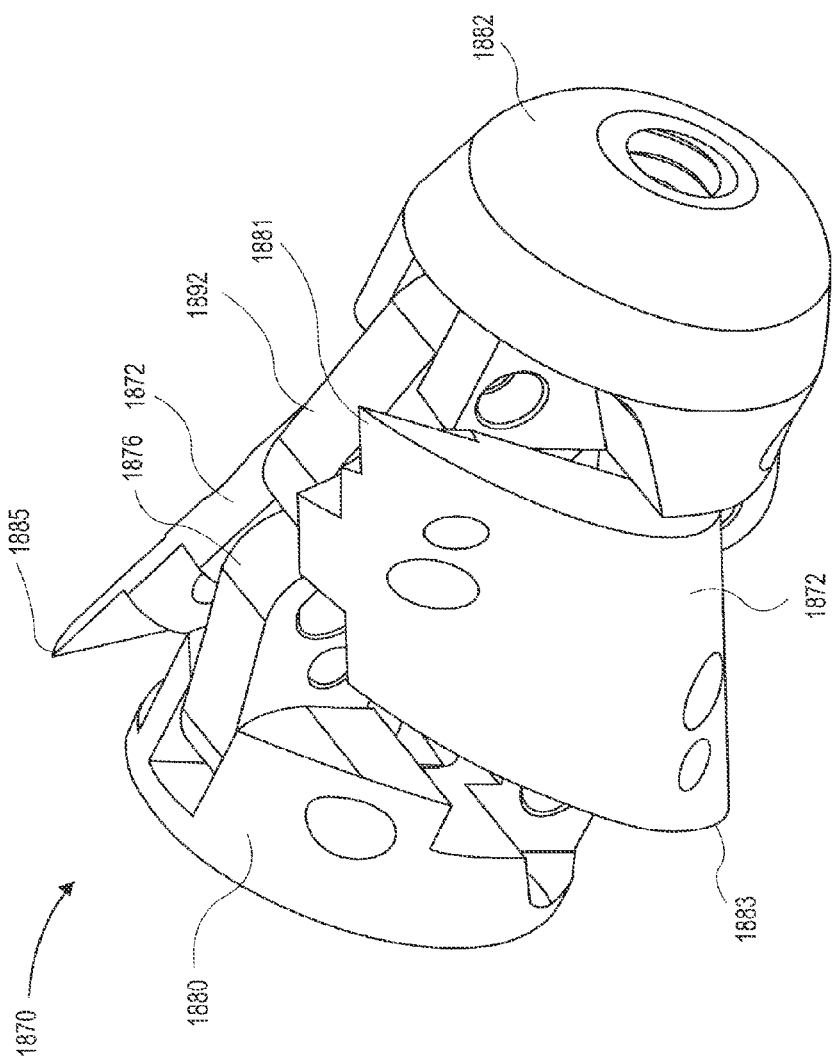
FIGS. 62A-B show another embodiment of a gripper mechanism.
Figure 62B:
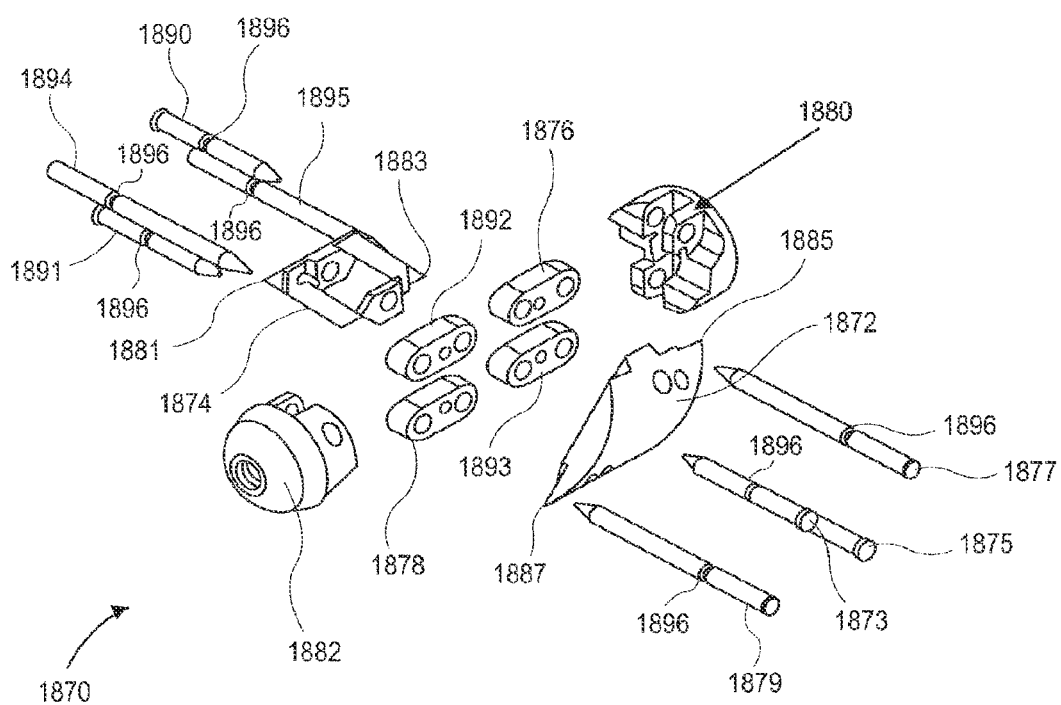

FIGS. 62a and 62b shown an alternative gripper design embodiment, similar to gripper 1070 shown in FIGS. 13-15 and described above, for use with, e.g., the fracture fixation device embodiments described above. In this embodiment, gripper 1870 has two rotatable cams 1872 and 1874. Cam 1874 is attached by pins 1873 and 1875 to cam arms 1892 and 1893, respectively. Cam arms 1892 and 1893 attach by pins 1894 and 1895 to flanges 1882 and 1880, respectively. Similarly, cam 1872 is attached by pins 1890 and 1891 to cam arms 1876 and 1878, respectively. Cam arms 1876 and 1878 attach by pins 1877 and 1879 to flanges 1880 and 1882, respectively. Pins 1873, 1875, 1877, 1879, 1890, 1891, 1894 and 1895 may be fabricated longer than necessary to ease assembly of gripper 1870. Each pin can include a stress concentration 1896 so that once the pin is inserted in its proper position and held in place by a press fit, welding or other means, the excess portion of the pin may be snapped off. Flanges 1880 and 1882 connect with the components on either end of the device.

In an undeployed configuration, cams 1872 and 1874 are oriented such that the sharp tips 1885 and 1887 of cam 1872 and the sharp tips 1881 and 1883 of cam 1874 do not extend from the cylinder of the gripper. When foreshortened during deployment, however, movement of flanges 1880 and 1882 toward each other causes cam arms 1876 and 1878 to rotate about pins 1877 and 1879 with respect to flanges 1880 and 1882 and causes cam 1872 to rotate about pins 1890 and 1891 with respect to cam arms 1876 and 1878 so that the sharp tips swing out from the cylinder of the gripper, as shown in FIG. 62a. Similarly, movement of flanges 1880 and 1882 toward each other causes cam arms 1892 and 1893 to rotate about pins 1894 and 1895 with respect to flanges 1882 and 1880 and causes cam 1874 to rotate about pins 1873 and 1875 with respect to cam arms 1892 and 1893 so that the sharp tips swing out from the cylinder of the gripper, as also shown in FIG. 62a. Thus, when part of a fracture fixation device has been inserted into a bone, deployment of the gripper 1870 causes the sharp tips of the cams to dig into the bone to anchor the device. It should be noted that unlike cams 1072 and 1074 of gripper 1070 shown in FIGS. 13-15, cams 1872 and 1874 of gripper 1870 shown in FIGS. 62a-62b rotate in opposite directions when deployed. It should also be noted that in all embodiments disclosed herein, in the event of inadvertent breakage of an actuator or other component, the grippers are configured to nonetheless be able to return to a retracted position so that the device may be removed from its implanted position in the bone.

Figure 63:
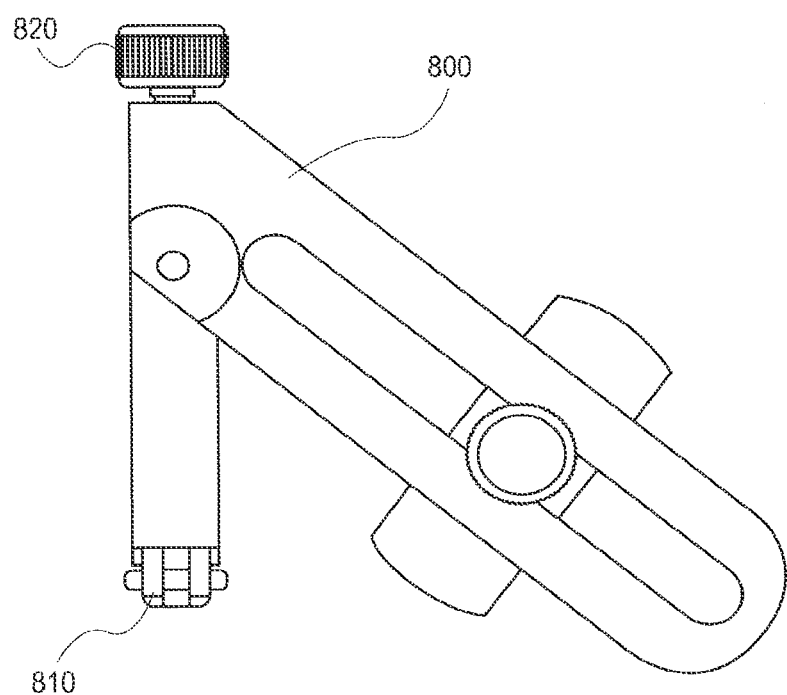
FIG. 63 shows an embodiment of an outrigger device.

FIG. 63 shows an embodiment of an outrigger tool 800. The outrigger 800 allows precise placement of ancillary devices to the primary implant. An ancillary device includes a K-wire, screw, biological matrix, allograft, therapeutic, and or other material to aid in bone reconstruction. The outrigger provides a datum that acts as an interface to the primary datum of the primary implant. As such, the outrigger sets the coordinate system for placement of ancillary material. In the case of a bone screw or K-wire, the outrigger ensures the bone screw creates a bone, implant bone interface and prevents interference or destruction of important soft tissue. In the case of a bone screw for the distal radius, the outrigger ensures the bone screw attaches bone to the hub of the implant and further ensures that the screw cannot penetrate the radial ulnar joint or the epiphysis. In the case of the placement of biological matrices, osteogenic protein can be placed at the fracture site using the outrigger and x-ray guidance. In the case of therapeutic materials, the outrigger allows precise positioning of these materials for maximum effectiveness. The outrigger has an interface to the implant that is easily attached and removed by the surgeon. In one embodiment the attachment is a threaded collar, another embodiment includes a bayonet, and yet another embodiment includes a cantilever snap fit. Once attached to the implant the outrigger and implant form an integral unitary construction. The outrigger can be used to push and pull the implant into and out of the intramedullary canal. The outrigger can serve as an interface to drive the implant into the intramedullary space with a kinetic energy device such as a hammer. The outrigger has an orifice that accommodates a guidewire or ratcheting guidewire. The outrigger can have an implement that applies a relative force in the opposite direction of the patient on the guidewire or ratcheting guidewire. As such the guidewire is pulled out of the patient and in the case of the ratcheting guidewire, the implant is expanded and the implant forms a secure attachment to the diaphyseal bone. The outrigger can be used with a variety of hubs. The outrigger can be used with a variety of bone repair device designs and does not need to be self-locking The bone-device-bone interface enables it to stay in position.

Outrigger 800 has a connector portion 810 that connects to the hub and enables drilling through bone into the hub of the target implant, such as those described above. In this embodiment, thumbscrew 820 is used to secure the hub to connector portion 810. A feature of the outrigger is that it enables drilling holes into the center of the hub without visualization. Additionally, the sliding drill hole member on the outrigger allows a large variation of angles that cross the hub. As will be appreciated by those skilled in the art, the optimal angle will be effected by the geometry of the broken bone to be repaired. After the starter screw hole is dilled in the bone, the drill is removed and a screw is inserted into the same outrigger hole, thereby guiding the screw to the starter-hole in the bone.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A method of repairing a fracture of a long bone, the method comprising:
   advancing a bone fixation device across a fracture of an intramedullary space of a long bone,
   wherein the bone fixation device comprises a rigid hub, a plurality of gripper elements, and an elongate body,
   wherein the rigid hub comprises a first end and a second end and the rigid hub is advanced to a position spanning the fracture;
   operating an actuator from the second end of the rigid hub so as to inhibit movement of the elongate body; and
   deploying the plurality of gripper elements of the bone fixation device from an advancement configuration to a deployed configuration extending radially outwardly from the elongate body so as to engage an inner surface of the intramedullary space to anchor the bone fixation device to the long bone,
   further comprising inserting a screw into the bone on one side of the fracture and through the rigid hub so that, when implanted, the gripper elements and the screw affix the bone fixation device to the bone on the one side of the fracture,
   wherein the step of advancing a bone fixation device is performed while the rigid hub has a preformed bore, the step of inserting a screw comprising inserting the screw through the bone and the preformed bore,
   wherein the rigid hub has a plurality of preformed holes, the method comprising inserting a first screw dorsal to volar through two portions of the bone and a first and second of the preformed holes and inserting a second screw volar to dorsal through two other portions of the bone and a third and fourth of the preformed holes.

2. The method of claim 1 wherein the operating step comprises rotating the actuator with respect to the bone fixation device.

3. The method of claim 1 wherein the operating step comprises pivoting at least one of the plurality of gripper elements away from a longitudinal axis of the elongate body.

4. The method of claim 3 wherein the operating step comprises pivoting at least two of the plurality of gripper elements away from the longitudinal axis of the elongate body.

5. The method of claim 3 wherein the pivoting step comprises moving at least two bone engaging surfaces of the plurality of gripper elements into engagement with the bone.

6. The method of claim 3 wherein the pivoting step comprises moving at least three of the plurality of gripper elements away from the longitudinal axis of the elongate body, the at least three of the plurality of gripper elements being disposed circumferentially around the elongate body at the same axial position.

7. The method of claim 3 wherein the pivoting step comprises pivoting a pair of the plurality of gripper elements disposed on opposite sides of the elongate body at the same axial position so that two surfaces of each of the gripper elements engage the inner surface of the intramedullary space.

8. The method of claim 7 wherein the pivoting step comprises rotating the plurality of gripper elements in a first direction.

9. The method of claim 1 wherein the long bone is any one of the group consisting of a radius, ulna, humerus, clavicle, femur, tibia, and fibula.

10. The method of claim 1 further comprising forming a bore through the bone prior to inserting the screw.

11. The method of claim 1 further comprising inserting a third screw proximal to distal through two more portions of the bone and fifth and sixth of the preformed holes of the hub.

12. The method of claim 1 further comprising attaching a drill alignment guide to the rigid hub and aligning a drill bit with the hub using the drill alignment guide, wherein the screw is inserted in the bone using a hole in the bone drilled with the aligned drill bit.

13. The method of claim 1 wherein advancing the bone fixation device into the intramedullary space of the bone comprises the use of a guidewire.

14. The method of claim 13 wherein the guidewire is used to guide tools in preparing the intramedullary space of the bone prior to advancing the bone fixation device.

15. The method of claim 1, wherein the fixation device is inserted into an opening in a second portion of the bone, wherein the elongate body of the fixation device comprises a tubular body having a generally helical cut, the generally helical cut facilitating flexing along the elongate body when the elongate body is inserted into the intramedullary space through the opening; the generally helical cut defining a wave superimposed on a helical cut along a circumferential turn of the generally helical cut, the wave engaging an adjacent circumferential turn of the generally helical cut so as to transmit torque along the elongate body; and wherein the method further comprises rigidizing the elongate body from a flexible state to a rigid state by imposing an axial load on the tubular body in response to rotating the actuator about an axis of the rigid hub so as to inhibit axial flexing along the tubular body.

16. The method of claim 1, wherein the fixation device is inserted into an opening in a second portion of the bone, wherein the elongate body of the fixation device comprises a tubular body having a plurality of segments, the plurality of segments facilitating flexing along the elongate body when the elongate body is inserted into the intramedullary space through the opening; the plurality of segments configured to transmit torque along the elongate body; and wherein the method further comprises rigidizing the elongate body from a flexible state to a rigid state by imposing an axial load on the tubular body in response to rotating the actuator about an axis of the rigid hub so as to inhibit flexing along the tubular body.

* * * * *